US012728116B2

(12) United States Patent
DiBernardo et al.

(10) Patent No.: US 12,728,116 B2
(45) Date of Patent: Sep. 8, 2026

(54) METHODS OF TREATING MULTIPLE SCLEROSIS

(71) Applicant: Vanda Pharmaceuticals Inc., Washington, DC (US)

(72) Inventors: Allitia DiBernardo, Philadelphia, PA (US); Maria Ait-Tihyaty, Montreal (CA)

(73) Assignee: Vanda Pharmaceuticals Inc., Washington, DC (US)

( * ) Notice: Subject to any disclaimer, the term of this patent is extended or adjusted under 35 U.S.C. 154(b) by 806 days.

(21) Appl. No.: 17/962,679

(22) Filed: Oct. 10, 2022

(65) Prior Publication Data

US 2023/0144895 A1 May 11, 2023

Related U.S. Application Data

(60) Provisional application No. 63/254,410, filed on Oct. 11, 2021.

(51) Int. Cl.

*A61K 31/426* (2006.01)
*A61P 25/00* (2006.01)
*A61P 37/00* (2006.01)

(52) U.S. Cl.

CPC ............ *A61K 31/426* (2013.01); *A61P 25/00* (2018.01); *A61P 37/00* (2018.01)

(58) Field of Classification Search

CPC ........ A61K 31/426; A61P 21/00; A61P 25/00; A61P 25/28; A61P 37/00
See application file for complete search history.

(56) References Cited

U.S. PATENT DOCUMENTS

| | | | |
|---|---|---|---|
| 4,284,786 | A | 8/1981 | Friedrich-Johannes |
| 4,959,389 | A | 9/1990 | Speiser |
| 8,232,250 | B2 | 7/2012 | Klinger |
| 10,220,023 | B2 | 3/2019 | Dingemanse |

FOREIGN PATENT DOCUMENTS

| | | | | |
|---|---|---|---|---|
| CN | 103260624 | | 8/2013 | |
| CN | 106573014 | | 4/2017 | |
| EP | 0312697 | A2 | 4/1989 | |
| WO | 0030622 | A2 | 6/2000 | |
| WO | 2009115954 | A1 | 9/2009 | |
| WO | 2010022177 | A2 | 2/2010 | |
| WO | 2010046835 | A1 | 4/2010 | |
| WO | 2012061060 | A1 | 5/2012 | |
| WO | 2014152494 | A1 | 9/2014 | |
| WO | WO-2021013815 | A1 * | 1/2021 | ............. A61P 25/28 |
| WO | 2021176070 | A1 | 9/2021 | |

OTHER PUBLICATIONS

Sorensen, Drugs, vol. 64(a8), pp. 2021-2029, publ. 2004 (Year: 2004).*
Guerard N et al. Effect of Hepatic or Renal Impairment on the Pharmacokinetics, Safety, and Tolerability of Ponesimod, a Selective S1P1 Receptor Modulator, Basic Clin Pharmacol Toxicol-Article 2016, vol. 118, pp. 356-368.
Havrdova et al., "Efficacy and safety of 2 doses of ponesimod (10 and 20 mg once daily): Interim analysis of a Phase II extension trial in relapsing-remitting multiple sclerosis", Encore poster presented at AAN Apr. 21-27, 2018; Los Angeles, CA.
Hoch et al., "Clinical pharmacology of ponesimod, a selective S1P(1) receptor modulator, after up-titration to supratherapeutic doses in healthy subjects", Eur J Pharm Sci, vol. 63, pp. 147-153, 2014.
Hoch et al., "Effect of ponesimod, a selective S1P1 receptor modulator, on the QT interval in healthy individuals", Basic Clin Pharmacol Toxicol. May 2015; vol. 116(5), pp. 429-437.
Huwiler et al., "New players on the center stage: Sphingosine 1-phosphate and its receptors as drug targets", J. Biochem Pharmacol. Review, vol. 75(10), pp. 1893-1900; 2008.
Jurcevic S. et al., "Effects of multiple-dose ponesimod, a selective S1P(1) receptor modulator, on lymphocyte subsets in healthy humans", Drug Des Devel Ther. Dec. 28, 2016; vol. 11, pp. 123-131.
Kappos et al., A Placebo-Controlled Trial of Oral Fingolimod in Relapsing Multiple Sclerosis. N Engl J Med, vol. 362 (5): pp. 387-401; 2010.
Kappos L et al. "Oral fingolimod (FTY720) for relapsing multiple sclerosis", N Engl J Med 355(11), pp. 1124-1140; 2006.
Krause et al., "Modeling clinical efficacy of the S1P receptor modulator ponesimod in psoriasis", J Dermatol Sci. Feb. 2018; vol. 89(2), pp. 136-145. Epub Nov. 20, 2017.
Krause et al., "Population pharmacokinetics and pharmacodynamics of ponesimod, a selective S1P1 receptor modulator", J Pharmacokinet Pharmacodyn. Jun. 2014; vol. 41(3), pp. 261-278.
Lott D et al., "Modeling the Effect of the Selective S1P1 Receptor Modulator Ponesimod on Subsets of Blood Lymphocytes Pharmaceutical Research", 2017,34(3) 599-609.
Lott D et al., "Modeling Tolerance Development for the Effect on Heart Rate of the Selective S1P1 Receptor Modulator Ponesimod", Clin Pharmacol Ther. Jun. 2018;103(6):1083-1092. Epub Oct. 27, 2017.
Lott et al., "Population pharmacokinetics of ponesimod and its primary metabolites in healthy and organ-impaired subjects", Eur J Pharm Sci. Jun. 30, 2016; 89:83-93. Epub Apr. 22, 2016.
Lublin,"Disease activity free stats in MS", Mult Scler Relate Disord., Jan. 2012, 1(1), 6-7.
O'Connor et al., "Randomized Trial of Oral Teriflunomide for Relapsing Multiple Sclerosis", New England J. Med., 2011, 365, 1293-1230.
Piali et al., "The selective sphingosine 1-phosphate receptor 1 agonist ponesimod protects against lymphocyte-mediated tissue inflammation", J Pharmacol Exp Ther. May 2011; vol. 337(2), pp. 547-556.

(Continued)

*Primary Examiner* — Sarah Pihonak
(74) *Attorney, Agent, or Firm* — Hoffman Warnick LLC

(57) ABSTRACT

The disclosure relates to methods of treating multiple sclerosis. In certain aspects, methods of treating early-stage multiple sclerosis in a patient are disclosed.

30 Claims, 42 Drawing Sheets

(56) References Cited

OTHER PUBLICATIONS

Pouzol et al., "Complete resolution of clinical signs and synergism of the combination ponesimod-dimethyl fumarate in rat models of multiple sclerosis". Encore poster presented at AAN Apr. 21-27, 2018; Los Angeles, CA.
Pouzol et al., "Therapeutic Potential of Ponesimod Alone and in Combination with Dimethyl Fumarate in Experimental Models of Multiple Sclerosis", Innov Clin Neurosci. Mar. 1, 2019; 16(3-4): pp. 22-30.
Pozzilli C. et al., "Maintenance of efficacy, safety and tolerability of ponesimod in patients with relapsing-remitting multiple sclerosis: phase II extension study", Poster presentation at ECTRIMS (2013) European Committee for Treatment & Research in Multiple Sclerosis—29th Congress.
Rey M. et al., "Desensitization by progressive up-titration prevents first-dose effects on the heart: guinea pig study with ponesimod, a selective S1P1 receptor modulator", PLoS One. Sep. 12, 2013; vol. 8 Issue9, e74285.
Reyes et al., "Effects of Ethnicity and Sex on the Pharmacokinetics and Pharmacodynamics of the Selective Sphingosine-1-Phosphate Receptor 1 Modulator Ponesimod: A Clinical Study in Japanese and Caucasian Subjects", Pharmacology. Nov. 14, 2014; vol. 94 (5-6), pp. 223-229.
Reyes et al., "Effects of ponesimod, a selective S1P1 receptor modulator, on the pharmacokinetics of a hormonal combination contraceptive", Eur J Clin Pharmacol. Mar. 2014, vol. 70(3), pp. 287-293.
Reyes et al., "Mass balance, pharmacokinetics and metabolism of the selective S1P receptor modulator ponesimod in humans", Xenobiotica. Sep. 4, 2014, vol. 45, 1-11.
Scherz et al., Three different up-titration regimens of ponesimod, an S1P1 receptor modulator, in healthy subjects. The Journal of Clinical Pharmacology. Jun. 2015, vol. 55(6), pp. 688-697.
Sobel et al., "FTY720-P activates Sphingosine-1-phosphate receptor 2 and selectively couples to Ga12/13/Rho/ROCK to induce myofibroblast contraction", Mol Pharmacol. Jun. 2015; vol. 87(6), pp. 916-927.
Sobel K. et al., "Sphingosine 1-phosphate (S1P) receptor agonists mediate pro-fibrotic responses in normal human lung fibroblasts via S1P2 and S1P3 receptors and Smad-independent signaling", J Biol Chem. May 24, 2013; vol. 288 (21), pp. 14839-14851.
Vaclavkova et al., "Oral ponesimod in patients with chronic plaque psoriasis: a randomised, double-blind, placebo-controlled phase 2 trial", Lancet. Dec. 6, 2014; vol. 384(9959), pp. 2036-2045. Epub Aug. 10, 2014.
You S. et al., Therapeutic use of a selective S1P1 receptor modulator ponesimod in autoimmune diabetes. PLoS One. Oct. 24, 2013; vol. 8(10): e77296.
Kappos et al., "Ponesimod Compared With Teriflunomide in Patients With Relapsing Multiple Sclerosis in the Active-Comparator Phase 3 OPTIMUM Study : A Randomized Clinical Trial", JAMA Neurology, vol. 78, No. 5, Mar. 29, 2021, pp. 558-567.
Anonymous: "Ponesimod (Oral)", Retrieved from https://web.archive.org/web/20210913052832/https://www.drugs.com/cons/ponesimod.html, Dec. 24, 2020, pp. 1-14.
Anonymous, "Package leaflet: Information for the patient—Ponesimod," Jul. 1, 2021, retrieved from www.medicines.org.uk/emc/files/pil.12799.pdf, Dec. 13, 2022.
Lott et al., "Impact of Demographics, Organ Impairment, Disease, Formulation, and Food on the Pharmacokinetics of the Selective S1P(1) Receptor Modulator Ponesimod Based on 13 Clinical Studies", Clin. Pharmacokinet., Apr. 2017, vol. 56(4), 395-408.
Polman et al., "Diagnostic criteria for multiple sclerosis: 2010 Revisions in the McDonald criteria", Ann. Neurol., 2011, 69(2), 292-302.
The Author(s), published by Elsevier Ltd., "Incidence of switching to second-line antiretroviral therapy and associated factors in children with HIV: an international cohort collaboration", vol. 6, Feb. 2019, e105-e115.
U.S National Library of Medicine: "Oral Ponesimod Versus Teriflunomide in Relapsing Multiple Sclerosis", Apr. 24, 2015, Retrieved from https://clinicaltrials.gov/ct2/show/study/NCT02425644.
Wouters et al., "Pharmaceutical Salts and Co-crystals", RSC Publishing, 2012, pp. 1-9.
Zhang et al., "Ponesimod protects against neuronal death by suppressing the activation of A1 astrocytes in early brain injury after experimental subarachnoid hemorrhage", J. Neurochem., Aug. 2021, 158(4), 880-897, doi: 10.1111/jnc.15457. Epub Jul. 16, 2021.
Anderson, "Teriflunomide Slows Brain vol. Loss in MS", Oct. 21, 2015, pp. 1-3.
Anonymous: "Managing your relapses", MS Society, retrieved from https://www.mssociety.org.uk/care-and-support/resources-and-publications/publications-search/managing-a-relapse-booklet, Nov. 2019, pp. 1-48.
Anonymous: "Package leaflet: Information for the patient—Ponesimod", retrieved from https://www.medicines.org.uk/emc/files/pil. 12799.pdf, retrieved on Jan. 17, 2023, pp. 1-10.
Anonymous: "Ponesimod—Anwendung, Wirkung, Nebenwirkungen | Gelbe Liste", Gelbe Liste , Retrieved from https://www.gelbe-liste.de/wirkstoffe/ Ponesimod_56402, Retrieved on Jan. 10, 2023, pp. 1-5.
Kerr et al., "Barriers to paediatric switching to second-line ART", vol. 6, Feb. 2019, e71-e72.
De Stefano et al., "Establishing Pathological cut-offs of brain atrophy rates in multiple sclerosis", J. Neurol Neurosurg Psychiatry, 2016, vol. 87, pp. 93-99.
Giorgio et al., "Cognition in multiple sclerosis: relevance of lesions, brain atrophy and proton MR spectroscopy," Neurol Sci, vol. 31, Issue 2, 2010, pp. 245-248.
Havrdova et al., "Efficacy and safety of 2 doses of ponesimod (10 and 20 mg o.d.): Interim analysis of a phase II extension trial in relapsing-remitting multiple sclerosi", Oct. 2017—Poster presented; ECTRIMS Online Library, Oct. 27, 2017; Jun. 2008. Abstract No. P1151.
Heinrich et al., "Handbook of Pharmaceutical Salts, Properties, Selection and Use", Wiley-VCH, 2008, pp. 1-3.
Hudgens et al., "Development and Validation of the FSIQ-RMS: A New Patient-Reported questionnaire to Assess Symptoms and Impacts of Fatigue in Relapsing Multiple Sclerosis", Value Health, Apr. 2019, 22(4), 453-466.
Janssen Pharmaceutical Companies of Johnson & Johnson, "New Head-to-Head Phase 3 Study Data Show Ponesimod Superiority Versus Aubagio (teriflunomide) 14mg in Adults with Relapsing Multiple Sclerosis (MS)", Sep. 11, 2019, pp. 1-6.
Janssen Showcases Recent Data in Relapsing Multiple Sclerosis at the 2021 European Committee for Treatment and Research in Multiple Sclerosis Congress, CISION PR Newswire, retrieved from https://www.prnewswire.com/news-releases/janssen-showcases-recent-data-in-relapsing-multiple-sclerosis-at-the-2021-european-committee-for-treatment-and-research-in-multiple-sclerosis-congress-301387378.html, Sep. 29, 2021, pp. 1-13.
Juif et al., "Biocomparison of three formulations of the S1P1 receptor modulator ponesimod in healthy subjects", Drugs in R&D., Jun. 2015, 15(2), 203-210.
Juif et al., "Clinical pharmacology, efficacy, and safety aspects of sphingosine-1-phosphate receptor modulators", Expert Opin. Drug Metab. Toxicol., Aug. 2016, vol. 12(8), 879-895. Epub. Jun. 13, 2016.
Juif et al., "Mitigation of Initial Cardiodynamic Effects of the S1P1 Receptor Modulator Ponesimod Using a Novel Up-Titration Regimen", Journal of Clinical Pharmacology, 2016, vol. 57(3), 401-410.
Kappos et al., "Effect of oral ponesimod on clinical disease activity and MRI-based outcomes in patients with relapsing multiple sclerosis: Phase 3 OPTIMUM study," Multiple sclerosis journal, vol. 26, 2020, pp. 151-152.
Kappos et al., "The POINT study: a randomized, double-blind, parallel-group, add-on, superiority phase 3 study to compare the efficacy and safety of ponesimod to placebo in subjects with active relapsing multiple sclerosis who are treated with dimethyl fumarate", Poster presented at ECTRIMS (European Committee for Treatment

(56) References Cited

OTHER PUBLICATIONS and Research in Multiple Sclerosis), Citation for abstract: ECTRIMS Online Library, Oct. 10, 2018, 228412. Abstract No. P568.
Keown, "Janssen's Ponesimod Finds Success in Head-to-Head Multiple Sclerosis Trial", Jul. 26, 2019, pp. 1-4.
Kihara et al., "Ponesimod inhibits astrocyte-mediated neuroinflammation and protects against cingulum demyelination via S1P1-selective modulation," SAGE Publications Abstracts Multiple Sclerosis Journal, Oct. 1, 2021, 1-13.
Lebert et al., "Highly Functional Virus-Specific Cellular Immune Response in Asymptomatic SARS-CoV-2 infection", J. Exp. Med., 2021, vol. 218, No. 5, e20202617, pp. 1-17.
Cosman et al. High-Dose Glucocorticoids in Multiple Sclerosis Patients Exert Direct Effects on the Kidney and the Skeleton, Journal of Bone and Mineral Research, 7, p. 1097-1105. (Year: 1994).
Olsson et al., Oral ponesimod in relapsing-remitting multiple sclerosis: a randomised phase II trial, J Neurol Neurosurg Psychiatry, 85, p. 1198-1209. (Year: 2014).
Olsson et al., "Correction: oral ponesimod in relapsing-remitting multiple sclerosis: a randomised phase II trial", J Neurol Neurosurg Psychiatry, 2019, vol. 90, pp. e7.
Oral Ponesimod Versus Teriflunomide In Relapsing Multiple Sclerosis (OPTIMUM); Results Posted Tab—Study Reg. Dates: First Submitted Apr. 21, 2015; https://clinicaltrials.gov/study/NCT02425644?tab=results, Retrieved from https://clinicaltrials.gov/study/NCT02425644?tab=results on A[ril 10, 2025 by Exmr.D. M. Willis.
Achiron et al., "COVID-19 Vaccination in Patients with Multiple Sclerosis: What We have Learnt by Feb. 2021", Multiple Sclerosis Journal, Apr. 15, 2021, vol. 27, No. 6, pp. 864-870.
Achiron et al., "Humoral Immune Response to COVID-19 mRNA Vaccine in Patients with Multiple Sclerosis Treated with High-Efficacy Disease-Modifying Therapies", Ther. Adv. Neurol. Disord., 2021, vol. 14, pp. 1-8.
D'Ambrosio et al., "Therapeutic Advances in Chronic Disease Ponesimod, a selective SIPI receptor modulator: a potential treatment for multiple sclerosis and other immune-mediated diseases", Ther Adv Chronic Dis., Jan. 2016, vol. 7, No. 1, pp. 18-33.
FDA, "Determining Whether to Submit an ANDA or a 505(b)(2) Application Guidance for Industry", U.S. Department of Health and Human Services, Oct. 2017, pp. 1-14.
Freedman, "Teriflunomide in relapsing multiple sclerosis: therapeutic utility", Therapeutic Advances in Chronic Disease, 2013, vol. 4, No. 5, pp. 192-205.
Janssen Pharmaceutical Companies, "Ponvory (ponesimod) tablets, for oral use", 2021, pp. 1-34.
Ufer et al., "Impact of siponimod on vaccination response in a randomized, placebo-controlled study", 2017, 1-9.
Boehler et al., "Absolute Bioavailability of Ponesimod, a Selective S1P1 Receptor Modulator, in Healthy Male Subjects", European Journal of Drug Metabolism and Pharmacokinetics 2017, vol. 42(1), pp. 129-134.
Bolli M.H et al., "2-imino-thiazolidin-4-one derivatives as potent, orally active S1P1 receptor agonists", J Med Chem. May 27, 2010, vol. 53(10), pp. 4198-4211.
Brossard P. et al., "Multiple-dose tolerability, pharmacokinetics, and pharmacodynamics of ponesimod, an S1P receptor modulator: Favorable impact of dose up-titration", J Clin Pharmacol. 2014; vol. 54(2), pp. 179-188.
Brossard P. et al., "Pharmacokinetics and pharmacodynamics of ponesimod, a selective S1P1 receptor modulator, in the first-in-human study", Br J Clin Pharmacol. Dec. 2013; 76(6), pp. 888-896.
Cohen et al., "Mechanisms of fingolimod's efficacy and adverse effects in multiple sclerosis", Ann Neurol 2011; vol. 69(5), pp. 759-777.
Cohen et al., "Oral fingolimod or intramuscular interferon for relapsing multiple sclerosis", N Engl J Med; vol. 362(5), pp. 402-415; 2010.
Confavreux et al., "Oral teriflunomideforpatients with relapsing multiple sclerosis (TOWER): a randomised, double-blind, placebo-controlled, phase 3 trial", Lancet Neurol., 2014, vol. 13, No. 3, pp. 247-256.
D'Ambrosio et al., "Differential effects of ponesimod, a selective S1P1 receptor modulator, on blood-circulating human T cell subpopulations", Immunopharmacol Immunotoxicol. 2015 ; vol. 37(1):103-9.
European Medicines Agency, Guideline on clinical investigation of medicinal products for the treatment of Multiple Sclerosis, Mar. 26, 2015, EMA/CHMP/771815, Rev. 2, Committee for Medicinal Products for Human Use (CHMP).
Gatfield et al., "Sphingosine-1-Phosphate (S1P) Displays Sustained S1P Receptor Agonism and Signaling through S1P Lyase-dependent Receptor Recycling", Cell Signal. Jul. 2014; vol. 26(7), pp. 1576-1588.

* cited by examiner

☐ 0 No difficulty

☐ 1 A little difficulty

☐ 2 Moderate difficulty

☐ 3 Quite a bit of difficulty

☐ 4 Extreme difficulty

FIG. 38

☐ 0 No difficulty

☐ 1 A little difficulty

☐ 2 Moderate difficulty

☐ 3 Quite a bit of difficulty

☐ 4 Extreme difficulty

FIG. 39

| | | |
|---|---|---|
| ☐ | 0 | No difficulty |
| ☐ | 1 | A little difficulty |
| ☐ | 2 | Moderate difficulty |
| ☐ | 3 | Quite a bit of difficulty |
| ☐ | 4 | Extreme difficulty |

FIG. 40

☐ 0 Not difficult

☐ 1 A little difficult

☐ 2 Moderately difficult

☐ 3 Quite difficult

☐ 4 Extremely difficult

FIG. 41

☐ 0 No difficulty

☐ 1 A little difficulty

☐ 2 Moderate difficulty

☐ 3 Quite a bit of difficulty

☐ 4 Extreme difficulty

FIG. 42

| | |
|---|---|
| ☐ 0 | No difficulty |
| ☐ 1 | A little difficulty |
| ☐ 2 | Moderate difficulty |
| ☐ 3 | Quite a bit of difficulty |
| ☐ 4 | Extreme difficulty |

FIG. 43

| | | |
|---|---|---|
| ☐ | 0 | No difficulty |
| ☐ | 1 | A little difficulty |
| ☐ | 2 | Moderate difficulty |
| ☐ | 3 | Quite a bit of difficulty |
| ☐ | 4 | Extreme difficulty |

FIG. 44

☐ 0 No difficulty
☐ 1 A little difficulty
☐ 2 Moderate difficulty
☐ 3 Quite a bit of difficulty
☐ 4 Extreme difficulty

FIG. 45

| | |
|---|---|
| ☐ 0 | Not at all |
| ☐ 1 | A little bit |
| ☐ 2 | Somewhat |
| ☐ 3 | Quite a bit |
| ☐ 4 | Extremely |

FIG. 46

☐ 0 Never

☐ 1 Rarely

☐ 2 Some of the time

☐ 3 Most of the time

☐ 4 Almost all of the time

FIG. 47

| | |
|---|---|
| ☐ 0 | Never |
| ☐ 1 | Rarely |
| ☐ 2 | Some of the time |
| ☐ 3 | Most of the time |
| ☐ 4 | Almost all of the time |

FIG. 48

| | |
|---|---|
| ☐ 0 | Never |
| ☐ 1 | Rarely |
| ☐ 2 | Some of the time |
| ☐ 3 | Most of the time |
| ☐ 4 | Almost all of the time |

FIG. 49

☐ 0 Never

☐ 1 Rarely

☐ 2 Some of the time

☐ 3 Most of the time

☐ 4 Almost all of the time

FIG. 50

METHODS OF TREATING MULTIPLE SCLEROSIS

CROSS-REFERENCE TO RELATED APPLICATIONS

This application claims the benefit of U.S. Provisional Patent Application No. 63/254,410, filed Oct. 11, 2021, the disclosure of which is incorporated by reference herein.

TECHNICAL FIELD

The present disclosure relates to methods of treating multiple sclerosis.

BACKGROUND

Multiple sclerosis (MS) is a chronic autoimmune inflammatory disease of the central nervous system affecting approximately 2.5 million people worldwide. The disease is clinically perceived by relapses and progressive loss of neurological function, primarily attributed to demyelination, axonal loss, leading to neurological impairment and severe disability. The two main subtypes of MS are relapsing forms of MS (RMS) which represent 85% of MS patients and include relapsing-remitting disease (RRMS), clinically isolated syndrome, and active secondary progressive disease; and primary progressive MS (PPMS) which affects only 15% of MS patients.

Relapses are defined as newly appearing neurological symptoms in the absence of fever or infections that last for more than 24 hours. Relapses may fully recover over days or weeks or lead to persistent residual deficits and accumulation of disability.

The natural history of MS is usually divided into two partially overlapping phases, a predominantly inflammatory phase and a predominantly degenerative phase: after an initial phase of relapsing remitting MS, driven by inflammatory mechanism, patients experience a secondary progressive MS characterized by continuous worsening of symptoms independent of the occurrence of relapses, the degenerative phase of MS. Most currently available disease-modifying treatments (DMTs) address the inflammatory phase of MS and are less efficacious in the degenerative phase.

Current medical practice encourages early intervention with disease-modifying treatments, with the intent of optimizing long-term clinical outcomes.

Key objectives in the management of MS are reducing the rate of relapses and preventing or at least delaying disease progression. Most of the disease-modifying drugs approved for MS have to be administered by injection or infusion (subcutaneous [s.c.], intramuscular [i.m.], or intravenous [i.v.] route). Recently, new disease-modifying drugs administered orally have been approved for RMS.

The following injectable drugs have been approved in at least one country for the treatment of MS:

- Interferon (IFN) β-1a 30 mcg i.m. once weekly (Avonex®)
- IFN β-1a 22 or 44 mcg s.c. 3 times weekly (Rebif®)
- IFN β-1b 250 mcg s.c. every other day (Betaferon®, Extavia®)
- Pegylated IFN β-1a 125 mcg subcutaneously every 2 weeks (Plegridy®)
- Glatiramer acetate 20 mg s.c. once a day (o.d.) or 40 mg subcutaneously 3 times weekly (Copaxone®)
- Glatiramer acetate 20 mg s.c. o.d. (Glatopa®)
- Natalizumab 30) mg i.v. every 4 weeks (Tysabri®)
- Mitoxantrone i.v. every 3 months (Novantrone®)
- Alemturumab concentrate for solution for infusion, 12 mg alemtuzumab in 1.2 mL (10 mg/mL) (Lemtrada®)

Several oral drugs have also been approved for MS:

- Fingolimod 0.5 mg orally o.d. (Gilenya®)
- Teriflunomide 7 mg, 14 mg o.d. (Aubagio®)
- Dimethyl fumarate (BG-12) gastro-resistant hard capsules 120/240 mg twice daily (Tecfidera®))
- Cladribine 40 to 100 mg orally per treatment week (Mavenclad®)

Sphingosine-1-phosphate (SIP) plays a central role in lymphocyte trafficking. SIP is synthesized and secreted by many cell types, including platelets, erythrocytes, and mast cells, and elicits a variety of physiological responses. Lymphocyte egress from primary and secondary lymphoid organs is dependent on the S1P1 receptor. S1P1 receptor modulators block lymphocyte migration out of lymphoid tissue into the lymphatic and vascular circulation, thereby reducing peripheral lymphocyte counts and preventing lymphocyte recruitment to sites of inflammation. Following withdrawal of an S1P1 receptor agonist, the functional lymphocytes return to the circulation from their sites of sequestration. Other functions that do not rely on homing mechanisms, such as antibody generation by B lymphocytes, first-line immunological protection by granulocytes and monocytes, and antigen-dependent T-cell activation and expansion, are not affected by this mechanism.

SIP itself induces pleiotropic effects, which are mediated by a family of five G protein-coupled receptors. S1P1-S1P5, located on endothelial cells, vascular and cardiac smooth muscle cells, and cardiac myocytes. The first SIP receptor modulator, fingolimod (FTY720, Gilenya®), which has been approved by the FDA and the EMA for the treatment of MS, is not selective for the S1P1 receptor but interacts with S1P3, S1P4, and S1P5.

Ponesimod, an iminothiazolidinone derivative, is an orally active, selective modulator of the S1P1 that induces a rapid, dose-dependent, and reversible reduction in peripheral blood lymphocyte count by blocking the egress of lymphocytes from lymphoid organs. T and B cells are most sensitive to ponesimod mediated sequestration. In contrast, monocyte, natural killer (NK) cell and neutrophil counts are not reduced by ponesimod. Ponesimod is commercially available as PONVORY™, a once-daily oral medication. In the United States the Food and Drug Administration (FDA) has approved PONVORY™ to treat adults with relapsing forms of multiple sclerosis (MS), to include clinically isolated syndrome, relapsing-remitting disease, and active secondary progressive disease.

Early treatment in multiple sclerosis with higher-potency therapies can improve longer-term outcomes. Accordingly, there is a need for therapies that provide an increased clinical benefit to a patient population with early onset multiple sclerosis.

SUMMARY

In some aspects, the disclosure is directed to methods of treating early-stage multiple sclerosis (ESMS) in a patient, comprising administering ponesimod to the patient using a regimen that is effective to treat the ESMS. Early-stage multiple sclerosis (ESMS) may also be referred to as low-disability multiple sclerosis (LDMS).

In other aspects, the disclosure is directed to methods of reducing the number of combined unique active lesions (CUALs) in a patient suffering from early-stage multiple sclerosis (FSMS), comprising administering ponesimod to the patient using a regimen that is effective to reduce the number of CUALs relative to a patient population at substantially the same level of disease progression receiving a standard of care treatment that does not comprise ponesimod.

In further aspects, the disclosure is directed to methods of reducing annualized relapse rate (ARR) in a patient suffering from early-stage multiple sclerosis (ESMS), comprising administering ponesimod to the patient using a regimen that is effective to reduce the ARR relative to a patient population at substantially the same level of disease progression receiving a standard of care treatment that does not comprise ponesimod.

In other aspects, the disclosure is directed to methods of reducing MS-fatigue mean difference in a patient suffering from early-stage multiple sclerosis (ESMS), comprising administering ponesimod to the patient using a regimen that is effective to reduce MS-fatigue mean difference relative to a patient population at substantially the same level of disease progression receiving a standard of care treatment that does not comprise ponesimod.

In some aspects, the disclosure is directed to ponesimod for use in methods of treating early-stage multiple sclerosis (ESMS) in a patient in need thereof, wherein said methods comprise administrating ponesimod to the patient using a regimen that is effective to treat the ESMS.

In other aspects, the disclosure is directed to ponesimod for use in methods of reducing the number of combined unique active lesions (CUALs) in a patient suffering from early-stage multiple sclerosis (ESMS), wherein said methods comprise administrating ponesimod to the patient using a regimen that is effective to reduce the number of CUALs relative to a patient population at substantially the same level of disease progression receiving a standard of care treatment that does not comprise ponesimod.

In further aspects, the disclosure is directed to ponesimod for use in methods of reducing annualized relapse rate (ARR) in a patient suffering from early-stage multiple sclerosis (ESMS), wherein said methods comprise administrating ponesimod to the patient using a regimen that is effective to reduce the ARR relative to a patient population at substantially the same level of disease progression receiving a standard of care treatment that does not comprise ponesimod.

In other aspects, the disclosure is directed to ponesimod for use in methods of reducing MS-fatigue mean difference in a patient suffering from early-stage multiple sclerosis (ESMS), wherein said methods comprise administrating ponesimod to the patient using a regimen that is effective to reduce MS-fatigue mean difference relative to a patient population at substantially the same level of disease progression receiving a standard of care treatment that does not comprise ponesimod.

In some aspects, the disclosure is directed to use of ponesimod for the manufacture of a medicament for the treatment of early-stage multiple sclerosis (ESMS) in a patient, wherein said medicament is adapted to be administered using a regimen that is effective to treat the ESMS.

In other aspects, the disclosure is directed to use of ponesimod for the manufacture of a medicament for reducing the number of combined unique active lesions (CUALs) in a patient suffering from early-stage multiple sclerosis (ESMS), wherein said medicament is adapted to be administered using a regimen that is effective to reduce the number of CUALs relative to a patient population at substantially the same level of disease progression receiving a standard of care treatment that does not comprise ponesimod.

In further aspects, the disclosure is directed to use of ponesimod for the manufacture of a medicament for reducing annualized relapse rate (ARR) in a patient suffering from early-stage multiple sclerosis (ESMS), wherein said medicament is adapted to be administered using a regimen that is effective to reduce the ARR relative to a patient population at substantially the same level of disease progression receiving a standard of care treatment that does not comprise ponesimod.

In other aspects, the disclosure is directed to use of ponesimod for the manufacture of a medicament for reducing MS-fatigue mean difference in a patient suffering from early-stage multiple sclerosis (ESMS), wherein said medicament is adapted to be administered using a regimen that is effective to reduce MS-fatigue mean difference relative to a patient population at substantially the same level of disease progression receiving a standard of care treatment that does not comprise ponesimod.

In certain aspects, the disclosure is directed to a pharmaceutical product comprising ponesimod, wherein the pharmaceutical product is packaged and the package includes instructions for administering ponesimod to a patient having early-stage multiple sclerosis (ESMS) in a regimen that is effective to treat the ESMS.

BRIEF DESCRIPTION OF THE DRAWINGS

In FIG. 2A, n(Pon)=No. of subjects in ponesimod arm; rate (Pon) mean rate in ponesimod arm; n(Ter)=No. of subjects in teriflunomide arm; and rate(Ter) mean rate in teriflunomide arm. *=Conducted on the Per Protocol Set; =Relapses with missing EDSS are imputed as confirmed relapses.

In FIG. 3A, subjects with available baseline and at least one post-baseline result are included in the analysis, whereby MMRM=mixed effects repeated measurements model with unstructured covariance, treatment, visit, treatment by visit interaction, baseline by visit interaction as fixed effects, baseline FSIQ score, EDSS strata (<=3.5, >3.5), DMT in last 2 years prior randomization strata (Y,N) as covariates.

In FIG. 4, an event=12 week CDA and subjects without event are censored at their last EDSS assessment without EDSS increase. Unstratified Kaplan-Meier estimates are presented. Bars on graph display pointwise 95% confidence intervals of the estimate. P-value is two-sided and based on the stratified log-rank test. Hazard ratio estimate obtained from stratified Cox regression with Wald confidence limits. Analysis is stratified by EDSS strata (≤3.5; >3.5) and disease modifying therapy in last 2 years prior to randomization strata (Y,N).

In FIG. 5, an event=24 week CDA and subjects without event are censored at their last EDSS assessment without EDSS increase. Unstratified Kaplan-Meier estimates are presented. Bars on graph display pointwise 95% confidence intervals of the estimate. P-value is two-sided and based on the stratified log-rank test. Hazard ratio estimate obtained from stratified Cox regression with Wald confidence limits. Analysis is stratified by EDSS strata (≤3.5; >3.5) and disease modifying therapy in last 2 years prior to randomization strata (Y,N).

In FIG. 7, n(Pon)=subjects in ponesimod group; rate(Pon)=annualized relapse rate in ponesimod group; n(Ter)=subjects in teriflunomide group and rate(Ter)=annualized relapse rate in teriflunomide group. The vertical solid line references the treatment effect from the main analysis. Negative binomial model is applied with Wald confidence limits, offset: log time (years) up to EOS. The main analysis is adjusted for the following covariates: EDSS strata (≤3.5; >3.5); DMT in last 2 years prior to randomization strata (Y,N); and number of relapses in year prior to study entry (≤1; ≥2).

In FIG. 8, p*=interaction p-value; n(Pon)=no. of subjects in ponesimod group; rate(Pon)=mean rate in ponesimod group; n(Ter)=no. of subjects in teriflunomide group and rate(Ter)=mean rate in teriflunomide group. Negative binomial model is applied with Wald confidence limits, offset: log time (years) up to EOS, in each subgroup separately. Interaction p-value is from likelihood ratio test of interaction term in model with treatment, subgroup and treatment by subgroup interactions. The vertical solid line references the treatment effect from the main analysis. The main analysis is adjusted for the following covariates: EDSS strata (≤3.5; >3.5); DMT in last 2 years prior to randomization strata (Y,N); and number of relapses in year prior to study entry (≤1; ≥2). Analyses in subgroups are not adjusted for covariates.

FIGS. 31-50 show questionnaire information.

DETAILED DESCRIPTION OF ILLUSTRATIVE EMBODIMENTS

Figure 1:
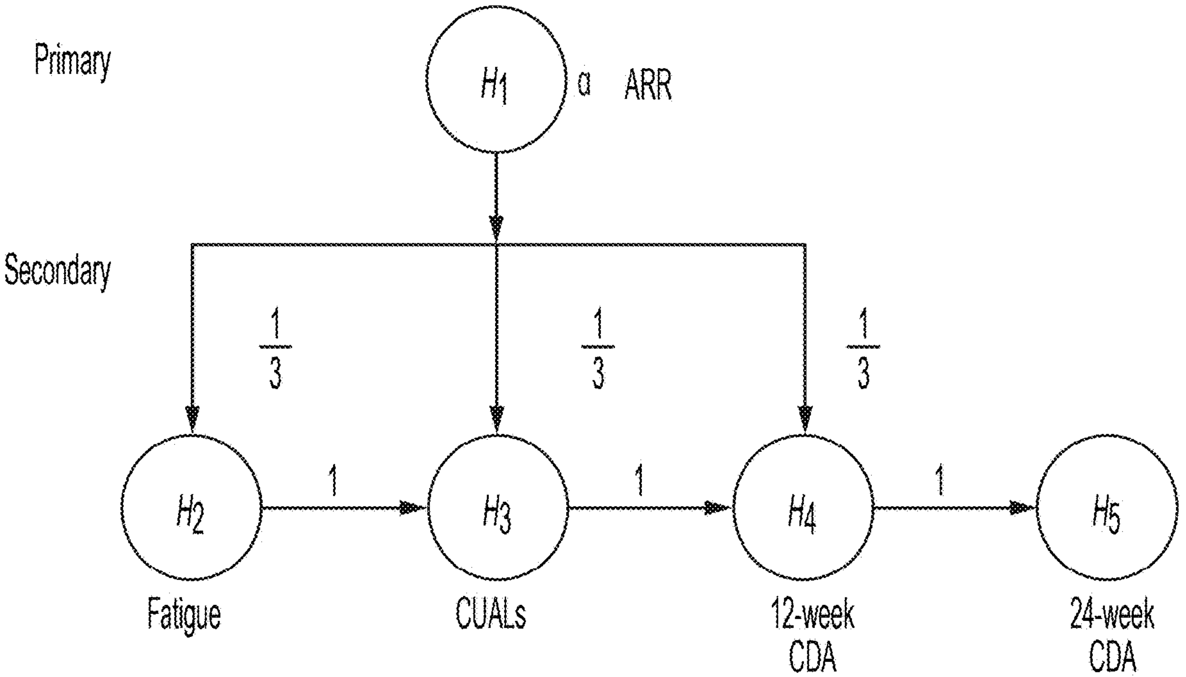
FIG. 1 shows the testing strategy for the study described in Example 1.

In the present disclosure the singular forms "a", "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C." "B or C," or "A, B, or C."

It is to be appreciated that certain features of the disclosure which are, for clarity, described herein in the context of separate embodiments, may also be provided in combination in a single embodiment. That is, unless obviously incompatible or excluded, each individual embodiment is deemed to be combinable with any other embodiments and such a combination is considered to be another embodiment. Conversely, various features of the disclosure that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely." "only" and the like in connection with the recitation of claim elements, or use of a "negative" limitation. Finally, while an embodiment may be described as part of a series of steps or part of a more general structure, each said step may also be considered an independent embodiment in itself.

It should be understood that references herein to methods of treatment (e.g., methods for treating early-stage multiple sclerosis (ESMS) in a patient in need thereof, comprising administering ponesimod to the patient using a regimen that is effective to treat the ESMS, should also be interpreted as references to:

- ponesimod or formulations thereof for use in methods of treatment (e.g., methods for treating early-stage multiple sclerosis (ESMS) in a patient in need thereof); and/or
- the use of ponesimod or formulations thereof in the manufacture of a medicament for treating early-stage multiple sclerosis (ESMS) in a patient in need thereof.

In some aspects, the present disclosure is directed to methods of avoiding worsening of fatigue-related symptoms in a human patient suffering from multiple sclerosis and fatigue, comprising, optionally, assessing the fatigue-related symptoms of the patient; and administering an effective regimen of ponesimod to the patient, wherein the regimen is sufficient to avoid worsening of the fatigue-related symptoms. As described herein, fatigue is fatigue associated with multiple sclerosis.

In certain aspects, the methods are directed to patients that have had no prior disease modifying treatment (DMT) for multiple sclerosis within about two years prior to initiation of treatment with ponesimod. In some embodiments, the methods are directed to patients that have a baseline expanded disability status scale (EDSS) score of ≤3.5, more particularly ≤3.0, prior to initiation of treatment with ponesimod. In other embodiments, the methods are directed to patients that have no Gd+/T1 lesions prior to initiation of treatment with ponesimod.

In other aspects, the present disclosure is directed to methods of reducing the number of combined unique active lesions (CUALs) in a patient suffering from multiple sclerosis, comprising administering an effective regimen of ponesimod to the patient, wherein the regimen is sufficient to reduce the number of CUALs by at least 40% relative to a patient population at substantially the same level of disease progression receiving a standard of care treatment that does not comprise ponesimod.

In other aspects, the present disclosure is directed to methods of reducing the annualized relapse rate (ARR) in a patient suffering from multiple sclerosis, comprising administering ponesimod to the patient using a regimen that is effective to reduce the ARR relative to a patient population at substantially the same level of disease progression receiving a standard of care treatment that does not comprise ponesimod.

In some aspects, the methods of the disclosure are performed on a human patient suffering from multiple sclerosis. In some embodiments, the patient's multiple sclerosis is relapsing multiple sclerosis. In other embodiments, the relapsing multiple sclerosis comprises relapsing-remitting disease, clinically isolated syndrome, or active secondary progressive disease.

As used herein, the term "avoiding worsening of fatigue-related symptoms" refers to preventing the patient's fatigue-related symptoms from becoming worse relative to the patient's fatigue-related symptoms at baseline, wherein baseline refers to a time period prior to initiation of treatment with ponesimod. This time period is typically up to about 45 days prior to initiation of treatment with ponesimod, including, for example, up to about 40 days, up to about 35 days, up to about 30 days, up to about 25 days, up to about 20 days, up to about 15 days, or up to about 10 days prior to initiation of treatment with ponesimod. By avoiding worsening, the methods otherwise relate to stabilizing or improving fatigue-related symptoms.

In some embodiments of the methods of the disclosure, the patient's fatigue-related symptoms are assessed. In some embodiments of the methods of the disclosure, the patient's fatigue-related symptoms are not assessed prior to initiation of treatment with ponesimod. As used herein, "fatigue-related symptoms" refer to symptoms of fatigue experienced by the patient.

In some aspects, the fatigue-related symptoms are symptoms experienced by the patient while doing routine daily activities (e.g. housework, yard work, shopping, working). In some embodiments, the fatigue-related symptoms are those experienced by the patient while doing routine daily activities and include being physically tired, being mentally tired, being physically weak, lacking energy, feeling worn out, or feeling sleepy.

In other embodiments, the fatigue-related symptoms are (1) being physically tired, (2) being mentally tired, (3) being physically weak, (4) lacking energy, (5) feeling worn out, (6) feeling sleepy while doing routine daily activities, and (7) feeling worn out while at rest.

In some embodiments, the patient's fatigue-related symptoms are assessed before initiation of ponesimod administration, for example, at baseline. In other embodiments, the patient's fatigue-related symptoms are assessed after initiation of ponesimod administration to, for example monitor the fatigue-related symptoms during the treatment with ponesimod. In some embodiments, the patient's fatigue-related symptoms are assessed both before initiation of ponesimod administration and after initiation of ponesimod therapy.

The patient's fatigue-related symptoms may be assessed by ascertaining from the patient the nature and severity of any symptoms of fatigue experienced by the patient. In some embodiments, the patient's fatigue-related symptoms are assessed using a patient-reported outcome (PRO) questionnaire.

Figure 2A:
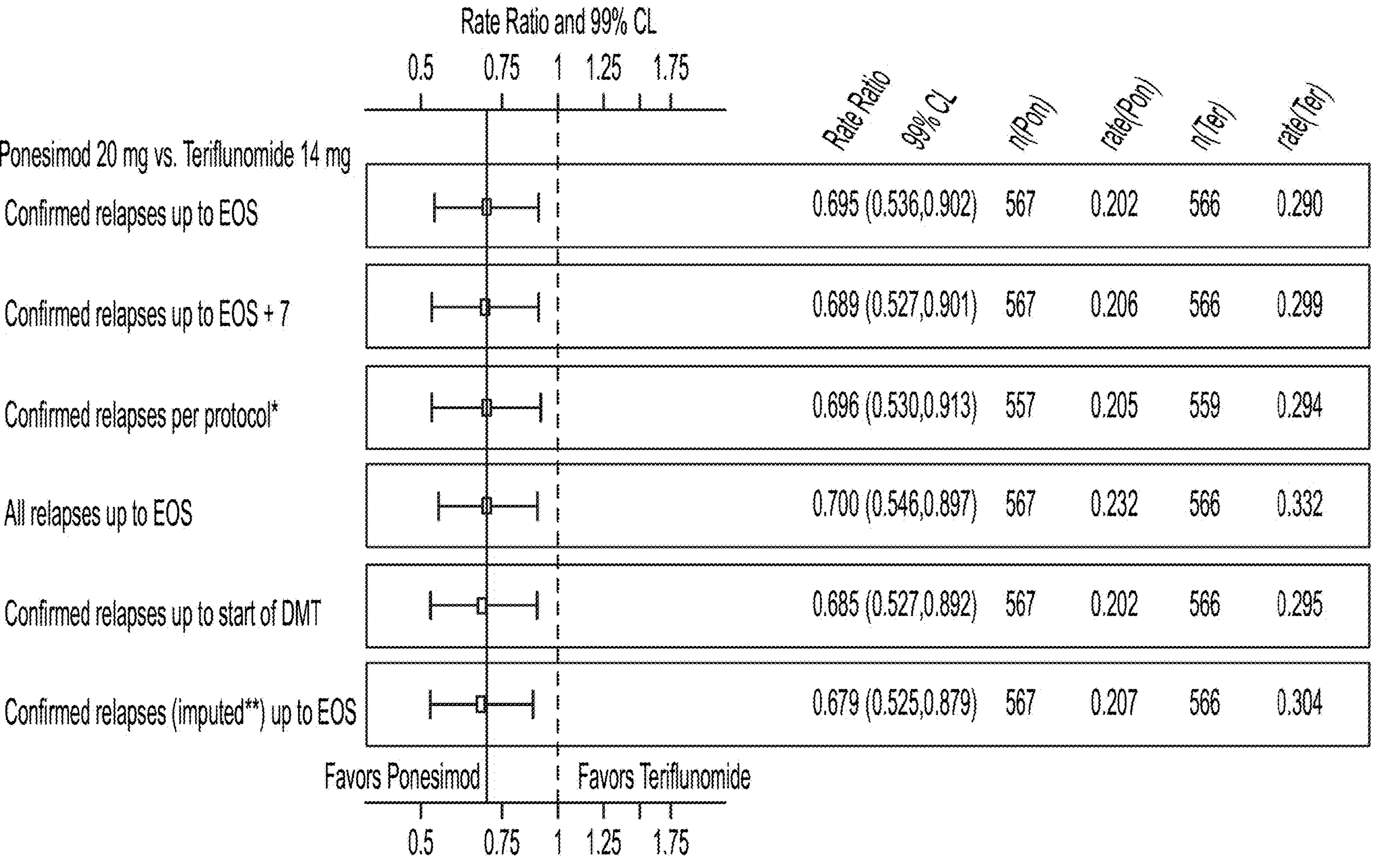
FIG. 2A shows an overview of primary and main supplementary analyses of relapses (Forest plot with 99% CL).
Figure 2B:
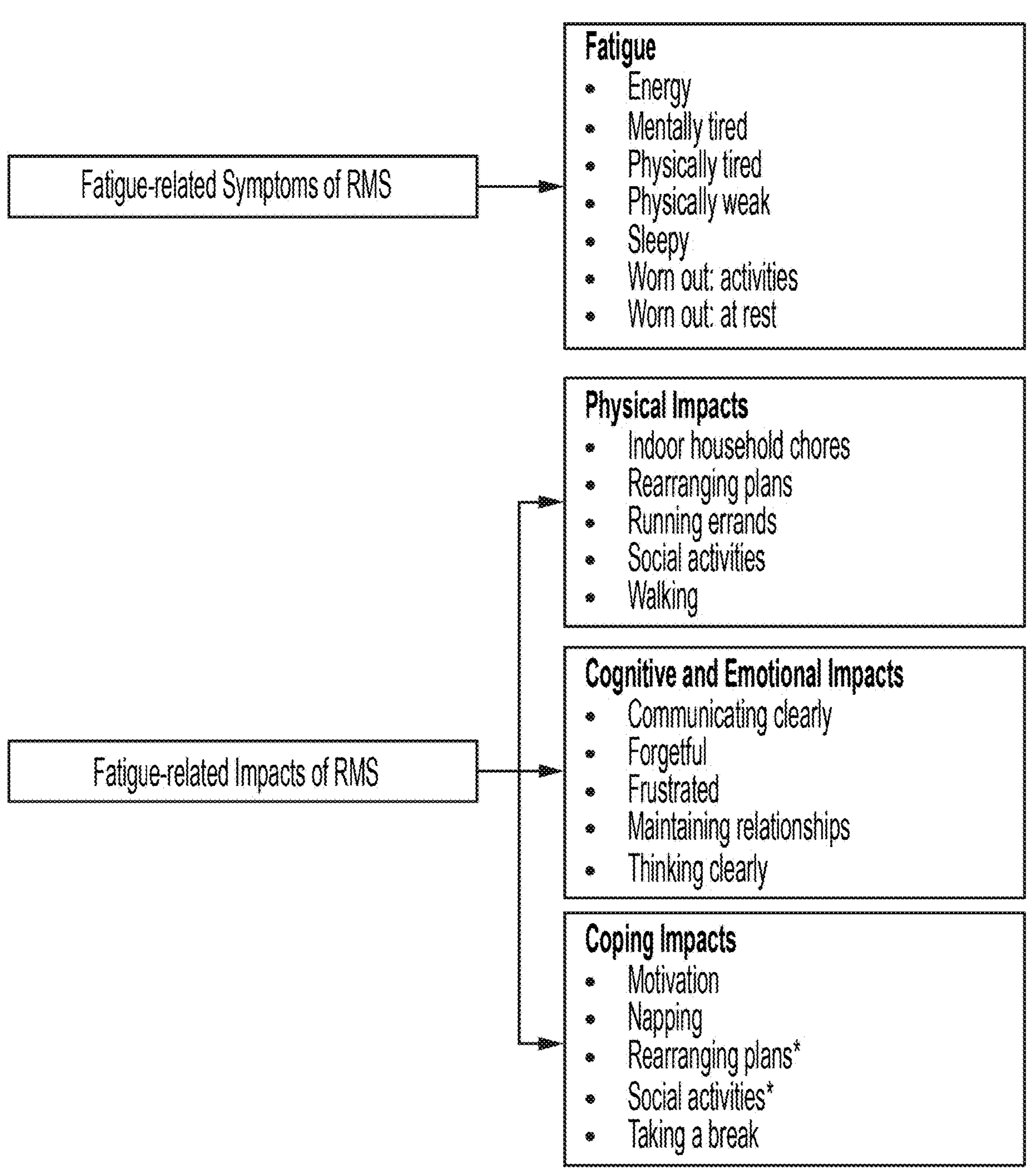
FIG. 2**B shows the conceptual framework for the Fatigue Symptoms and Impact Questionnaire—Relapsed Multiple Sclerosis (FSIQ-RMS); *=items also present in physical impacts subdomain.

In some embodiments, the patient-reported outcome questionnaire is the Fatigue Symptoms and Impact Questionnaire—Relapsing Multiple Sclerosis (FSIQ-RMS) (available from Mapi Research Trust). The FSIQ-RMS is an MS specific 20-item PRO measure that comprises 2 domains: one measuring MS symptoms and one measuring MS-related impacts. See Hudgens S, et al., *Development and Validation of the FSIQ-RMS: A New Patient-Reported Questionnaire to Assess Symptoms and Impacts of Fatigue in Relapsing Multiple Sclerosis. Value Health.* 2019 April; 22(4):453-466. doi: 10.1016/j.jval.2018.11.007. Epub 2019 Feb. 21. PubMed PMID: 30975397. With 7 symptom items and 13 impact items (in 3 impacts subdomains: physical, cognitive and emotional, and coping), the FSIQ-RMS is a comprehensive, valid, and reliable measure of fatigue-related symptoms and impacts in RMS patients. FIG. 2B depicts a conceptual framework for the FSIQ-RMS.

In some embodiments, the patient-reported outcome questionnaire is the symptom domain of the FSIQ-RMS. The FSIQ-RMS symptom domain (FSIQ-RMS-S) consists of seven items assessing fatigue-related symptoms with a recall period of 24 hours measured on an 11-point numeric rating scale; the standardized symptom domain score ranges from 0 to 100 with a higher score indicating greater fatigue. This domain (i.e., section 1 of the questionnaire) is completed on 7 consecutive days.

The FSIQ-RMS impact domain (FSIQ-RMS-1) consists of 13 items assessing impacts of fatigue-related symptoms with a recall period of 7 days measured on a 5-point verbal descriptor scale, the standardized impact domain score ranges from 0 to 100 with a higher score indicating greater impact.

In some aspects of the methods of the present disclosure, the patient is administered an effective regimen of ponesimod. An effective regimen is one that elicits the biological or medicinal response in a human tissue system that is being sought by a researcher, medical doctor, or other clinician, which includes alleviation of one or more symptoms of the disease or disorder being treated.

As used herein, the term "ponesimod" refers to the compound (R)-5-[3-chloro-4-(2,3-dihydroxy-propoxy)-benz[Z]ylidene]-2-([Z]-propylimino)-3-o-tolyl-thiazolidin-4-one, which has the following structure:

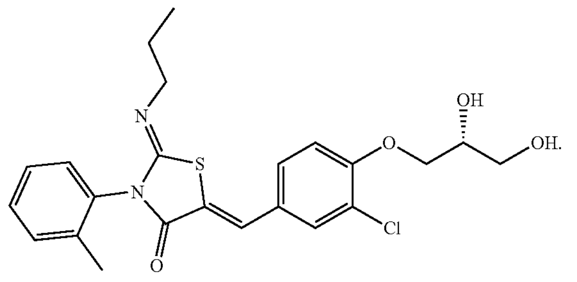 [SMILES: CCC/N=C1\S/C(=C\c2ccc(OC[C@H](O)CO)c(Cl)c2)C(=O)N1c1ccccc1C]

In some embodiments, "ponesimod" also refers to pharmaceutically acceptable salts of ponesimod. The term "pharmaceutically acceptable salt" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example Handbook of Pharmaceutical Salts. Properties, Selection and Use, P. Heinrich Stahl, Camille G. Wermuth (Eds.), Wiley-VCH. 2008 and Pharmaceutical Salts and Co-crystals, Johan Wouters and Luc Quéré (Eds.), RSC Publishing, 2012.

It is to be understood that the present disclosure encompasses ponesimod in any form including amorphous as well as crystalline forms. It is further to be understood that crystalline forms of ponesimod encompasses all types of crystalline forms including polymorphs, solvates and hydrates, salts and co-crystals (when the same molecule can be co-crystallized with different co-crystal formers) provided they are suitable for pharmaceutical administration. In some embodiments, ponesimod is in crystalline form A or crystalline form C as described in WO 2010/046835, incorporated herein by reference. In some embodiments, ponesimod is in crystalline form C.

It should be noted that the amounts of ponesimod described herein are set forth on a ponesimod free base basis. That is, the amounts indicate that amount of the ponesimod molecule administered, exclusive of, for example, solvent (such as in solvates) or counterions (such as in pharmaceutically acceptable salts).

In some embodiments, the effective regimen comprises a daily dose of ponesimod. In some embodiments, the daily dose of ponesimod is administered orally.

In some embodiments, the daily dose of ponesimod is administered once daily.

In some embodiments, the daily dose of ponesimod is about 15 to about 25 mg. In further embodiments, the daily dose of ponesimod is about 15 mg, about 16 mg, about 17 mg, about 18 mg, about 19 mg, about 20 mg, about 21 mg, about 22 mg, about 23 mg, about 24 mg, or about 25 mg. In certain embodiments, the daily dose of ponesimod is about 20 mg.

In some embodiments, about 20 mg of ponesimod is administered orally once daily.

In other embodiments, the effective regimen comprises an up-titration, followed by a daily maintenance dose of ponesimod. An up-titration is a dosing procedure in which the daily dose of ponesimod is gradually increased over a period of days, culminating with administration of the maintenance dose.

In some embodiments, the regimen comprises an up-titration at the initiation of the method of the disclosure. In other embodiments, the regimen comprises an up-titration upon re-initiation of the method after a discontinuation of the method of the disclosure. As used herein. "upon re-initiation of the method after a discontinuation" means an interruption of the administration of ponesimod of at least one, at least two or preferably at least 3 days before treatment is re-initiated. In some embodiments, the regimen comprises an up-titration step at initiation of the method or upon re-initiation of the method after a discontinuation.

In some embodiments of the methods of the disclosure, the up-titration regimen one disclosed in U.S. Pat. No. 10,220,023, incorporated herein by reference. For example, in certain aspects, the up-titration comprises administering orally once daily about 2 mg of ponesimod on days 1 and 2; about 3 mg of ponesimod on days 3 and 4; about 4 mg of ponesimod on days 5 and 6; about 5 mg of ponesimod on day 7; about 6 mg of ponesimod on day 8; about 7 mg of ponesimod on day 9; about 8 mg of ponesimod on day 10;

about 9 mg of ponesimod on day 11; and about 10 mg of ponesimod on days 12, 13, and 14.

In other embodiments of the methods of the disclosure, the up-titration comprises administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; 9 mg of ponesimod on day 11; and 10 mg of ponesimod on days 12, 13, and 14.

In some embodiments, the maintenance dose is about 20 mg of ponesimod once daily.

In some embodiments, the regimen comprises an up-titration step at initiation of the method or upon re-initiation of the method after a discontinuation, comprising administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; and 9 mg of ponesimod on day 11; 10 mg of ponesimod on days 12, 13, and 14, followed by the administering of the 20 mg of ponesimod once daily thereafter.

In some aspects of the disclosed methods, the regimen is sufficient to avoid worsening of the fatigue-related symptoms. A regimen is sufficient to avoid worsening of the fatigue-related symptoms when the patient's fatigue-related symptoms (assessed as described herein) after administration of the ponesimod regimen, are either improved or unchanged compared to the patient's fatigue-related symptoms (assessed as described herein) prior to administration of the ponesimod regimen, for example, at baseline.

In other embodiments, the methods of the disclosure are directed to reducing the number of combined unique active lesions (CUALs) in a patient.

CUALs are new Gd+T1 lesions plus new or enlarging T2 lesions (without double-counting of lesions). The cumulative number of CUAL is considered a reliable outcome measure of inflammatory MS disease activity. Radiological evidence of disease activity is routinely used to support disease diagnosis and to inform therapeutic decisions targeting no evidence of disease activity (NEDA), clinical (relapses or disability accumulation) or radiological (brain lesions on MRI) perspective. See Lublin F D. *Disease activity free status in MS*. Mult Scler Relat Disord. 2012 January; 1(1):6-7. doi: 10.1016/j.msard.2011.08.001. Epub 2011 Aug. 27. PubMed PMID: 25876444.

CUALs are detected using magnetic resonance imaging (MRI) techniques.

In this aspect of the disclosed methods, the ponesimod regimen administered to the patient is sufficient to reduce the number of CUALs by at least 40% relative to a patient population at substantially the same level of disease progression receiving a standard of care treatment. That is, the patient administered the ponesimod regimen will have acquired at least 40% fewer CUALs as compared to a patient having substantially the same degree of MS progression who is receiving a standard of care treatment.

In some embodiments, the ponesimod regimen administered to the patient is sufficient to reduce the number of CUALs by at least 20% to about 65% relative to a patient population at substantially the same level of disease progression receiving a standard of care treatment. In some embodiments, the ponesimod regimen administered to the patient is sufficient to reduce the number of CUALs by at least 30% relative to a patient population at substantially the same level of disease progression receiving a standard of care treatment. In some embodiments, the ponesimod regimen administered to the patient is sufficient to reduce the number of CUALs by at least 50% relative to a patient population at substantially the same level of disease progression receiving a standard of care treatment. In some embodiments, the ponesimod regimen administered to the patient is sufficient to reduce the number of CUALs by at least 55% relative to a patient population at substantially the same level of disease progression receiving a standard of care treatment.

As used herein, the term "standard of care treatment" refers to a physician-prescribed treatment of MS. In some embodiments, the standard of care comprises, consists of, or consists essentially of administering an MS treatment that has been approved by a regulatory authority. In some embodiments, the standard of care treatment is Interferon (IFN) β-1a 30 mcg i.m. once weekly (Avonex®), IFN β-1a 22 or 44 mcg s.c. 3 times weekly (Rebif®). IFN β-1b 250 mcg s.c. every other day (Betaferon®, Extavia®), Pegylated IFN β-1a 125 mcg subcutaneously every 2 weeks (Plegridy®), Glatiramer acetate 20 mg s.c. once a day (o.d.) or 40 mg subcutaneously 3 times weekly (Copaxone®), Glatiramer acetate 20 mg s.c. o.d. (Glatopa®), Natalizumab 300 mg i.v. every 4 weeks (Tysabri®), Mitoxantrone i.v. every 3 months (Novantrone®), Alemtuzumab concentrate for solution for infusion, 12 mg alemtuzumab in 1.2 mL (10 mg/mL) (Lemtrada®). Fingolimod 0.5 mg orally o.d. (Gilenya®), Teriflunomide 7 mg, 14 mg o.d. (Aubagio®), Dimethyl fumarate (BG-12) gastro-resistant hard capsules 120/240 mg twice daily (Tecfidera®), or Cladribine 40 to 100 mg orally per treatment week (Mavenclad®).

In some embodiments, the standard of care treatment comprises a SIP receptor modulator that is not ponesimod.

In other embodiments, the standard of care treatment comprises teriflunomide. In some embodiments, the standard of care treatment comprises administration of about 14 mg of teriflunomide orally once daily.

In some embodiments, the patient has had no prior disease modifying treatment (DMT) for multiple sclerosis. In some embodiments, the patient has had no prior disease modifying treatment (DMT) for multiple sclerosis within about two years prior to initiation of treatment with ponesimod. In some embodiments, patients that have had no prior DMT for multiple sclerosis realize improved efficacy from use of ponesimod to address fatigue with respect to a standard of care treatment that does not comprise ponesimod, such as teriflunomide. Accordingly, with respect to these patients and others, the disclosed methods provide health care providers with options for improved outcomes compared to standard of care.

In some embodiments, the methods are directed to patients having a baseline expanded disability status scale (EDSS) score of ≤3.5, more particularly ≤3.0. In some embodiments, the methods are directed to patients having no Gd+/T1 lesions at baseline.

The present disclosure also provides pharmaceutical products comprising ponesimod. Typically, the pharmaceutical product is a package or is packaged, for example, a bottle, a pouch, or a blister pack.

In some embodiments, the package includes instructions. In certain embodiments, instructions are for administering ponesimod to a human patient suffering from multiple sclerosis and fatigue in a regimen that is effective to avoid worsening of fatigue-related symptoms. In other embodiments, the package provides instructions and/or fatigue-related symptom data directed to patients having had no prior disease modifying treatment (DMT) for multiple sclerosis for a period of about two years. In further embodiments, the package provides instructions and/or fatigue-related symptom data directed to patients having a baseline expanded disability status scale (EDSS) score of ≤3.5, more particularly ≤3.0. In yet other embodiments, the package provides instructions and/or fatigue-related symptom data directed to patients having no Gd+/T1 lesions at baseline.

Figure 3A:
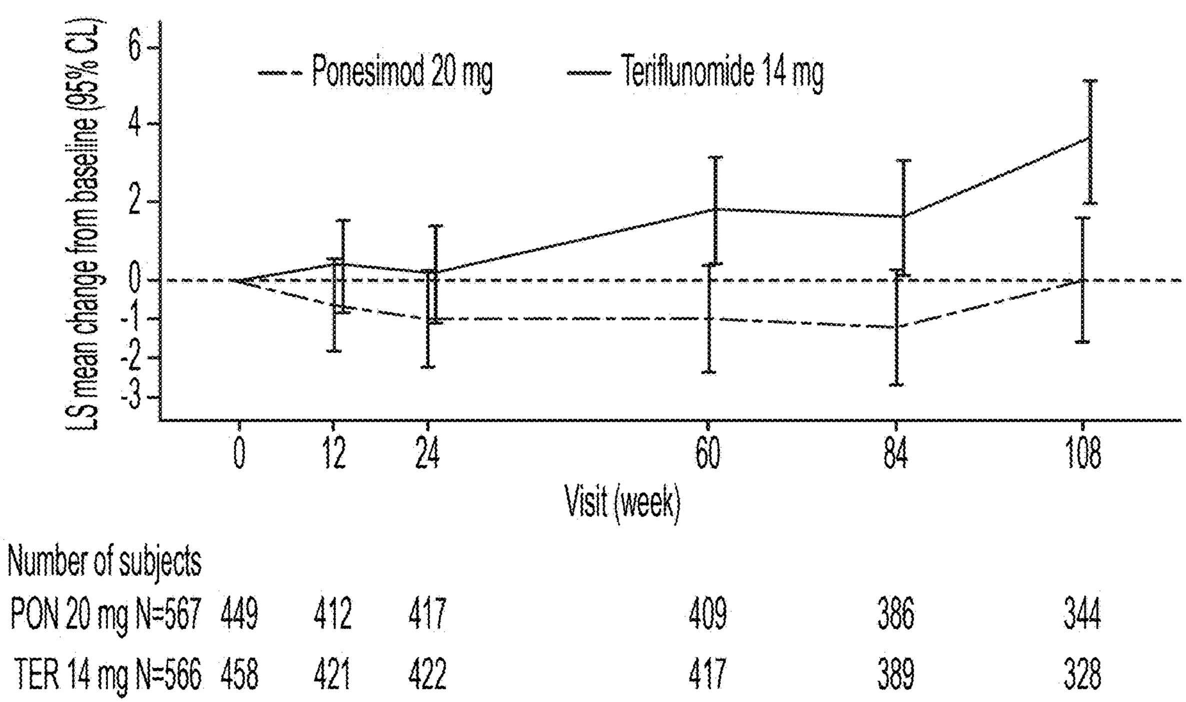
FIG. 3A shows change from baseline up to week 108 for the FSIQ-RMS weekly symptoms score by visit. MMRM (Main analysis) Analysis Set; Full Analysis Set.

As used herein, the term "group level" refers to a group level change or difference between groups of patients, e.g., group level differences in an outcome seen in clinical trials when comparing the treatment groups. For instance, FIG. 3A shows the mean change from baseline for ponesimod 20 mg and teriflunomide 14 mg over time—and it visually shows the separation or difference in change from baseline in the treatment groups.

As used herein, the term "patient level" refers to individual or within patient level of change. As used herein, "clinically meaningful" refers to the practical importance of a treatment effect and whether it has a real genuine, palpable, noticeable effect on symptoms and/or daily life. When interpreting data from a Patient Reported Outcome (PRO), for example, it is helpful to define a level of change on the PRO score over a predetermined time period that should be interpreted as a treatment benefit. Various terms are used for this level of change, including meaningful change threshold (MCT). This threshold can be used to conduct a responder analysis where an individual patient is a responder if the level of change on the PRO score for that patient exceeds the MCT. The proportion of responders between treatment groups can be compared to evaluate treatment effect. For example, in certain embodiments disclosed herein, there is an analysis of the percentage of responders in the ponesimod and teriflunomide treatment groups using an MCT of −6.3 on the FSIQ-RMS weekly symptom score. The percentage of subjects in the stable or improved category is also calculated. And the percentage of responders can also be visualized on a graph (a cumulative distribution function) which shows the cumulative percentage of patients showing all possible levels of change in the respective treatment groups. Accordingly, evaluation of within patient changes using MCT and associated responder analyses are used to provide additional interpretation to a p-value derived from a statistical test As used herein, the term "statistically significant" refers to the likelihood that a relationship between two or more variables is caused by something other than chance. A p-value less than 0.05 (typically ≤0.05) is a common metric for statistical significance and is indicative of strong evidence against the null hypothesis, as there is less than a 5% probability the null is correct (and the results are random).

As used herein, unless otherwise noted, the terms "treating", "treatment" and the like, shall include the management and care of a subject or patient (preferably mammal, more preferably human) for the purpose of combating a disease, condition, or disorder and includes the administration of a compound described herein to prevent the onset of the symptoms or complications, alleviate one or more of the symptoms or complications, or eliminate the disease, condition, or disorder In some aspects of the disclosed methods, the regimen is sufficient to treat early-stage multiple sclerosis (ESMS) in a patient. ESMS in a patient is indicated by a patient having a baseline expanded disability status scale (EDSS) score of ≤3.5, more particularly an EDSS score of ≤3. In addition, the patient may also be treatment naïve (i.e., no MS disease-modifying therapy received at any time in the past). Accordingly, ponesimod is useful as an early high efficiency treatment option, and, in particular aspects, the ponesimod treatment regimens disclosed herein include identifying a patient with ESMS, and more particularly, identifying a patient with an EDSS score of ≤3. As disclosed herein, this patient population has an increased benefit compared to standard of care treatments, with such increased benefit supporting improved long-term outcomes. For example, a physician or other medical professional can select a disclosed ponesimod treatment over other standard of care treatments for a patient with ESMS. In other embodiments, standard of care treatment can be discontinued in favor of a disclosed ponesimod treatment for patients with ESMS.

In certain aspects, the ponesimod treatment regimens disclosed herein reduce the number of combined unique active lesions (CUALs) in a patient suffering from early-stage multiple sclerosis (ESMS), including in the treatment of treatment naïve patients. In certain embodiments, such regimens are effective to reduce the number of CUALs relative to a patient population at substantially the same level of disease progression receiving a standard of care treatment that does not comprise ponesimod. In some embodiments, the relative reduction in the number of CUALs is at least about 35%; or at least about 40%; or at least about 45%; or at least about 50%; or at least about 55%; or at least about 60%.

In some embodiments, the relative reduction of the number of CUALs is from about 35% to about 40%; or from about 40% to about 45%; or about 45% to about 50%; or from about 50% to about 55%; or from about 55% to about 60%.

In further aspects, the ponesimod treatment regimens disclosed herein reduce annualized relapse rate (ARR) in a patient suffering from early-stage multiple sclerosis (ESMS). In certain embodiments, such regimens are effective to reduce the ARR relative to a patient population at substantially the same level of disease progression receiving a standard of care treatment that does not comprise ponesimod. In some embodiments, the relative reduction in ARR is at least about 20%; or at least about 25%; or at least about 30%; or at least about 35%; or at least about 40%.

In some embodiments, the relative reduction in ARR is from about 20% to about 25%; or from about 25% to about 30%; or about 30% to about 35%; or from about 35% to about 40%.

In other aspects, the ponesimod treatment regimens disclosed herein reduce MS-fatigue mean difference in a patient suffering from early-stage multiple sclerosis (ESMS). In certain embodiments, such regimens are effective to reduce MS-fatigue mean difference relative to a patient population at substantially the same level of disease progression receiving a standard of care treatment that does not comprise ponesimod. In some embodiments, the relative mean difference is about −7.0%; or about −6.0%; or about −5.0%; or about −4.0%; or about −3.0%; or about −2.0%; or about −1.0%.

In some embodiments, the relative MS-fatigue mean difference relative to a patient population at substantially the same level of disease progression receiving a standard of care treatment that does not comprise ponesimod is from about −1.0% to about −1.5%; or from about −1.5% to about −2.0%; or from about −2.0% to about −2.5%; or from about −2.5% to about −3.0%; or from about −3.0% to about −3.5%; or from about −3.5% to about −40.0%; or from about −4.0% to about −4.5%; or from about −4.5% to about −5.0%; or from about −5.0% to about −5.5%; or from about −5.5% to about −6.0%; or from about −6.0% to about −6.5%; or from about −6.5% to about −7.0%.

Figure 29:
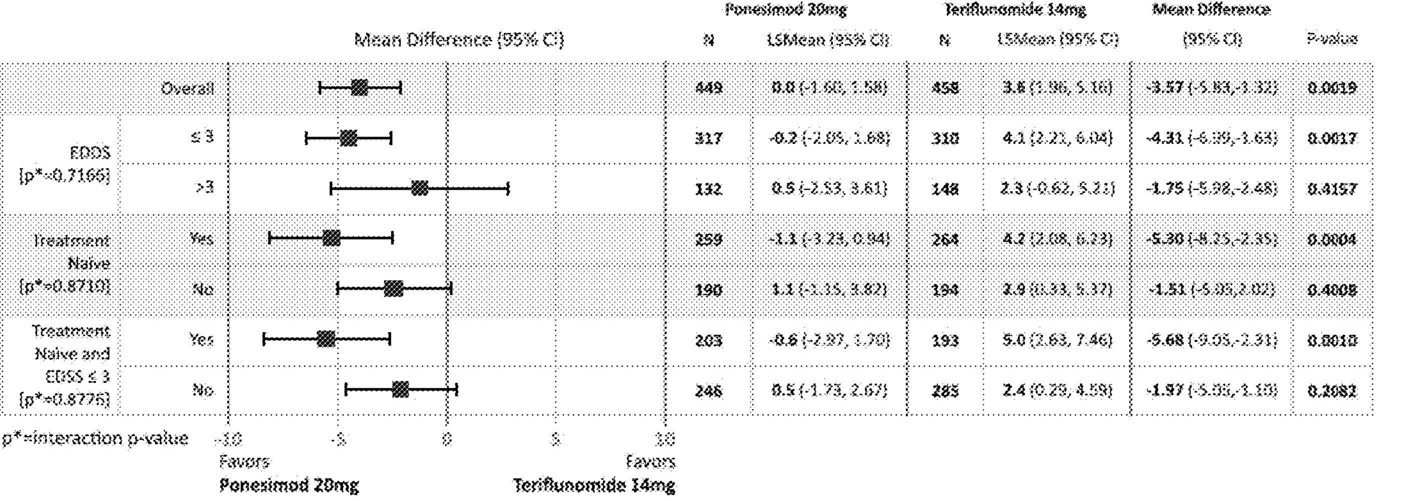
FIG. 29 depicts a table of results for Fatigue Symptoms and Impacts Questionnaire—Relapsing Multiple Sclerosis (FSIQ-RMS) for various subgroups of patients treated with ponesimod and teriflunomide.

As reflected in Example 3 and FIG. 29, the MS-fatigue mean difference is based on the Fatigue Symptoms and Impact Questionnaire—Relapsing Multiple Sclerosis (FSIQ-RMS).

In certain aspects, the disclosure is directed to a pharmaceutical product comprising ponesimod, wherein the pharmaceutical product is packaged and the package includes instructions for administering ponesimod to a patient having early-stage multiple sclerosis (ESMS) in a regimen that is effective to treat the ESMS, wherein the patient has a baseline expanded disability status scale (EDSS) score of ≤3.0.

The following Examples are provided to illustrate some of the concepts described within this disclosure. While the Examples are considered to provide embodiments, they should not be considered to limit the more general embodiments described herein.

Example A: Fatigue Symptoms and Impact Questionnaire—Relapsing Multiple Sclerosis (FSIQ-RMS)

The patient-reported outcome questionnaire used for the below Examples is the Fatigue Symptoms and Impact Questionnaire—Relapsing Multiple Sclerosis (FSIQ-RMS). The FSIQ-RMS is an MS specific 20-item PRO measure that comprises 2 domains: one measuring MS symptoms (7 items) and one measuring MS-related impacts (13 items). The 7 symptom items and 13 impact items (in 3 impacts subdomains: physical, cognitive and emotional, and coping) are presented below.

MS Symptoms Domain—7 Items

For the MS symptoms domain, the FSIQ-RMS asks about a patient's fatigue-related symptoms of relapsing MS over the past 24 hours while doing routine daily activities (e.g., housework, yard work, shopping, working, etc.) for Items 1-6 or while at rest (e.g., reading a book, watching TV, etc.) for Item 7. Patients are asked to select a response on a scale of 0 to 10 that best describes their experience and are asked to not skip any questions, with no answers being right or wrong.

Figure 31:
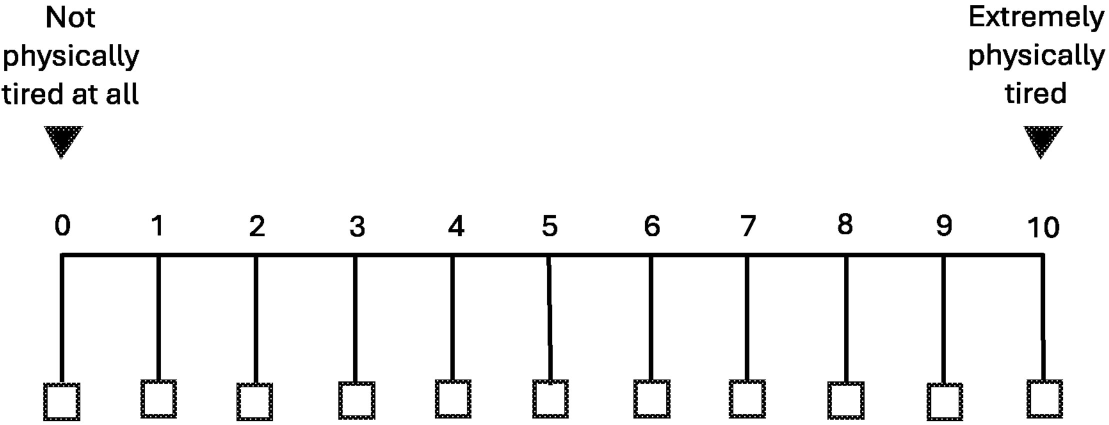

Item 1—In the past 24 hours, while doing routine daily activities, how physically tired did you feel? See FIG. 31.

Figure 32:
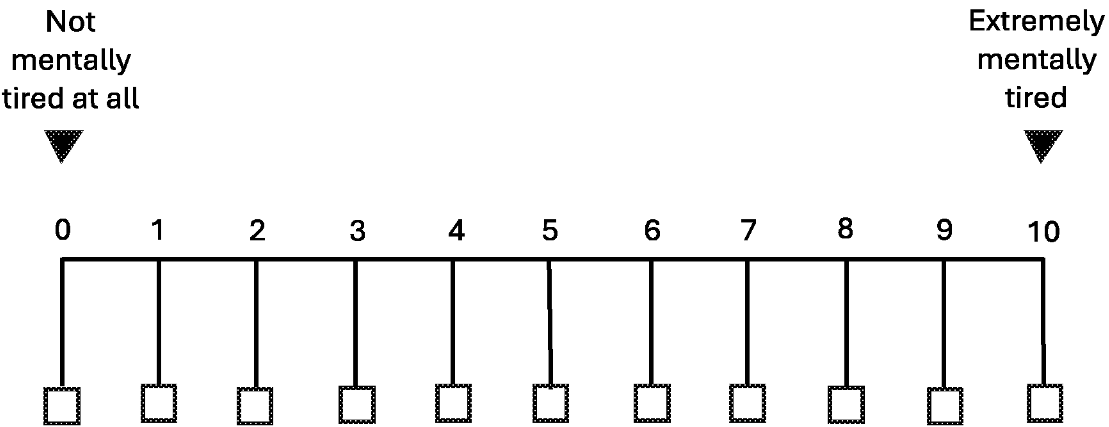

Item 2—In the past 24 hours, while doing routine daily activities, how mentally tired did you feel? See FIG. 32.

Figure 33:
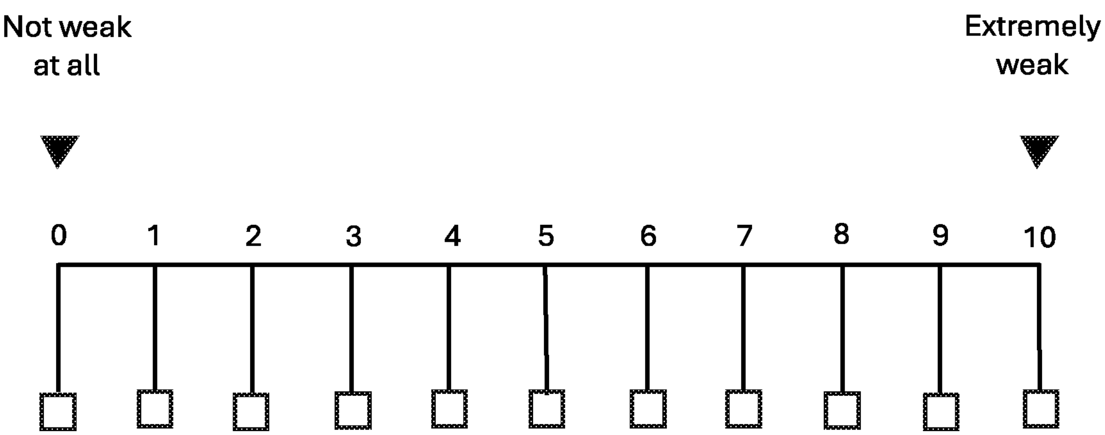

Item 3—In the past 24 hours, while doing routine daily activities, how physical weak did you feel? See FIG. 33.

Figure 34:
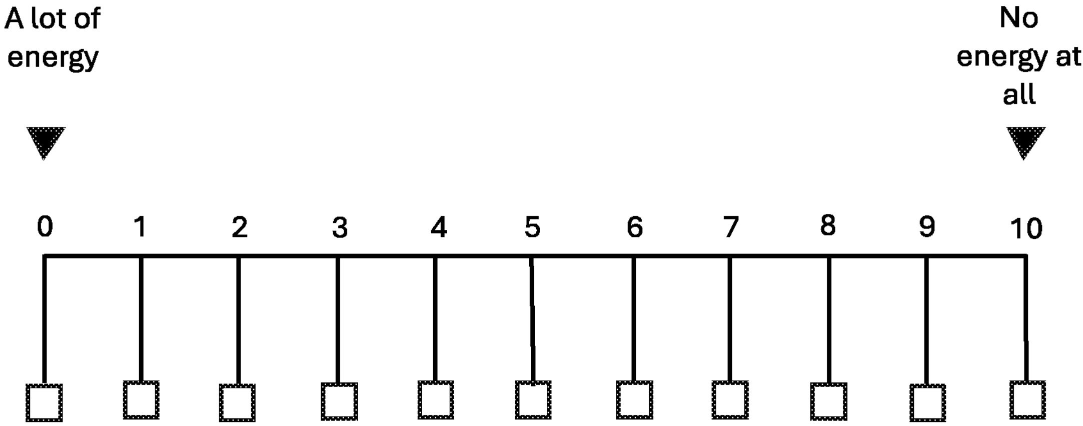

Item 4—In the past 24 hours, how would you rate your energy while doing routine daily activities? See FIG. 34.

Figure 35:
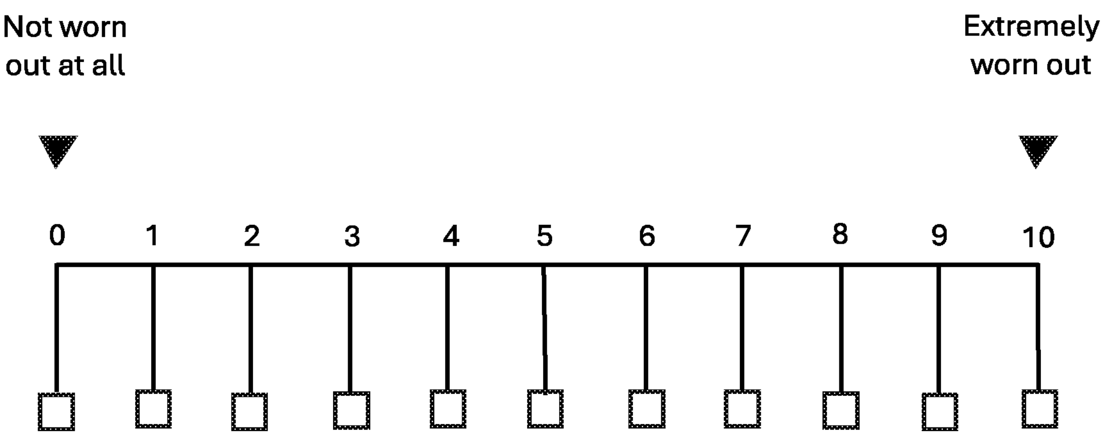

Item 5—In the past 24 hours, while doing routine daily activities, how worn out did you feel? See FIG. 35.

Figure 36:
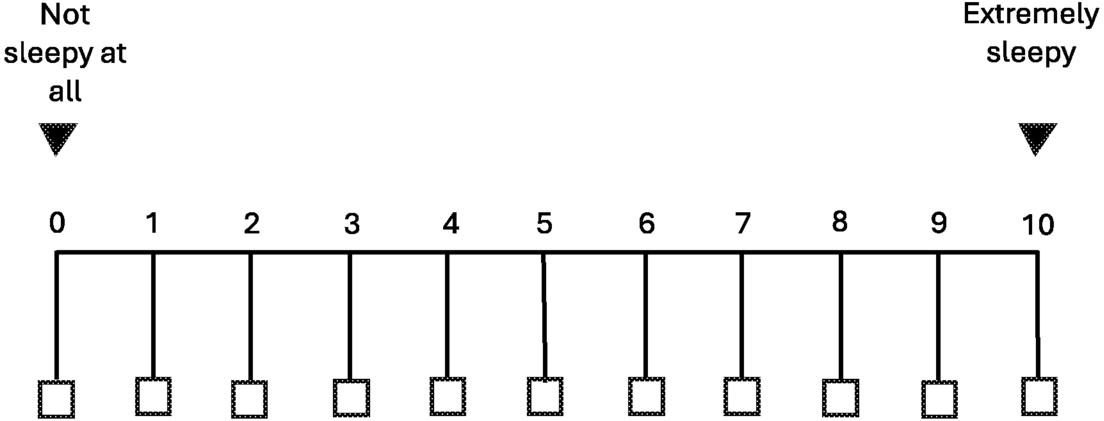

Item 6—In the past 24 hours, while doing routine daily activities, how sleepy did you feel? See FIG. 36.

Figure 37:
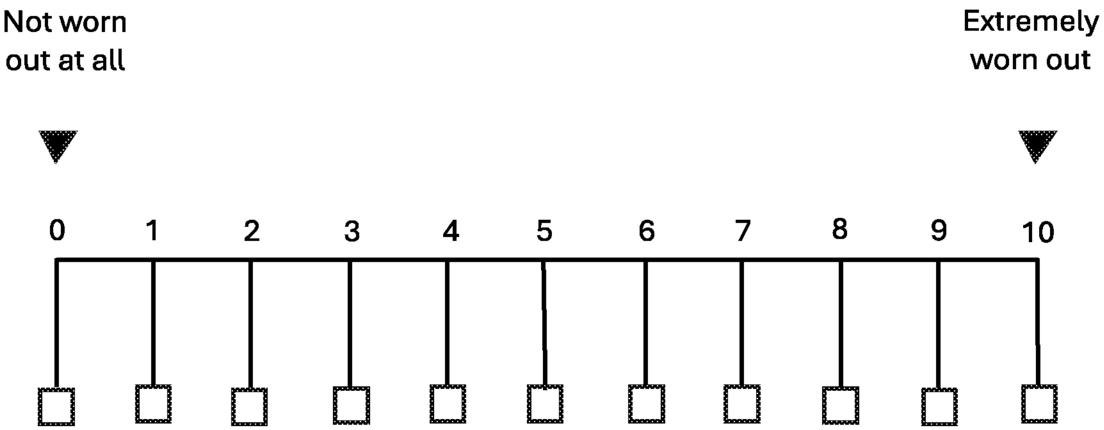

Item 7—In the past 24 hours, how worn out did you feel while at rest? See FIG. 37. MS-Related Impacts—13 Items For the MS-related impacts domain, the FSIQ-RMS asks about how a patient's life was affected by fatigue-related symptoms of relapsing MS in the past 7 days. Patients are asked to select a response on a scale of 0 to 4 that best describes their experience and are asked to not skip any questions, with no answers being right or wrong.

Figure 38:
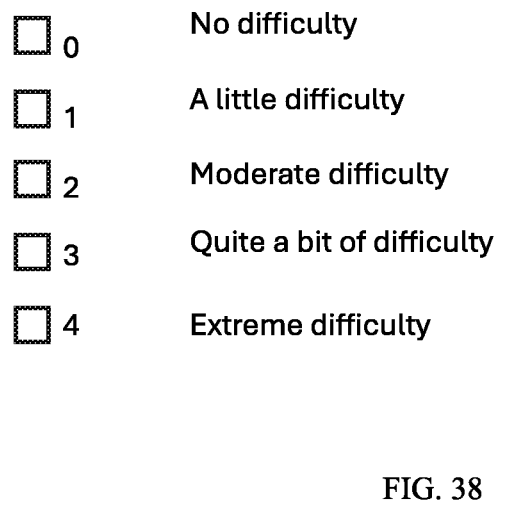

Item 1—Thinking about your fatigue-related symptoms over the past 7 days, how much difficulty did you have running errands (such as grocery shopping or going to the bank or ATM)? See FIG. 38.

Figure 39:
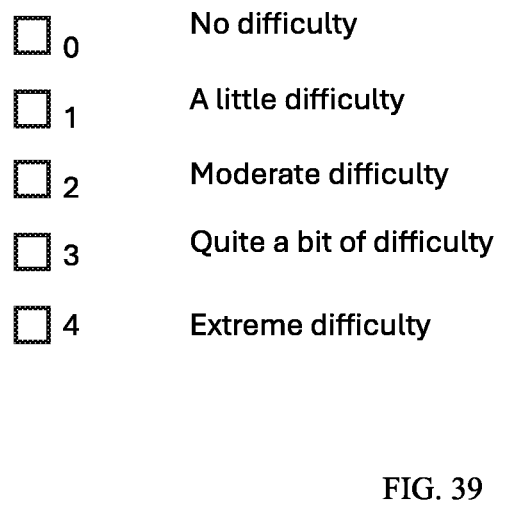

Item 2—Thinking about your fatigue-related symptoms over the past 7 days, how much difficulty did you have communicating clearly? See FIG. 39.

Item 3—Thinking about your fatigue-related symptoms over the past 7 days, how much difficulty did you have thinking clearly? See FIG. 40.

Figure 41:
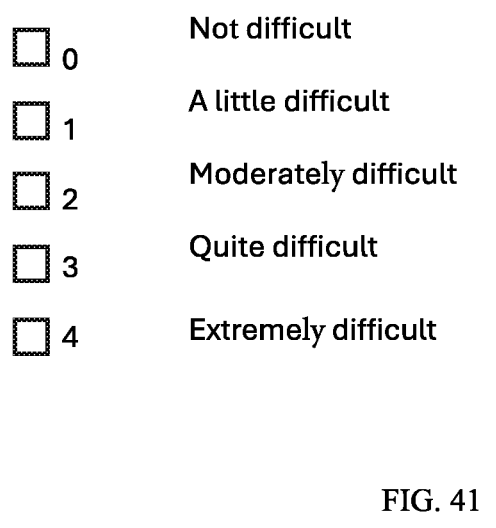

Item 4—Thinking about your fatigue-related symptoms over the past 7 days, how difficult was it for you to motivate yourself to do routine daily activities? See FIG. 41.

Figure 42:
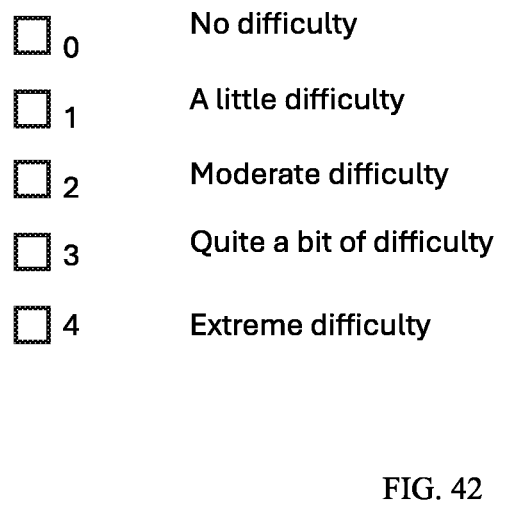

Item 5—Thinking about your fatigue-related symptoms over the past 7 days, how much difficulty did you have doing indoor household chores? See FIG. 42.

Item 6—Thinking about your fatigue-related symptoms over the past 7 days, how much difficulty did you have walking? See FIG. 43.

Item 7—Thinking about your fatigue-related symptoms over the past 7 days, how much difficulty did you have maintaining relationships with people you are close to? See FIG. 44.

Figure 45:
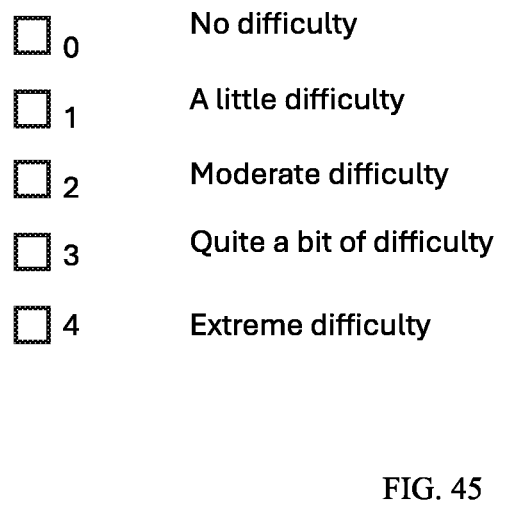

Item 8—Thinking about your fatigue-related symptoms over the past 7 days, how much difficulty did you have taking part in social activities (such as going to the movies or going out to eat)? See FIG. 45.

Item 9—Thinking about your fatigue-related symptoms over the past 7 days, how frustrated were you? See FIG. 46.

Figure 47:
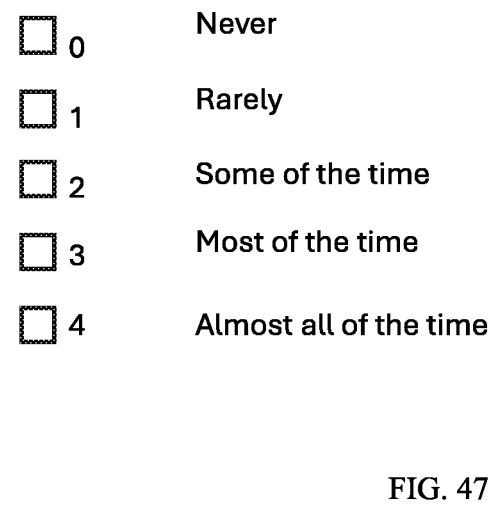

Item 10—Thinking about your fatigue-related symptoms over the past 7 days, how often were you forgetful? See FIG. 47.

Item 11—Thinking about your fatigue-related symptoms over the past 7 days, how often did you have to take a nap? See FIG. 48.

Item 12—Thinking about your fatigue-related symptoms over the past 7 days, how often did you have to take a break? See FIG. 49.

Figure 50:
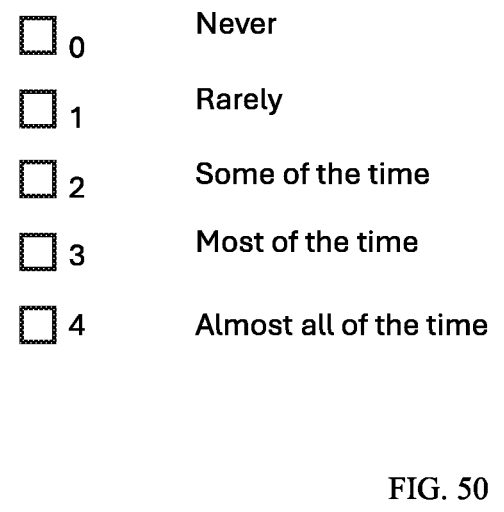

Item 13—Thinking about your fatigue-related symptoms over the past 7 days, how often did you have to rearrange your plans? See FIG. 50.

Example 1

Study Design

A prospective, multicenter, randomized, double-blind, active controlled, parallel-group, phase III, superiority study was conducted. The study was designed to compare the efficacy, safety, and tolerability of ponesimod 20 mg vs teriflunomide 14 mg in adult subjects with relapsing MS.

Randomization: Subjects were randomized in a 1:1 ratio to ponesimod 20 mg or teriflunomide 14 mg, stratified by prior use of MS disease modifying treatment (DMT) in the last two years prior to randomization (yes, no) and by baseline expanded disability status scale (EDSS) score (EDSS≤3.5, EDSS>3.5).

Inclusion Criteria

This study enrolled adult male and female subjects aged 18 to 55 years with established diagnosis of MS, as defined by the 2010 revision of McDonald Diagnostic Criteria [Polman C H, et al. *Diagnostic criteria for multiple sclerosis:* 2010 *revisions to the McDonald criteria*. Ann Neurol. 2011; 69(2):292-302], with relapsing course from onset (i.e., relapsing-remitting multiple sclerosis and secondary progressive multiple sclerosis [SPMS] with superimposed relapses). The trial included up to a maximum 15% of subjects with SPMS with superimposed relapses.

Subjects had active disease evidenced by one or more MS attacks with onset within the period of 12 to 1 months prior to baseline EDSS assessment, or by two or more MS attacks with onset within the 24 to 1 months prior to baseline EDSS assessment, or with one or more gadolinium-enhancing (Gd+) lesion(s) of the brain on an MRI performed within 6 months prior to baseline EDSS assessment. Enrolled subjects were ambulatory with an EDSS score of up to 5.5 inclusive. The subjects were treatment-naïve (i.e., no MS disease-modifying therapy received at any time in the past) or previously treated with interferon (IFN) β-1a, IFN β-1b, glatiramer acetate, dimethyl fumarate, or natalizumab.

Exclusion Criteria:

Subjects with significant medical conditions or therapies for such conditions (e.g., cardiovascular, pulmonary, immunological, hepatic, ophthalmological, ocular) or lactating or pregnant women were not eligible to enter the study.

Subjects with contraindications to MRI or with clinically relevant medical or surgical conditions that, in the opinion of the investigator, would put the subject at risk by participating in the study were not eligible to enter the study.

Study/Treatment Duration:

For an individual subject, the maximum duration of the study was approximately 118 weeks consisting of 6 weeks of screening, 108 weeks of treatment and 4 weeks of safety follow-up. Subjects discontinuing treatment prematurely had an option to stay in a post-treatment observation period (PTOP) for up to 108 weeks.

The Study Consisted of the Following Periods:

Pre-randomization period—Up to 45 days before randomization.

Treatment period: The double-blind treatment period lasted for 108 weeks. It consisted of a randomization visit, visits at two, four, and 12 weeks after randomization, and 12-weekly visits thereafter.

End-of-Treatment (EOT):

The EOT visit took place at Week 108 (or earlier in case of premature discontinuation of study drug). In all cases, the EOT visit took place one day after the last dose of study drug but no later than 7 days after the last dose of study drug.

Subjects who completed treatment until Week 108 were eligible to enroll in an extension study conducted under a separate protocol. Subjects who discontinued study drug prematurely for any reason were not eligible for the extension study.

Subjects who prematurely discontinued study drug treatment were subsequently treated according to local standard of care at the investigator's discretion and were followed in the post-treatment observation period.

Post-Treatment Safety Follow-Up (FU) Period:

Teriflunomide is eliminated slowly from plasma. An accelerated elimination procedure was used by all subjects after the last dose of study drug. A safety FU after the last dose of study drug was mandated.

All Subjects Entered the Safety FU Period:

For subjects who entered the extension study, the FU period started after the last dose of study drug and ended with a safety FU visit (FU1) 14-22 days after the last dose of study drug or with an abbreviated FU2 23-37 days after the last dose of study drug (if compliance to the teriflunomide accelerated elimination procedure was assessed as not sufficient at FU1).

For subjects who did not enter the extension study, the safety FU period lasted for 30 days after the last dose of study drug and included two safety FU visits (FU1, FU2) at 14-22 and 30-37 days after the last dose of study drug, respectively.

Post-Treatment Observation Period (PTOP):

Subjects who prematurely discontinued study treatment enter the PTOP which lasts until 108 weeks after randomization (i.e., planned EOT period). It consisted of an abbreviated schedule of assessments at the time of the originally scheduled 12-weekly visits.

End-of-Study (EOS)

EOS was reached when treatment, safety FU, and, if applicable, PTOP have been completed.

For subjects who completed the 108-week treatment period and entered the extension study, the EOS visit corresponded to the FU visit (FU1) conducted 14-22 days after the last study drug dose or to the abbreviated FU2 visit conducted 23-37 days after the last study drug dose (if needed for compliance reasons with the teriflunomide accelerated elimination procedure).

For all other subjects, the EOS visit corresponded to the 30-day FU visit (FU2) or to the last visit of PTOP (i.e., Week 108 Visit of the PTOP), whichever was last.

Study Treatment:

The treatment period consisted of an up-titration period (from Day 1 to 14) and a maintenance period (Day 15 until EOT).

During an initial phase of the study, the study drugs in the up-titration period were administered in a double-dummy fashion. Ponesimod (or matching placebo) was presented as tablet, and teriflunomide 14 mg (or matching placebo) was presented as capsule (i.e., daily administration of one tablet and one capsule). At a later phase, the double-dummy material (tablet and capsule) was replaced by the daily administration of one capsule containing either ponesimod or teriflunomide.

In the maintenance period, the study treatment consisted of the daily administration of one capsule containing ponesimod 20 mg or teriflunomide 14 mg.

To reduce the first-dose effect of ponesimod, an up-titration scheme was implemented from Day 1 to Day 14:

Days 1 and 2; 2 mg.
Days 3 and 4; 3 mg.
Days 5 and 6; 4 mg.
Day 7; 5 mg.
Day 8; 6 mg.
Day 9; 7 mg.
Day 10; 8 mg.
Day 11; 9 mg.
Days 12, 13, and 14; 10 mg.
Day 15 until EOT; 20 mg.

Primary analysis set for efficacy: The Full Analysis Set (FAS) included all randomized subjects. Subjects were evaluated according to the treatment they were randomized to.

Primary efficacy variable/primary timepoint: The primary endpoint was annualized relapse rate (ARR) up to the end of study (EOS) defined as the number of confirmed relapses per subject-year. All available data up to EOS, regardless of treatment discontinuation was included (ITT approach).

Secondary efficacy variables and testing strategy: Four secondary efficacy endpoints were analyzed as per the statistical testing strategy outlined in FIG. 1.

- Change from baseline to Week 108 in fatigue-related symptoms as measured by the symptoms domain of the FSIQ-RMS patient-reported outcome [Fatigue]
- Cumulative number of combined unique active lesions from baseline to Week 108 on brain MRI [CUALs]
- Time to first 12-week confirmed disability accumulation (CDA) from baseline to EOS on Expanded Disability Status Scale (EDSS) [12-week CDA]

Time to first 24-week CDA from baseline to EOS on EDSS [24-week CDA]

See FIG. 1 for a schematic representation of the testing strategy.

The primary endpoint was powered with $\alpha$=0.01. The secondary endpoints tested with an overall $\alpha$=0.05.

The sample size for the study was based on the primary endpoint and determined assuming a negative binomial distribution for number of confirmed relapses. A sample size of 1100 subjects (550 per treatment arm) would provide a power of approximately 90% for a significance level of 1%, under the assumption that ARR is 0.320 for teriflunomide 14 mg and 0.215 for ponesimod 20 mg (which corresponds to a rate ratio of 0.67) and using a dispersion=0.9. An annual dropout rate of approximately 15% was assumed for the first year and 7.5% for the second year.

Statistical Methods

The Full Analysis Set (FAS) included all randomized subjects. In order to adhere to the intention-to-treat principle as much as possible, subjects were evaluated according to the treatment they have been randomized to.

The Per-Protocol Set (PPS) comprises all subjects included in the FAS without any major protocol deviations, that impact the assessment of the primary/secondary endpoints, occurring prior to or at randomization.

The Safety Set (SAF) included all randomized subjects who received at least one dose of study treatment. Subjects were analyzed based on actual treatment taken, not randomized treatment.

A generalized linear model with negative binomial distribution was fitted for the primary efficacy endpoint ARR. Two-sided hypotheses were expressed in terms of the model parameters $\mu$P20 mg and $\mu$T14 mg. The primary null hypothesis was that the ARR (p) does not differ between ponesimod 20 mg and teriflunomide 14 mg.

The null hypothesis was tested by a two-sided Wald test within the negative binomial regression model with a two-sided significance level of 0.01 for conclusive evidence and 0.05 for a positive study. Two-sided 99% and 95% Wald confidence intervals were calculated for the relative reduction in mean ARR for ponesimod 20 mg compared to teriflunomide 14 mg.

The primary statistical analysis of the ARR endpoint was performed on the FAS using a negative binomial model for confirmed relapses, with the stratification variables prior use of disease-modifying therapies (DMTs) and EDSS category as well as the number of relapses in the year prior to study entry, included in the model and time in the study as an offset variable. Sensitivity analyses was performed on the PPS and also based on different subgroups derived from baseline variables.

The secondary efficacy endpoints were tested if the primary analysis on ARR leads to the rejection of the null hypothesis in favor of ponesimod 20 mg at an overall two-sided significance level of 0.05. A fallback method was used for testing the family of hypotheses related to the following three secondary endpoints: Absolute change of FSIQ-RMS from baseline to Week 108; Cumulative number of CUAL from baseline to Week 108; Time to 12-week CDA from baseline up to EOS. This was followed in a hierarchical manner by testing Time to 24-week CDA from baseline up to EOS; at the remaining alpha.

The endpoints were analyzed using the FAS population. All secondary endpoints were also analyzed using the PPS population.

Primary Objective

To determine whether ponesimod is more efficacious than teriflunomide in terms of reducing relapses in subjects with RMS.

Results

Disposition and baseline characteristics: A total of 1133 subjects were randomized to the study. 567 to ponesimod 20 mg and 566 to teriflunomide 14 mg. Overall treatment and study discontinuation were balanced across both treatment arms, 83% of subjects completed treatment. The mean age was 36.7 years and 64.9% of subjects were female. Most subjects were recruited in Europe with 50.6% from EU countries. Mean baseline EDSS score was 2.6 and mean disease duration was 7.6 years. Mean pre-study 12-month relapse rate was 1.3, and 42.6% subjects had ≥1 gadolinium-enhancing (Gd+) T lesions. The treatment arms were generally balanced in terms of demographics and baseline disease characteristics.

1. Subject and Treatment Information

A total of 1468 subjects were screened. Of those, 1133 subjects were randomized (567 to ponesimod 20 mg and 566 to teriflunomide 14 mg) across 162 sites in 28 countries, and 1131 subjects received at least one dose of study drug. The disposition of subjects is summarized in Table 1 and a summary of reasons (primary reason) for treatment discontinuation are shown in Table 2. Overall treatment and study discontinuation were balanced across both treatment arms. A total of 6.5% and 2.5% of the subjects discontinued due to AEs or tolerability related reasons in ponesimod 20 mg and teriflunomide 14 mg, respectively, while 1.9% and 4.3% discontinued due to efficacy related reasons. There were 2 deaths reported during the study—both on teriflunomide 14 mg.

1.1 Disposition and Treatment Discontinuation Information

TABLE 1

Disposition of subjects
Analysis Set: Subjects screened

| | Ponesimod 20 mg N = 567 n (%) | Teriflunomide 14 mg N = 566 n (%) | Total N = 1133 n (%) |
|---|---|---|---|
| Subjects screened | | | 1468 |
| Subjects re-screened | | | 110 |
| Subjects randomized | 567 (100) | 566 (100) | 1133 (100) |
| Subjects randomized after re-screening | 47 (8.3) | 36 (6.4) | 83 (7.3) |
| Subjects treated | 565 (99.6) | 566 (100) | 1131 (99.8) |
| Subjects completed treatment as per protocol | 471 (83.1) | 473 (83.6) | 944 (83.3) |
| Subjects completed study as per protocol | 490 (86.4) | 495 (87.5) | 985 (86.9) |
| Subjects completed treatment and study as | 465 (82.0) | 465 (82.2) | 930 (82.1) |

TABLE 1-continued

| Disposition of subjects<br>Analysis Set: Subjects screened | | | |
|---|---|---|---|
| | Ponesimod<br>20 mg<br>N = 567<br>n (%) | Teriflunomide<br>14 mg<br>N = 566<br>n (%) | Total<br>N = 1133<br>n (%) |
| per protocol | | | |
| Subjects stayed in study beyond safety follow-up (PTOP) | 67 (11.8) | 62 (11.0) | 129 (11.4) |

Percentages based on subjects randomized Safety follow-up is up to EOT + 30 days.
PTOP = Post-treatment observation period.

TABLE 2

| Reasons for premature treatment discontinuation<br>Analysis Set: Safety Set | | | |
|---|---|---|---|
| | Ponesimod<br>20 mg<br>N = 565<br>n (%) | Teriflunomide<br>14 mg<br>N = 566<br>n (%) | Total<br>N = 1131<br>n (%) |
| Subjects who prematurely discontinued study treatment | 94 (16.6) | 93 (16.4) | 187 (16.5) |
| Reasons for premature discontinuation of study treatment | | | |
| Subject decision | 39 (6.9) | 49 (8.7) | 88 (7.8) |
| Efficacy related | 7 (1.2) | 14 (2.5) | 21 (1.9) |
| Tolerability related | 8 (1.4) | 5 (0.9) | 13 (1.1) |
| Other | 19 (3.4) | 26 (4.6) | 45 (4.0) |
| Not known | 5 (0.9) | 4 (0.7) | 9 (0.8) |
| Physician decision | 40 (7.1) | 23 (4.1) | 63 (5.6) |
| Adverse event | 29 (5.1) | 9 (1.6) | 38 (3.4) |
| Lack of efficacy/treatment failure | 4 (0.7) | 10 (1.8) | 14 (1.2) |
| Other | 7 (1.2) | 4 (0.7) | 11 (1.0) |
| Pre-specified study treatment discontinuation criteria | 12 (2.1) | 16 (2.8) | 28 (2.5) |
| Lost to follow-up | 2 (0.4) | 3 (0.5) | 5 (0.4) |

TABLE 2-continued

| Reasons for premature treatment discontinuation<br>Analysis Set: Safety Set | | | |
|---|---|---|---|
| | Ponesimod<br>20 mg<br>N = 565<br>n (%) | Teriflunomide<br>14 mg<br>N = 566<br>n (%) | Total<br>N = 1131<br>n (%) |
| Death | 0 | 2 (0.4) | 2 (0.2) |
| Reason not provided | 1 (0.2) | 0 | 1 (0.1) |

1.2 Demographic and Baseline Characteristics

Randomization was stratified by prior-DMT in the last two years prior to randomization (yes: 39.5%; no: 60.5%) and EDSS score at baseline (≤3.5; 83.3%; >3.5 16.7%). The mean age was 36.7 years and the majority of subjects (64.9%) were female. Most subjects were recruited in Europe with 50.6% from EU countries. Mean baseline EDSS score was 2.6, mean disease duration was 7.6 years and 97.4% were RRMS subjects. Mean pre-study 12-month relapse rate was 1.3, and 42.6% subjects had ≥1 Gd+T1 lesions on brain MRI. The treatment arms were generally balanced in terms of demographics and baseline disease characteristics (Tables 3 and 4).

TABLE 3

| Demographic characteristics<br>Analysis Set: Full Analysis Set | | | |
|---|---|---|---|
| | Ponesimod<br>20 mg<br>N = 567 | Teriflunomide<br>14 mg<br>N = 566 | Total<br>N = 1133 |
| Sex [n (%)] | | | |
| N | 567 | 566 | 1133 |
| Male | 204 (36.0) | 194 (34.3) | 398 (35.1) |
| Female | 363 (64.0) | 372 (65.7) | 735 (64.9) |
| Age (years) | | | |
| N | 567 | 566 | 1133 |
| Mean | 36.7 | 36.8 | 36.7 |
| SD | 8.74 | 8.74 | 8.74 |
| Median | 36.0 | 37.0 | 37.0 |
| Q1, Q3 | 30.0, 44.0 | 30.0, 44.0 | 30.0, 44.0 |
| Min, Max | 18, 55 | 18, 55 | 18, 55 |
| Race [n (%)] | | | |
| N | 567 | 566 | 1133 |
| White | 551 (97.2) | 553 (97.7) | 1104 (97.4) |
| American Indian or Alaska Native | 0 | 1 (0.2) | 1 (0.1) |
| Black or African American | 3 (0.5) | 2 (0.4) | 5 (0.4) |

TABLE 3-continued

| Demographic characteristics<br>Analysis Set: Full Analysis Set | Ponesimod 20 mg N = 567 | Teriflunomide 14 mg N = 566 | Total N = 1133 |
|---|---|---|---|
| Other | 5 (0.9) | 2 (0.4) | 7 (0.6) |
| Not applicable | 8 (1.4) | 8 (1.4) | 16 (1.4) |
| Geographical region/Country of enrolling site [n (%)] | | | |
| European Union (EU) + UK | 289 (51.0) | 284 (50.2) | 573 (50.6) |
| Europe Non-EU + Russia | 233 (41.1) | 239 (42.2) | 472 (41.7) |
| North America | 32 (5.6) | 24 (4.2) | 56 (4.9) |
| Rest of World | 13 (2.3) | 19 (3.4) | 32 (2.8) |

TABLE 4

| Baseline disease characteristics<br>Analysis Set: Full Analysis Set | Ponesimod 20 mg N = 567 | Teriflunomide 14 mg N = 566 | Total N = 1133 |
|---|---|---|---|
| Baseline EDSS | | | |
| N | 567 | 566 | 1133 |
| Mean | 2.57 | 2.56 | 2.56 |
| SD | 1.174 | 1.229 | 1.201 |
| Median | 2.50 | 2.50 | 2.50 |
| Q1, Q3 | 1.50, 3.50 | 1.50, 3.50 | 1.50, 3.50 |
| Min, Max | 0.0, 5.5 | 0.0, 5.5 | 0.0, 5.5 |
| Any DMT(a) received within 2 years prior to Randomization (eCRF) [n (%)] | | | |
| N | 567 | 566 | 1133 |
| Yes | 213 (37.6) | 211 (37.3) | 424 (37.4) |
| No | 354 (62.4) | 355 (62.7) | 709 (62.6) |
| Time since first symptoms (years) at randomization | | | |
| N | 567 | 566 | 1133 |
| Mean | 7.63 | 7.65 | 7.64 |
| SD | 6.781 | 6.782 | 6.779 |
| Median | 5.84 | 5.70 | 5.77 |
| Q1, Q3 | 2.40, 10.97 | 2.24, 11.03 | 2.32, 11.01 |
| Min, Max | 0.2, 40.8 | 0.2, 30.8 | 0.2, 40.8 |
| Number of relapses in last year prior to study entry | | | |
| N | 567 | 565 | 1132 |
| Mean | 1.2 | 1.3 | 1.3 |
| SD | 0.61 | 0.65 | 0.63 |
| Median | 1.0 | 1.0 | 1.0 |
| Q1, Q3 | 1.0, 1.0 | 1.0, 2.0 | 1.0, 1.0 |
| Min, Max | 0, 4 | 0, 5 | 0, 5 |
| Multiple sclerosis subtype [n (%)] | | | |
| N | 567 | 566 | 1133 |
| RRMS | 552 (97.4) | 552 (97.5) | 1104 (97.4) |
| SPMS | 15 (2.6) | 14 (2.5) | 29 (2.6) |
| Presence of Gd + T1 lesions at baseline (from central reader) [n (%)] | | | |
| N | 567 | 564 | 1131 |
| Yes | 226 (39.9) | 256 (45.4) | 482 (42.6) |
| No | 341 (60.1) | 308 (54.6) | 649 (57.4) |
| Volume of T2 lesions at baseline [mm3] (from central reader) | | | |
| N | 565 | 563 | 1128 |
| Mean | 8301.4 | 9489.2 | 8894.3 |
| SD | 10346.28 | 11265.42 | 10826.32 |

TABLE 4-continued

| Baseline disease characteristics<br>Analysis Set: Full Analysis Set | | | |
|---|---|---|---|
| | Ponesimod<br>20 mg<br>N = 567 | Teriflunomide<br>14 mg<br>N = 566 | Total<br>N = 1133 |
| Median | 4841.3 | 5651.0 | 5171.7 |
| Q1, Q3 | 1679.6, 11004.4 | 2022.9, 12978.7 | 1851.3, 11754.1 |
| Min, Max | 0, 86053 | 0, 82776 | 0, 86053 |
| Highly active disease [n (%)] | | | |
| N | 567 | 566 | 1133 |
| Yes | 202 (35.6) | 200 (35.3) | 402 (35.5) |
| No | 365 (64.4) | 366 (64.7) | 731 (64.5) |

(a)DMT = MS disease-modifying treatment.
RRMS = Relapsing-remitting multiple sclerosis,
SPMS = Secondary progressive multiple sclerosis.

1.3 Extent of Exposure

The mean treatment exposure (irrespective of interruptions) was 96.7 weeks in the ponesimod 20 mg arm and 97.5 weeks in the teriflunomide 14 mg arm. Thbe cumulative exposure to ponesimod 20 mg was 1045 subject-years and was 1057 subject-years for teriflunomide 14 mg arm.

TABLE 5

| Study treatment exposure<br>Analysis Set: Safety Set | | |
|---|---|---|
| | Ponesimod<br>20 mg<br>N = 565 | Teriflunomide<br>14 mg<br>N = 566 |
| Treatment exposure, irrespective of interruptions (weeks) | | |
| N | 564 | 566 |
| Mean | 96.69 | 97.45 |
| SD | 29.018 | 27.022 |
| Median | 108.00 | 108.00 |
| Q1, Q3 | 107.29, 108.71 | 107.29, 108.57 |
| Min, Max | 0.3, 111.3 | 0.1, 113.0 |
| Treatment exposure, irrespective of interruptions | | |
| N | 564 | 566 |
| Cumulative exposure (years) | 1045.2 | 1057.1 |

Treatment exposure based on study drug log.
Treatment duration only presented for subjects with available complete treatment end date.
Interruptions derived based on study drug log and number of capsules taken.

2. Primary Endpoint Analysis

Primary efficacy endpoint: Ponesimod 20 mg statistically significantly reduced ARR (confirmed relapses) up to EOS by 30.5% compared to teriflunomide 14 mg (ARR=0.202 for ponesimod 20 mg vs. 0.290 for teriflunomide 14 mg, rate ratio: 0.695 [99% CL: 0.536: 0.902], p=0.0003). The primary endpoint results are robust, all sensitivity and supplementary analyses are in line with the primary analysis.

A relapse is defined as new, worsening or recurrent neurological symptoms that occur at least 30 days after the onset of a preceding relapse, and that last at least 24 hours, in the absence of fever or infection.

The new, worsening or recurrent neurological symptoms were evaluated by the treating neurologist and, if all the elements of the above definition were verified, and in the absence of another, better explanation of the subject's symptoms, the event was considered as a relapse. The onset date of the relapse corresponded to the onset date of the symptoms.

A relapse was confirmed by the treating neurologist only when the subjects' symptoms were accompanied by an increase in EDSS/FS (functional system) scores, which were consistent with the subject's symptoms, from a previous clinically stable EDSS/FS assessment (i.e., performed at least 30 days after the onset of any previous relapse), obtained by the efficacy assessor and consistent with the following:

- An increase of at least half a step (0.5 points; unless EDSS=0, then an increase of at least 1.0 points is required) or
- An increase of at least 1.0 point in at least two FS scores, or
- An increase of at least 2.0 points in at least one FS score (excluding bladder/bowel and cerebral).

The primary statistical analysis was performed up to EOS on the FAS using a negative binomial regression model for confirmed relapses, with treatment as a factor and the binary stratification variables (EDSS≤3.5 versus EDSS>3.5; DMTs within last 2 years prior to randomization [Yes/No]) and the number of relapses in the year prior to study entry (categories≤1 (or missing) and >2) included in the model. The model also included an offset variable defined as the log of time on study (in years) from randomization up to EOS.

Ponesimod 20 mg statistically significantly reduced ARR (confirmed relapses) up to EOS by 30.5% compared to teriflunomide 14 mg (ARR=0.202 for ponesimod 20 mg vs. 0.290 for teriflunomide 14 mg, rate ratio: 0.695 [99% CL: 0.536; 0.902], p=0.0003).

Figure 7:
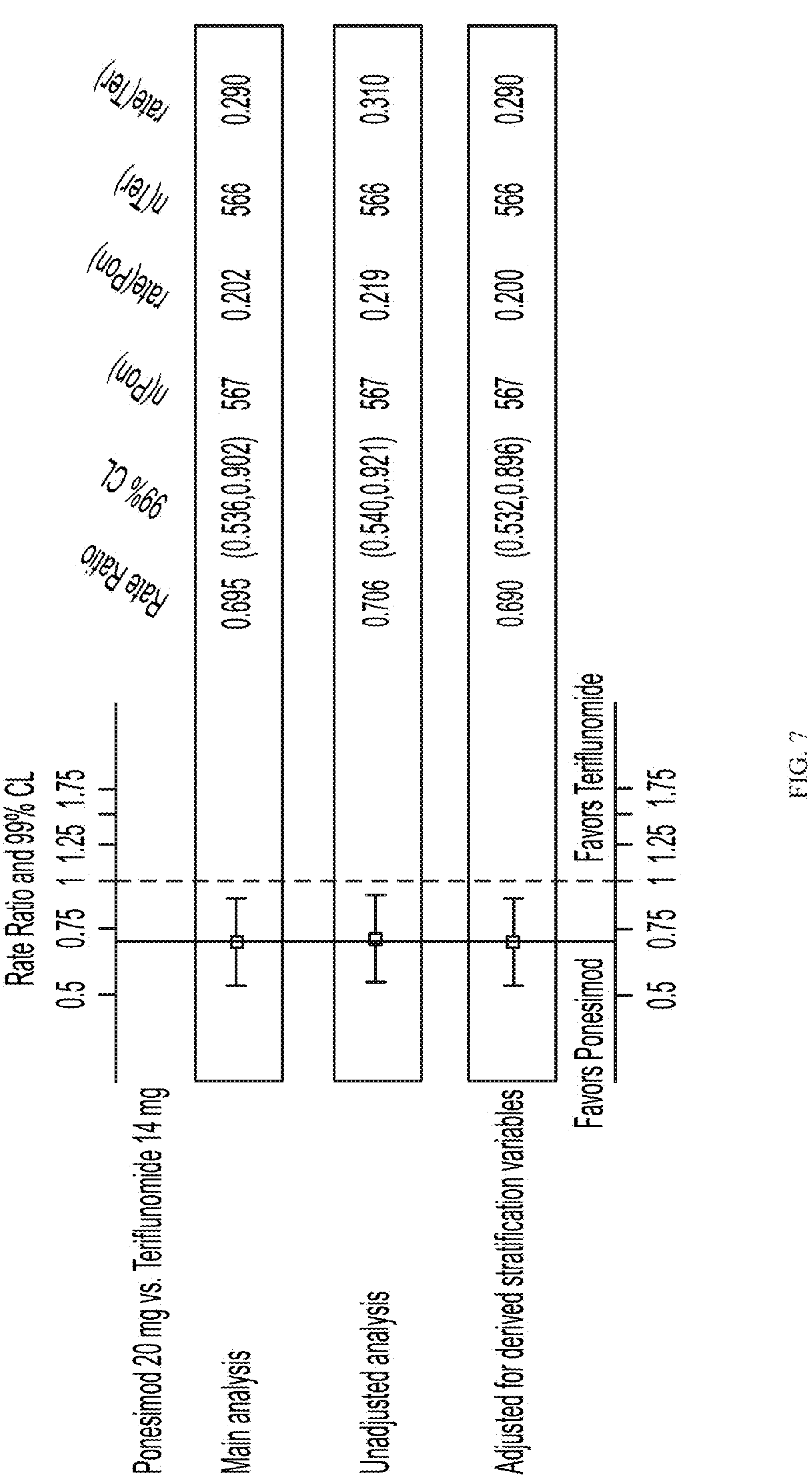
FIG. 7 is a Forest plot (with 99% CL) showing an overview of primary and sensitivity analyses for confirmed relapses up to EOS (Analysis Set: Full Analysis Set).
Figure 8:
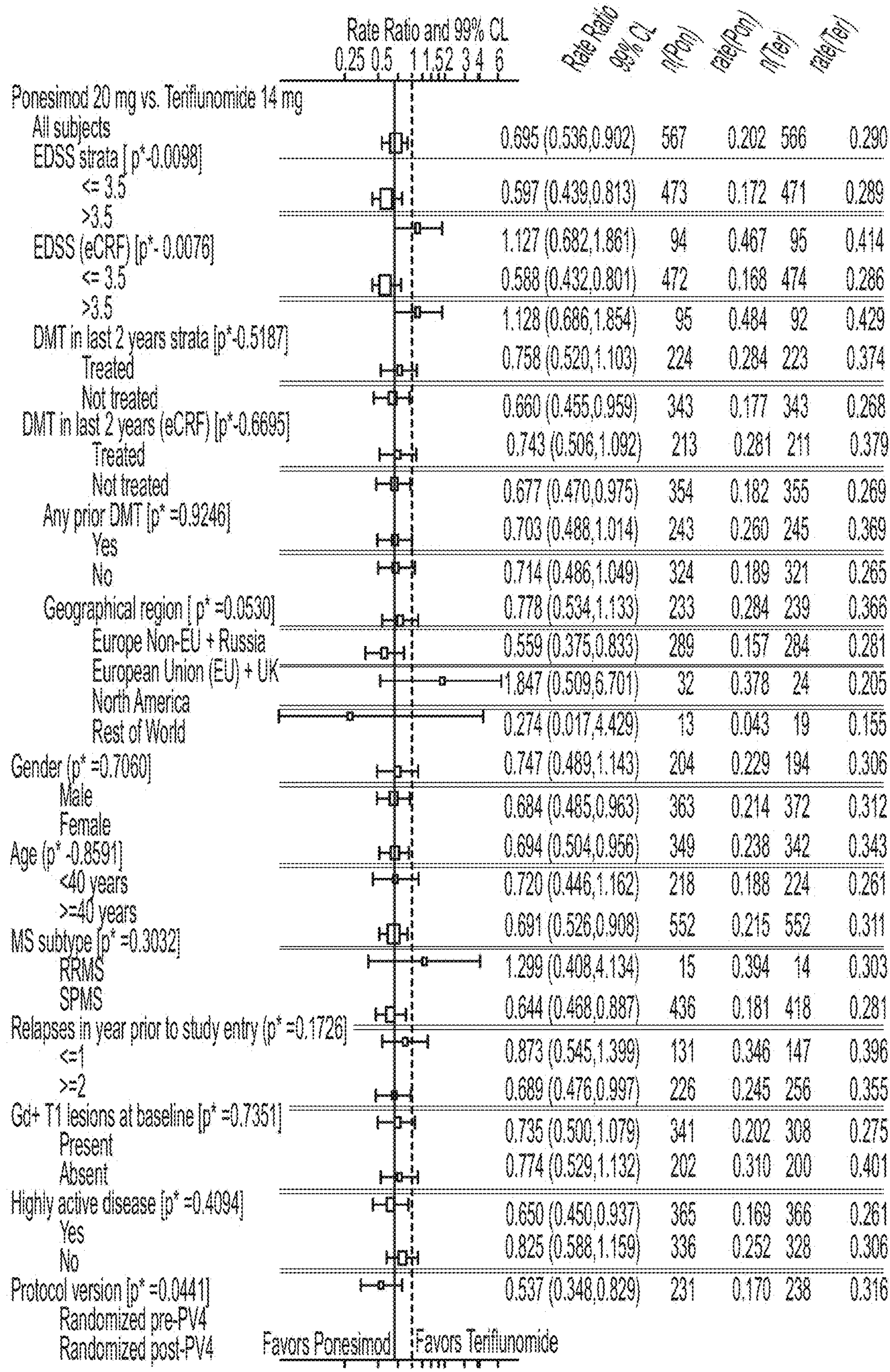
FIG. 8 is a Forest plot (with 99% CL) showing subgroup analyses of confirmed relapses up to EOS (Analysis Set: Full Analysis Set).

The primary endpoint results were robust; all sensitivity (see FIG. 7) and supplementary analyses (see FIG. 2A) are in line with the primary analysis. Subgroup analysis [see FIG. 8], shows most notably that there appears to be a treatment-by-EDSS stratum interaction.

TABLE 6

| Confirmed relapses up to EOS - ARR from negative binomial regression (Primary analysis)<br>Analysis Set: Full Analysis Set | | |
|---|---|---|
| | Ponesimod<br>20 mg<br>N = 567 | Teriflunomide<br>14 mg<br>N = 566 |
| Mean estimate (ARR) | 0.202 | 0.290 |
| 99% CL | (0.165, 0.246) | (0.244, 0.345) |
| 95% CL | (0.173, 0.235) | (0.254, 0.331) |
| Treatment effect (rate ratio) | 0.695 | |
| 99% CL | (0.536, 0.902) | |

TABLE 6-continued

| Confirmed relapses up to EOS - ARR from negative binomial regression (Primary analysis) Analysis Set: Full Analysis Set | | |
|---|---|---|
| | Ponesimod 20 mg N = 567 | Teriflunomide 14 mg N = 566 |
| 95% CL | (0.570, 0.848) | |
| p-value | 0.0003 | |
| Dispersion estimate | 0.765 | |
| Number of subjects included in analysis | 567 | 566 |
| Total number of relapses | 242 | 344 |
| Total time (years) | 1119 | 1137 |
| Raw ARR | 0.216 | 0.303 |

3. Secondary Endpoint(s) Main Analyses 3.1 Fatigue—Change from Baseline to Week 108 in FSIQ-RMS Weekly Symptoms Score Change from baseline to Week 108 in the FSIQ-RMS weekly symptoms score, based on the full analysis set, was statistically significantly lower in the ponesimod 20 mg arm compared with teriflunomide 14 mg, based on an MMRM analysis (mean=−0.01 for ponesimod 20 mg vs. 3.56 for teriflunomide 14 mg, mean difference: −3.57 [95% CL: −5.83: −1.32], p=0.0019, an increase from baseline indicates worsening in fatigue symptoms). See FIG. 3A.

Figure 3B:
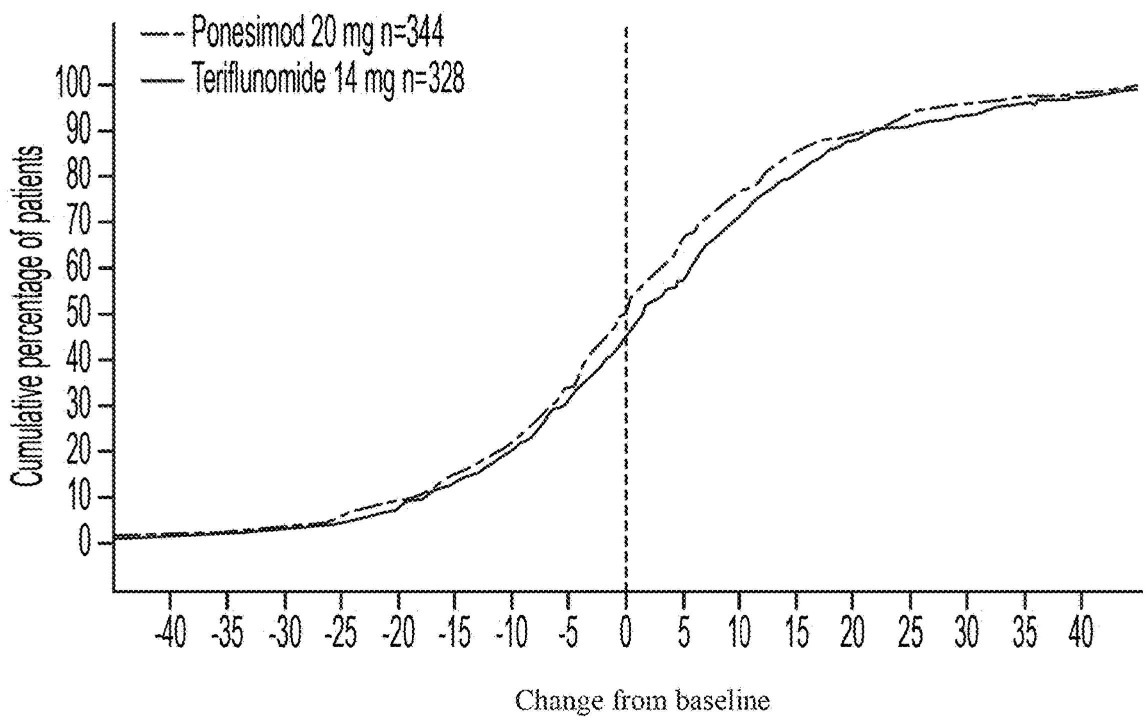
FIG. 3B shows cumulative distribution function of change from baseline at week 108 for the FSIQ-RMS weekly symptoms score.

Cumulative distribution function of change is shown in FIG. 3B. Results of the study are summarized below in Table 6A. In addition to the observation of statistical significance at the group level change from baseline favoring ponesimod, there is also observed a statistically significant difference in patients who were stable or improved on ponesimod compared to teriflunomide. This suggests a statistically significant and clinically meaningful difference for ponesimod at the patient level.

TABLE 6A

Summary of Change from Baseline to Week 108 for FSIQ-RMS Weekly Symptoms Score Based on Full Analysis Set.

| Visit | Change in FSIQ-RMS-S: Total Score | N | Ponesimod | N | Teriflunomide | P-Value |
|---|---|---|---|---|---|---|
| Week 108 | Improved (<−6.3) | 105 | 30.5% | 98 | 29.9% | 0.5163 |
| | Stable (−6.3 < x < +6.3) | 132 | 38.4% | 107 | 32.6% | |
| | Stable or Improved | 237 | 68.9% | 205 | 62.5% | 0.045 |
| | Worsened (≥6.3) | 107 | 31.1% | 123 | 37.5% | |

The FSIQ-RMS is an MS specific 20-item PRO measure that comprises 2 domains: one measuring MS symptoms and one measuring MS-related impacts. The symptoms domain of the scale was used in this study to compare the effect of ponesimod and teriflunomide on fatigue. This new tool has a number of advantages compared to the available fatigue tools for MS. See Hudgens S, et al., *Development and Validation of the FSIQ-RAS: A New Patient-Reported Questionnaire to Assess Symptoms and Impacts of Fatigue in Relapsing Multiple Sclerosis. Value Health.* 2019 April; 22(4):453-466. doi: 10.1016/j.jval.2018.11.007. Epub 2019 Feb. 21. PubMed PMID: 30975397. With 7 symptom items and 13 impact items (in 3 impacts subdomains: physical, cognitive and emotional, and coping), the FSIQ-RMS is a comprehensive, valid, and reliable measure of fatigue-related symptoms and impacts in RMS patients.

The FSIQ-RMS symptom domain (FSIQ-RMS-S) consists of seven items assessing fatigue-related symptoms with a recall period of 24 hours measured on an 11-point numeric rating scale; the standardized symptom domain score ranges from 0 to 100 with a higher score indicating greater fatigue. This domain (i.e., section 1 of the questionnaire) is completed on 7 consecutive days.

The FSIQ-RMS impact domain (FSIQ-RMS-1) consists of 13 items assessing impacts of fatigue-related symptoms with a recall period of 7 days measured on a 5-point verbal descriptor scale, ranging from no impact to extreme impact; the impact domain score ranges from 0 to 100 with a higher score indicating greater impact. As the impact domain of the FSIQ-RMS (i.e., section 2 of the questionnaire) has a 7-day recall period, it was completed on the last day (i.e., seventh day) of completion of section 1.

FSIQ-RMS was completed during the pre-randomization period, at Visits 6, 7, 10, and 12 (Weeks 12, 24, 60, 84), 14 (EOT), and at unscheduled visits due to relapses (R1, R2, etc.) or other unscheduled visits (U1, U2, etc.) as described below. If applicable, FSIQ-RMS was performed at the corresponding visits in the PTOP.

The completion of the FSIQ-RMS during the pre-randomization period was done as follows: At Visit 1 (Screening), subjects who appear eligible based on the assessments made during this visit (but prior to the results from the laboratory assessments are received) were provided with the electronic device containing the FSIQ-RMS.

Once the results from the laboratory assessments confirmed the subject's eligibility, and provided no other assessment performed in the meantime excluded the subject, the site coordinator contacted and asked the subject to start the completion of the FSIQ-RMS. At home, the subject completed the symptom domain of the FSIQ-RMS for 7 days (i.e., section 1 of the questionnaire). On the seventh day, the subject completed the impact domain of the FSIQ-RMS (i.e., section 2 of the questionnaire). The information captured from this assessment was used as the baseline data for the FSIQ-RMS. Ideally, the FSIQ-RMS was completed during the 7 consecutive days preceding the randomization.

After randomization, the symptoms domain of the FSIQ-RMS (i.e., section 1 of the questionnaire) was completed by the subject at home on a daily basis, starting in the evening of the day of a visit when the FSIQ-RMS was administered (Day 1 of questionnaire administration cycle) and during the 6 subsequent days (i.e., over 7 days in total). Subjects returned the completed FSIQ-RMS diary at the next scheduled visit. On the seventh day, the subject completed the impact domain of the FSIQ-RMS (i.e., section 2 of the questionnaire). If applicable, at the end of the PTOP, the FSIQ-RMS was completed prior to Visit 14A (Week 108), ideally, during the 7 consecutive days preceding the visit.

Results for the secondary endpoint of change from baseline to Week 108 in the symptoms domain of the FSIQ-RMS (assessed over a 7-day period) have shown the superiority of ponesimod 20 mg over teriflunomide 14 mg.

3.2 MRI—Combined Unique Active Lesions (CUAL) from Baseline to Week 108.

CUAL are new Gd+T1 lesions plus new or enlarging T2 lesions (without double-counting of lesions).

The cumulative number of CUAL is considered a reliable outcome measure of inflammatory MS disease activity. Radiological evidence of disease activity is routinely used to support disease diagnosis and to inform therapeutic decisions targeting no evidence of disease activity (NEDA), clinical (relapses or disability accumulation) or radiological (brain lesions on MRI) perspective. See Lublin F D. *Disease activity free status in MS.* Mult Scler Relat Disord. 2012 January; 1(1):6-7. doi: 10.1016/j.msard.2011.08.001. Epub 2011 Aug. 27. PubMed PMID: 25876444.

MRI scans were performed at Visits 2 (Baseline). 10 (Week 60), and 14 (EOT) and at any unscheduled visit (U1, U2, etc.). If applicable, MRI scans also were performed at the corresponding visits in the PTOP (Visits 10A and 14A). Testing at all visits were performed up to 7 days prior to or after the visit date. In case of premature study treatment discontinuation, the MRI at EOT did not need to be performed if the EOT visit occurred within less than 4 weeks of the MRI assessment at Visit 10 (Week 60).

MRI variables included the number and volume of new and total Gd+ lesions on T1-weighted MRI scans, number of new and enlarging lesions and lesion volume on T2-weighted MRI, and global measures of loss of brain tissue.

Lesion count of MRI performed within 24 months prior to the study were recorded on the MS history page of the eCRF. These scans were not analyzed by the medical image analysis center (MIAC).

T1-weighted imaging before and after i.v. administration of 0.1 mmol/kg body weight (=0.2 mL/kg) of Gd as well as PD-T2-weighted imaging was performed. Gd may cause nausea and vomiting and in very rare cases allergic reactions that could require immediate anti-anaphylactic therapy (such as steroids, epinephrine/adrenaline, etc.).

Ponesimod 20 mg statistically significantly reduced by 56% the number of CUALs between baseline and week 108 compared to teriflunomide 14 mg (mean CUALs per year=1.405 for ponesimod 20 mg vs. 3.164 for teriflunomide 14 mg, rate ratio: 0.44 [95% CL: 0.36: 0.54], p<0.0001). A total of 4.9% and 4.9% of subjects had a baseline but no post-baseline MRI; sensitivity analyses using a range of methods (data not shown) for imputation of missing data supported the primary results (p<0.0001 in all cases).

Ponesimod 20 mg was clearly superior in reducing the number of CUALs vs teriflunomide 14 mg, fully supporting and complementing the results of the primary endpoint.

TABLE 7

CUAL from baseline to Week 108 - negative binomial regression of lesions per year (Main analysis)
Analysis Set: Full Analysis Set

| | Ponesimod 20 mg N = 567 | Teriflunomide 14 mg N = 566 |
|---|---|---|
| Mean estimate (Lesions per year) | 1.405 | 3.164 |
| 95% CL | (1.215, 1.624) | (2.757, 3.631) |
| Treatment effect (Rate Ratio) | 0.444 | |
| 95% CL | (0.364, 0.542) | |
| p-value | <.0001 | |
| Dispersion estimate | 2.409 | |
| Number of subjects included in analysis | 539 | 536 |
| Total number of lesions | 1671 | 3714 |
| Total time (years) | 1072 | 1067 |
| Raw mean lesions/year | 1.559 | 3.481 |

TABLE 7-continued

Mean estimate = CUAL per year, Rate Ratio: ponesimod vs. teriflunomide.
Negative binomial model is applied with Wald confidence intervals and p-value.
Offset: Log Time (years) up to last MRI scan.
Covariates: EDSS strata (<=3.5, >3.5), DMT within last 2 years prior to randomization strata (Y, N), and Gd+ T1 lesions at baseline (absent or present).
Subjects with baseline and at least one post-baseline MRI are included in the analysis.

3.3 EDSS—Time to First 12-Week Confirmed Disability Accumulation (CDA) ICOT

The 12-week confirmed disability accumulation, also sometimes referred to as disability progression (CDA/CDP) is a common endpoint in RMS studies, while 24-week CDA/CDP is regarded as the more robust and clinically relevant endpoint. % ee European Medicines Agency, *Guideline on clinical investigation of medicinal products for the treatment of Multiple Sclerosis,* 26 Mar. 2015. EMA/CHMP/771815/2011, Rev. 2, Committee for Medicinal Products for Human Use (CHIMP). Teriflunomide 14 mg has shown a statistically significant reduction in the risk of 12-week CDP in the TEMSO and TOWER studies. See O'Connor P, et al. N Engl J Med. 2011; 365:1293-30. Confavreux C. et al., *TOWER Trial Group, Oral ter teriflunomide patients with relapsing multiple sclerosis (TOWER): a randomised, double-blind, placebo-controlled, phase* 3 *trial*. Lancet Neurol. 2014 March; 13(3):247-56. doi: 10.1016/S1474-4422(13)70308-9. Epub 2014 Jan. 23. PubMed PMID: 24461574.

A 12-week CDA is an increase of at least 1.5 in EDSS for subjects with a baseline EDSS score of 0.0 or an increase of at least 1.0 in EDSS for subjects with a baseline EDSS score of 1.0 to 5.0, or an increase of at least 0.5 in EDSS for subjects with a baseline EDSS score≥5.5 which is to be confirmed after 12 weeks.

Baseline EDSS is defined as the last EDSS score recorded prior to randomization. The initial EDSS increase, meeting the above criteria, is defined as the onset of disability accumulation.

All EDSS measurements (with or without relapse, at a scheduled or unscheduled visit) were used to determine the onset of disability accumulation. However, EDSS scores used for confirmation of disability accumulation were obtained at a scheduled visit (i.e., unscheduled visits cannot be used as confirmatory visits) outside any ongoing relapse. In this context, relapse duration is defined as period between start and end dates if available and limited to 90 days from onset if end date is not available or duration is longer than 90 days.

In order to confirm that the EDSS increase is persistent, all EDSS measurements between the onset and the 12-week EDSS confirmation (minus 7-day visit time-window) need to show an increase in EDSS, meeting the criteria for accumulation of disability as defined above.

Figure 4:
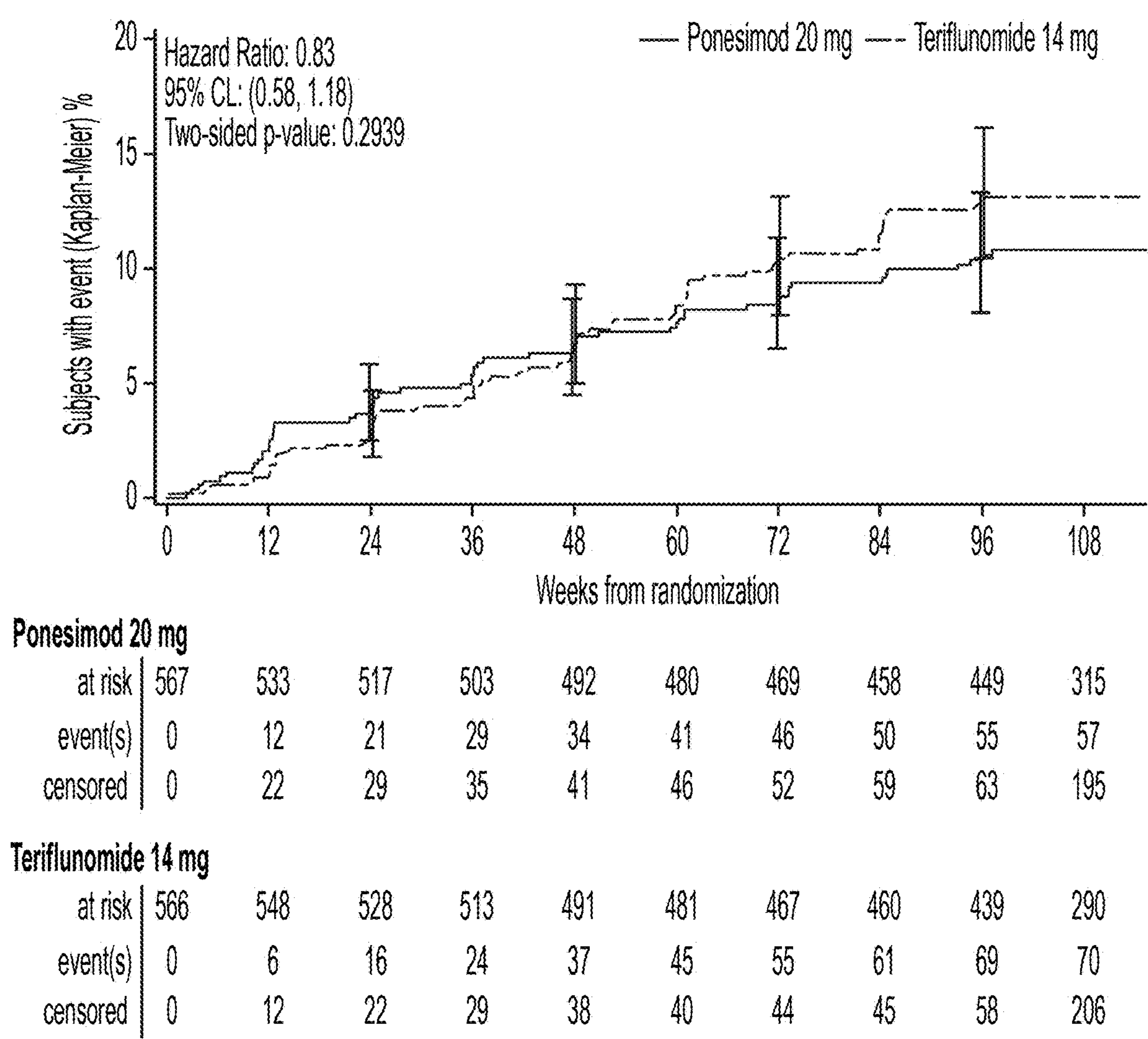
FIG. 4 is a Kaplan-Meier curve (main analysis) showing the time to first 12-week confirmed disability accumulation (CDA) up to end-of-study (EOS): Analysis Set: Full Analysis Set.

A 12-week CDA was observed in 10.1%, and 12.4% of subjects up to EOS in the ponesimod 20 mg and teriflunomide 14 mg arms, respectively. The risk of 12-week CDA was not found to be statistically significantly different for ponesimod 20 mg as compared with teriflunomide 14 mg (hazard ratio: 0.83 [95% CL, 0.58 to 1.18]; log-rank p=0.2939). Consequently, the formal testing procedure was stopped. See Table A3; see also FIG. 4.

TABLE A3

Testing strategy: Overview of secondary endpoint results
Analysis Set: Full Analysis Set

| Endpoint | Effect Measure | Estimate | 95% CL | Alpha available | p-value | Significant |
|---|---|---|---|---|---|---|
| FSIQ-RMS change from baseline to Week 108 | Mean difference | −3.57 | −5.83, −1.32 | 0.0167 | 0.0019 | Yes |
| CUAL from baseline to Week 108 | Rate ratio | 0.44 | 0.36, 0.54 | 0.0333 | <.0001 | Yes |
| Time to first 12-week CDA | Hazard ratio | 0.83 | 0.58, 1.18 | 0.0500 | 0.2939 | No |
| Time to first 24-week CDA | Hazard ratio | 0.84 | 0.57, 1.24 | 0.0000 | 0.3720 | NA |

CUAL = Combined unique active lesions;
CDA = Confirmed disability accumulation;
NA = Not applicable.
Effect measures display results of Ponesimod 20 mg vs. Teriflunomide 14 mg.
Alpha available = Alpha available as per testing strategy for testing the corresponding endpoint.

3.4 EDSS—Time to First 24-Week Confirmed Disability Accumulation (CDA)

Figure 5:
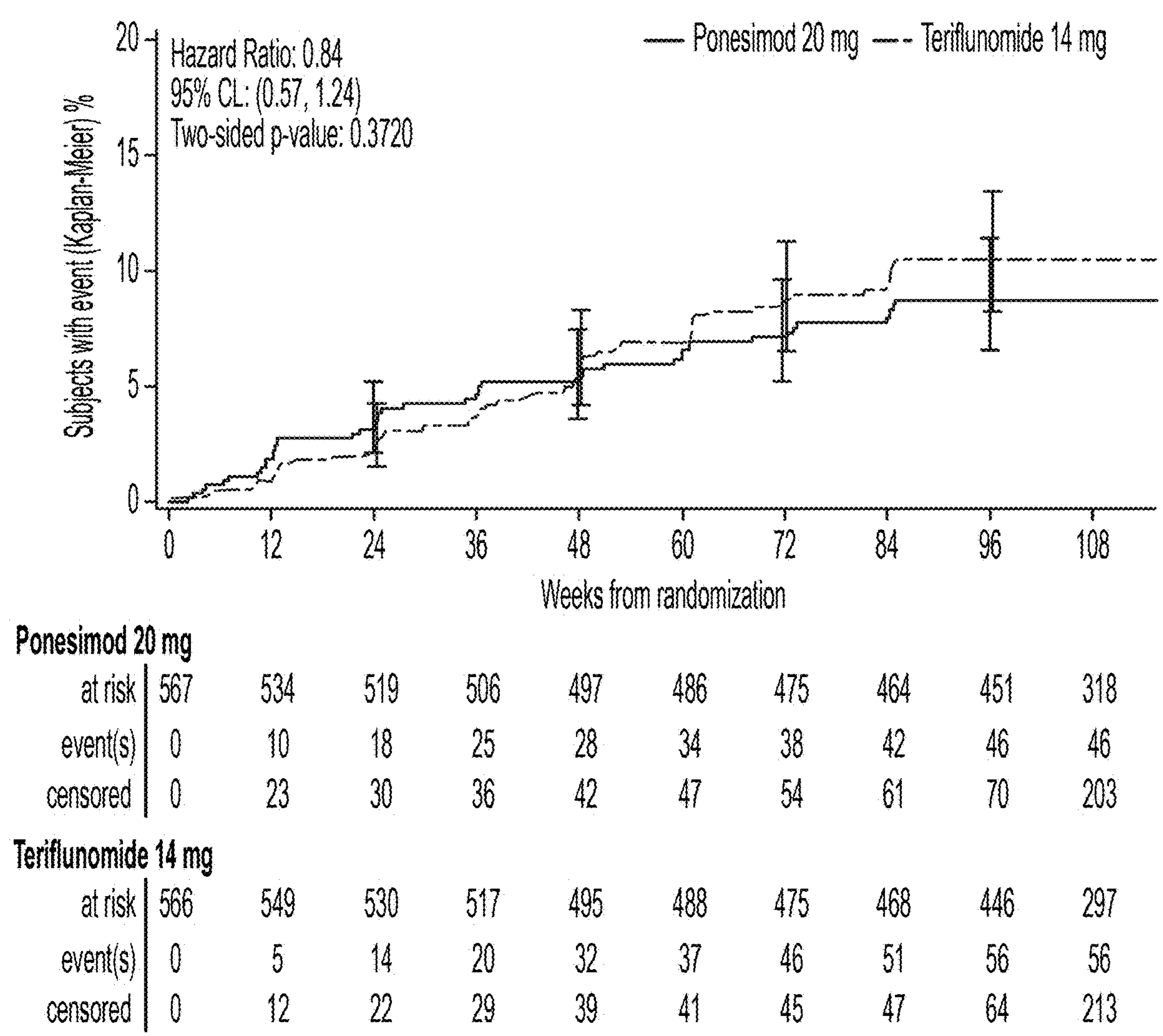
FIG. 5 is a Kaplan-Meier curve (Main analysis) showing the time to first 24-week CDA up to EOS: Analysis Set: Full Analysis Set.

24-week CDA was not formally tested and only evaluated in an exploratory manner. A 24-week CDA was observed in 8.1%, and 9.9% of subjects up to EOS in the ponesimod 20 mg and teriflunomide 14 mg arms, respectively. The risk of 24-week CDA for ponesimod 20 mg as compared with teriflunomide 14 mg was not found to be statistically significantly different at a nominal $\alpha=0.05$ (hazard ratio: 0.84|95% CL, 0.57 to 1.241; log-rank p=0.3720). See FIG. 5.

A 24-week CDA is an increase of at least 1.5 in EDSS for subjects with a baseline EDSS score of 0.0 or an increase of at least 1.0 in EDSS for subjects with a baseline EDSS score of 1.0 to 5.0, or an increase of at least 0.5 in EDSS for subjects with a baseline EDSS score≥5.5 which is to be confirmed after 24 weeks.

Baseline EDSS is defined as the last EDSS score recorded prior to randomization. The initial EDSS increase, meeting the above criteria, is defined as the onset of disability accumulation.

All EDSS measurements (with or without relapse, at a scheduled or unscheduled visit) were used to determine the onset of disability accumulation. However, EDSS scores used for confirmation of disability accumulation were obtained at a scheduled visit (i.e., unscheduled visits cannot be used as confirmatory visits) outside any ongoing relapse. In this context, relapse duration is defined as period between start and end dates if available and limited to 90 days from onset if end date is not available or duration is longer than 90 days.

In order to confirm that the EDSS increase is persistent, all EDSS measurements between the onset and the 24-week EDSS confirmation (minus 7-day visit time-window) need to show an increase in EDSS, meeting the criteria for accumulation of disability as defined above.

In this study, ponesimod 20 mg reduced by 17% and 16% the risk of 12- and 24-week CDA, respectively, compared to teriflunomide 14 mg, however the difference did not reach statistical significance. This study was not powered for 12- or 24-week CDA, so results were not bound to be statistically different.

4. Safety 4.1 Summary of all Adverse Events

An overview of treatment emergent AEs (TEAEs) is presented in Table 8.

TABLE 8

Overview of
treatment-emergent adverse events (AE)
Analysis Set: Safety Set

| Characteristic | Ponesimod 20 mg N = 565 n (%) | Teriflunomide 14 mg N = 566 n (%) |
|---|---|---|
| Subject with at least one | | |
| AE | 502 (88.8) | 499 (88.2) |
| Severe AE | 39 (6.9) | 26 (4.6) |
| Drug-Related AE | 278 (49.2) | 238 (42.0) |
| AE leading to study drug discontinuation | 49 (8.7) | 34 (6.0) |
| Serious AE | 49 (8.7) | 46 (8.1) |
| Fatal AE | 0 | 2 (0.4) |

Overall, the proportion of subjects who experienced at least one TEAE was similar in both treatment arms (88.8% and 88.2% of subjects in the ponesimod 20 mg and the teriflunomide 14 mg arms, respectively).

The most common TEAEs in the ponesimod 20 mg arm were ALT increased (19.5%), nasopharyngitis (19.3%), headache (11.5%) and upper respiratory tract infection (10.6%). The most common TEAEs in the ponesimod 20 mg arm were ALT increased (19.5% vs 9.4% in the teriflunomide arm), nasopharyngitis (19.3% vs 16.8%), headache (11.5% vs 12.7%) and upper respiratory tract infections (10.6% vs 10.4%).

TEAEs leading to premature treatment discontinuation were reported in 8.7% of ponesimod 20 mg subjects compared to 6.0% of teriflunomide 14 mg subjects [see Table 9]. While the number of events was low, the difference in the type of AEs leading to treatment discontinuation was mainly driven by anticipated class effects on respiratory system and macular edema. No infections led to permanent study treatment discontinuation in the study.

TABLE 9

Treatment-emergent AEs leading to premature discontinuation of study drug by SOC
Analysis Set: Safety Set

| System Organ Class | Ponesimod 20 mg N = 565 n (%) | Teriflunomide 14 mg N = 566 n (%) |
|---|---|---|
| Subjects with at least one AE | 49 (8.7) | 34 (6.0) |
| Investigations | 12 (2.1) | 10 (1.8) |
| Respiratory, thoracic and mediastinal disorders | 7 (1.2) | 0 |
| Eye disorders | 5 (0.9) | 0 |
| Gastrointestinal disorders | 4 (0.7) | 4 (0.7) |
| Blood and lymphatic system disorders | 3 (0.5) | 2 (0.4) |
| General disorders and administration site conditions | 3 (0.5) | 2 (0.4) |
| Hepatobiliary disorders | 3 (0.5) | 2 (0.4) |
| Pregnancy, puerperium and perinatal conditions | 3 (0.5) | 3 (0.5) |
| Vascular disorders | 3 (0.5) | 0 |
| Nervous system disorders | 2 (0.4) | 4 (0.7) |
| Social circumstances | 2 (0.4) | 1 (0.2) |
| Cardiac disorders | 1 (0.2) | 2 (0.4) |
| Musculoskeletal and connective tissue disorders | 1 (0.2) | 1 (0.2) |
| Neoplasms benign, malignant and unspecified (incl cysts and polyps) | 1 (0.2) | 1 (0.2) |
| Psychiatric disorders | 1 (0.2) | 1 (0.2) |
| Skin and subcutaneous tissue disorders | 1 (0.2) | 2 (0.4) |
| Reproductive system and breast disorders | 0 | 1 (0.2) |
| Surgical and medical procedures | 0 | 1 (0.2) |

System Organ Classes are based on MedDRA version 21.0.
SOCs are sorted by descending order of frequency in the ponesimod arm.

There were two deaths reported in the study, one due to coronary artery insufficiency and one due to multiple sclerosis. Both deaths occurred in subjects receiving teriflunomide 14 mg.

The proportion of subjects who experienced at least one SAE was similar in both treatment arms (8.7% and 8.1% of subjects in the ponesimod 20 mg and the teriflunomide 14 mg arms, respectively).

An overview of AEs of special interest (AESIs) addressing anticipated risks of ponesimod is presented in Table 10. The most common AESIs were reported for category hepatobiliary disorders/liver enzyme abnormality (25.7% vs 14.5% in ponesimod 20 mg compared to teriflunomide 14 mg, respectively), followed by category hypertension (10.1% vs 9.0%), and pulmonary events (8.0% vs 2.7%).

TABLE 10

Treatment-emergent AESIs by category
Analysis Set: Safety Set

| AESI Category | Ponesimod 20 mg N = 565 n (%) | Teriflunomide 14 mg N = 566 n (%) |
|---|---|---|
| Hepatobiliary disorders/Liver enzyme abnormality | 145 (25.7) | 82 (14.5) |
| Hypertension | 57 (10.1) | 51 (9.0) |
| Pulmonary events | 45 (8.0) | 15 (2.7) |
| Effect on heart rate and rhythm (including aypotension) | 29 (5.1) | 24 (4.2) |
| Herpetic infection | 27 (4.8) | 27 (4.8) |
| Infection | 9 (1.6) | 5 (0.9) |
| Seizure | 8 (1.4) | 1 (0.2) |

TABLE 10-continued

Treatment-emergent AESIs by category
Analysis Set: Safety Set

| AESI Category | Ponesimod 20 mg N = 565 n (%) | Teriflunomide 14 mg N = 566 n (%) |
|---|---|---|
| Macular edema | 6 (1.1) | 1 (0.2) |
| Skin malignancy | 5 (0.9) | 1 (0.2) |
| Non-skin malignancy | 1 (0.2) | 1 (0.2) |

Categories are sorted by descending order of frequency in the ponesimod 20 mg arm.
AESI - Adverse Event of Special Interest.
Infection AESI are identified by the AEs from the Infections and Infestations SOC, only if reported as serious or severe.

The proportion of subjects who experienced ALT increase >3×ULN was higher in the ponesimod arm (17.3%) compared to teriflunomide (8.3%) whereas ALT increase >8×ULN was higher in the teriflunomide arm (2.1%) compared to ponesimod (0.7%). Based on the individual case review, most ALT/AST increases ≥3×ULN occurred as a single transient asymptomatic episode, resolving with continued treatment or after protocol mandated treatment discontinuation. All but one case of bilirubin increase ≥2×ULN occurred in subjects with pre-treatment bilirubin increases. One case of potential Hy's law occurred in a subject with pre-existing transaminase elevation (ALT>5×ULN), and the event fully resolved within 2 weeks after treatment discontinuation.

The incidence of treatment-emergent heart rate and rhythm (including hypotension) AESIs on Day 1 was higher in the ponesimod 20 mg arm (2.1%) than in the teriflunomide 14 mg arm (0.4%). See Table 10A. However, the overall incidence of first dose AESI on Day 1 was low (2.1%) in ponesimod. None of these events were serious nor led to permanent discontinuation of study treatment. Discharge criteria at 4 hours post-dose were met for ca. 99% of subjects. No 2nd or higher degree AV block was observed. ECG HR effect: nadir at 2 hours post-dose (siponimod—3-4 hours, fingolimod—around by 6 hours). Low incidence of low HR outliers (post-dose HR≤40 bpm), all 3 of them with a pre-treatment HR of <55 bpm, which is a known risk factor for post-dose bradycardia with SIP receptor modulators.

Figure 6:
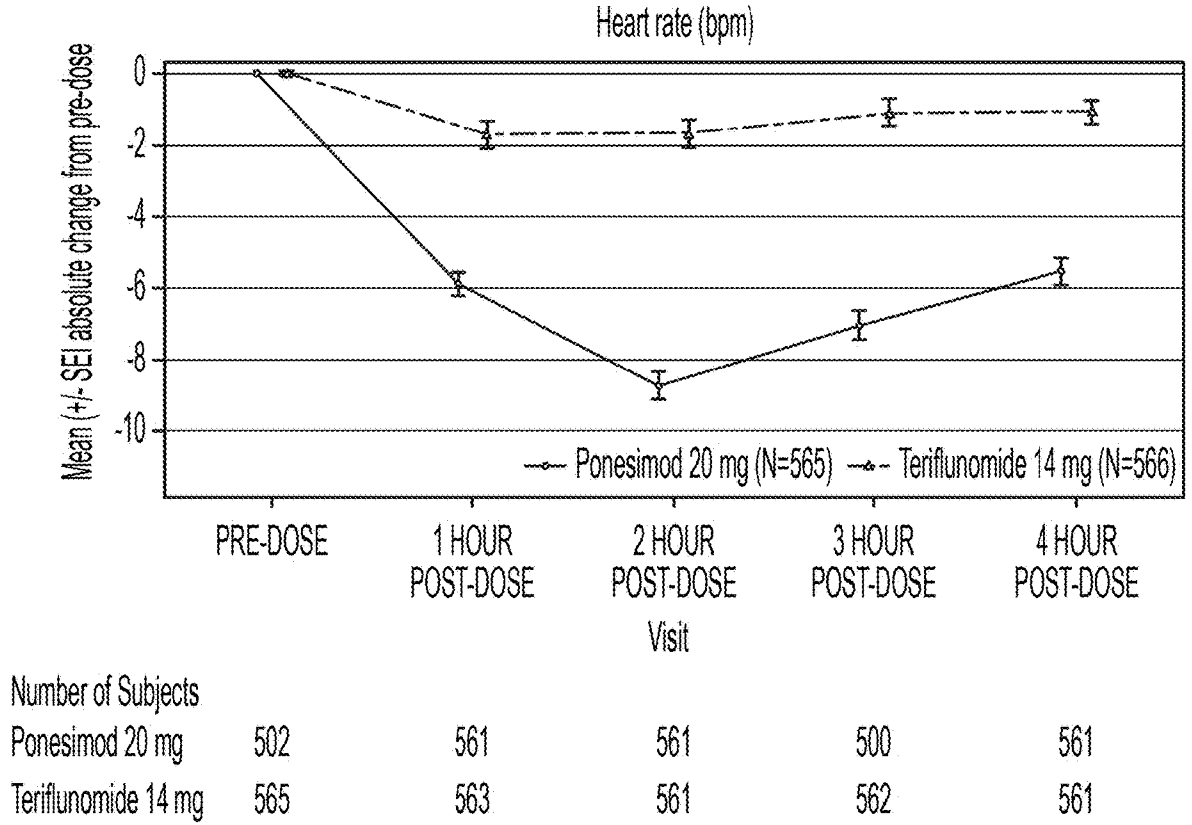
FIG. 6 shows the 12-lead electrocardiogram (ECG) heart rate and absolute change from pre-dose at Day 1, by hour (Analysis Set: Safety Set). As per up-titration regimen, the dose of ponesimod on Day 1 is 2 mg.

The mean heart rate reduction compared to pre-dose reached a maximum for ponesimod 20 mg at 2-hours post dose, −8.7 bpm compared to −1.7 bpm for teriflunomide 14 mg (FIG. 6). There were 3 subjects with asymptomatic post-dose HR≤40 bpm in the ponesimod 20 mg arm (none on teriflunomide 14 mg); all of these subjects had a pre-treatment HR<55 bpm, which would require post-dose monitoring according to regulatory precedence of siponimod [Mayzent® USPI].

TABLE 10A

Treatment-emergent AESI by PT: Effect on heart rate and rhythm (including hypotension) on Day 1
Analysis Set: Safety Set

| Preferred Term | Ponesimod 20 mg N = 565 n (%) | Teriflunomide 14 mg N = 566 n (%) |
|---|---|---|
| Subjects with at least one AE | 12 (2.1) | 2 (0.4) |
| Bradycardia | 4 (0.7) | 0 |
| Atrioventricular block first degree | 3 (0.5) | 0 |
| Defect conduction intraventricular | 2 (0.4) | 0 |
| Bundle branch block left | 1 (0.2) | 0 |

TABLE 10A-continued

Treatment-emergent AESI by PT: Effect on heart rate and rhythm (including hypotension) on Day 1
Analysis Set: Safety Set

| Preferred Term | Ponesimod 20 mg N = 565 n (%) | Teriflunomide 14 mg N = 566 n (%) |
|---|---|---|
| Bundle branch block right | 1 (0.2) | 0 |
| Sinus arrhythmia | 1 (0.2) | 0 |
| Sinus bradycardia | 1 (0.2) | 0 |
| Electrocardiogram QT prolonged | 0 | 1 (0.2) |
| Presyncope | 0 | 1 (0.2) |

Preferred Terms are based on MedDRA version 21.0.
Preferred terms are sorted by descending order of frequency in the ponesimod arm.
AESI - Adverse Event of Special Interest Example 1A: FSIQ-RMS and Physical, Cognitive, and Coping Impact Change from baseline to Week 108 for the physical, cognitive/emotional and coping impacts sub-domains of FSIQ-RMS are shown in FIG. 9, FIG. 10 and FIG. 11, respectively.

Figure 9:
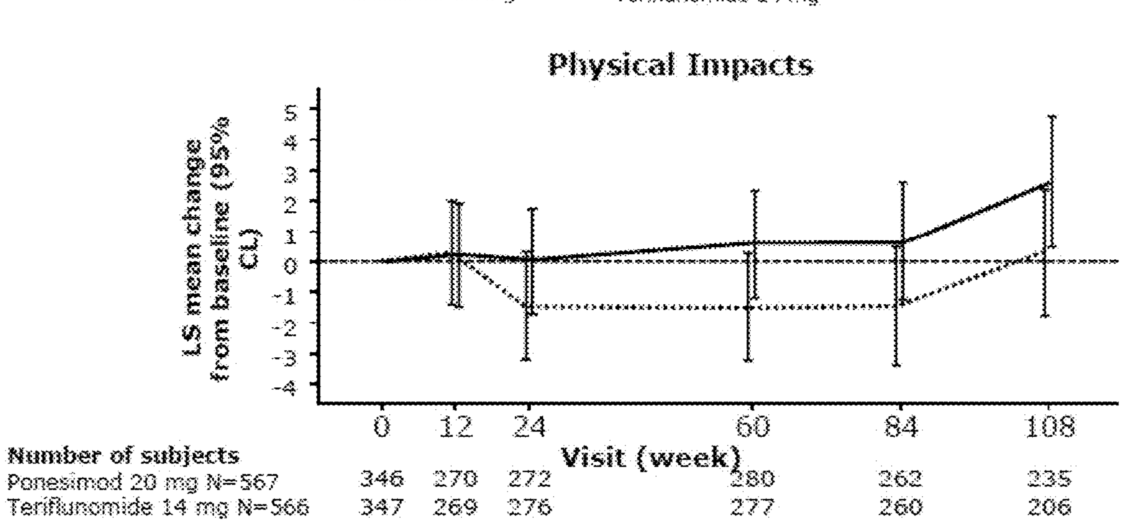
FIG. 9 shows change from baseline to week 108 in the FSIQ-RMS for the physical impact sub-domain.
Figure 10:
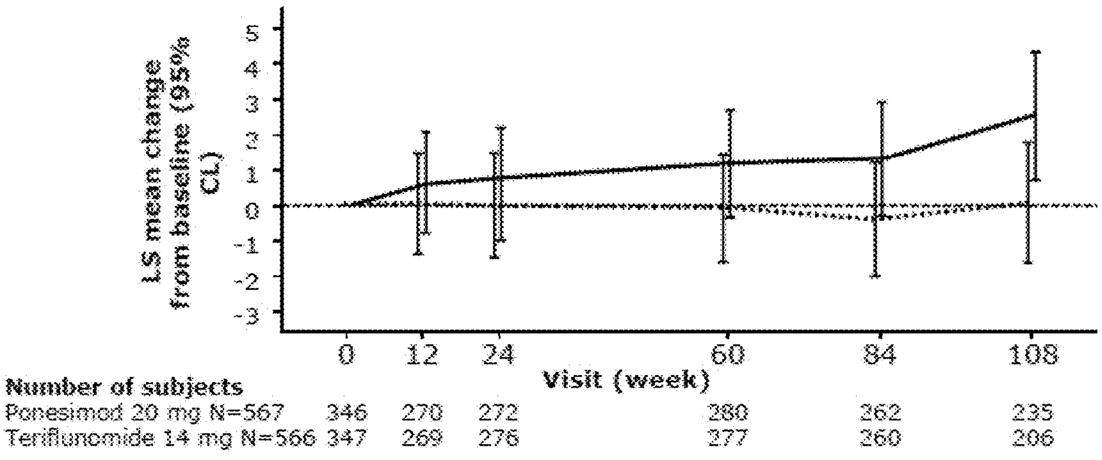
FIG. 10 shows change from baseline to week 108 in the FSIQ-RMS for the cognitive/emotional impacts sub-domain.
Figure 11:
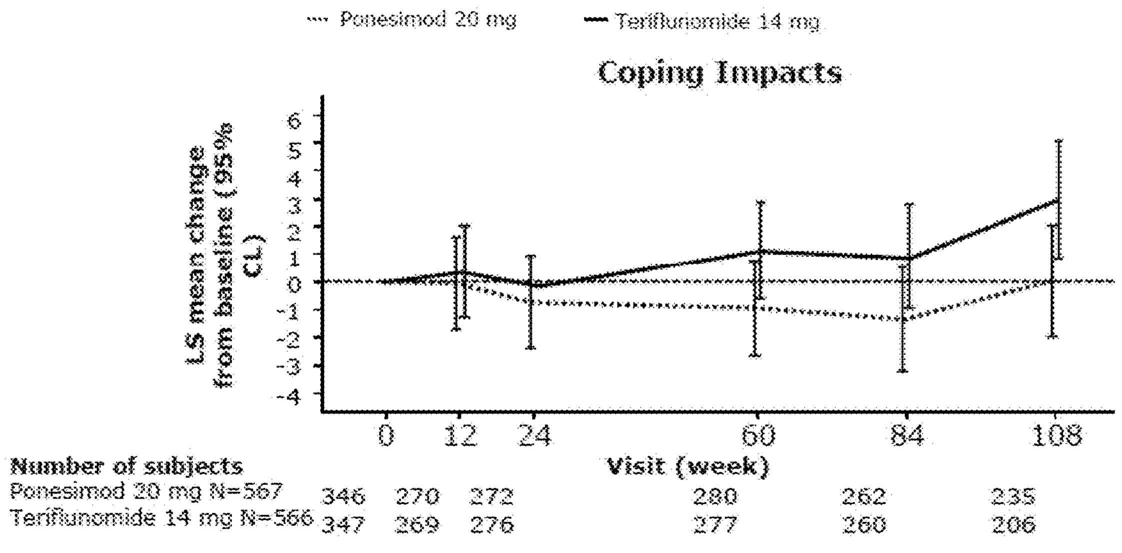
FIG. 11 shows change from baseline to week 108 in the FSIQ-RMS for the coping impact sub-domain.

FIGS. 9, 10 and 11 show the FSIQ-RMS physical, cognitive/emotional and coping impacts sub-domains at the group level, based on the full analysis set, for the ponesimod 20 mg treatment arm and the teriflunomide 14 mg treatment arm.

Example 1B: Change from Baseline to Week 108—Baseline Fatigue Below the Median

Figure 12:
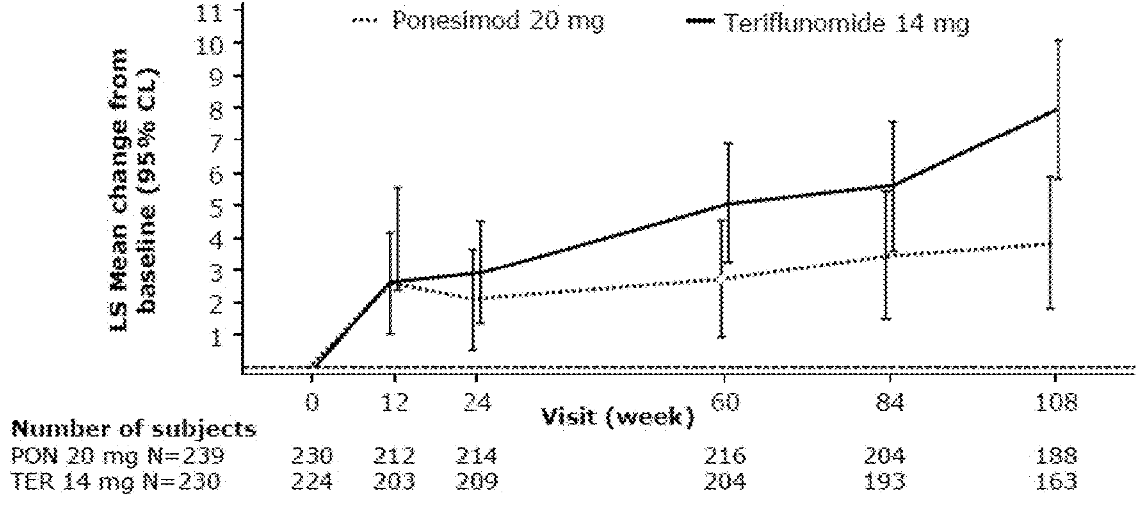
FIG. 12 shows change from baseline to week 108 in FSIQ-RMS weekly symptoms score for patients with baseline fatigue below the median.
Figure 13:
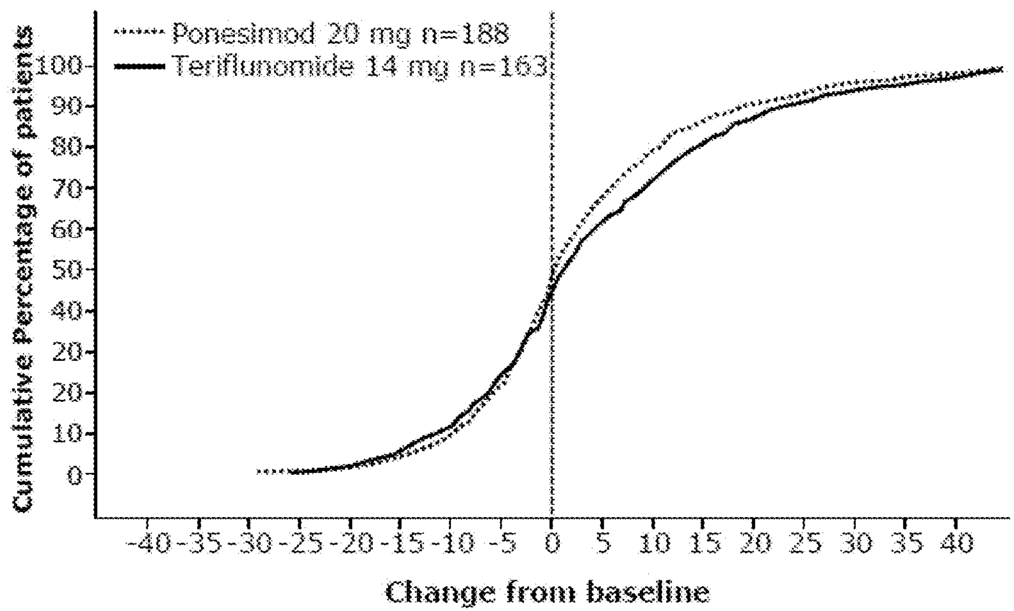
FIG. 13 shows cumulative distribution function of change from baseline at week 108 in FSIQ-RMS weekly symptoms score for patients with baseline fatigue below the median.

Mean change from baseline to Week 108 in FSIQ-RMS weekly symptoms score for patients with baseline fatigue below the median is shown in FIG. 12. Cumulative distribution function of change is shown in FIG. 13. Results are summarized in Table 11A below. Baseline fatigue (i.e., weekly symptoms score at baseline) is provided in Table 11B and was used for the baseline fatigue below the median in this Example and the baseline fatigue above the median in Example 1C.

Almost 65% of low baseline fatigue patients remained stable or improved over the 108 weeks on ponesimod, as compared to about 55% over the 108 weeks on teriflunomide.

TABLE 11A

Change From Baseline to Week 108, Baseline Fatigue Below the Median for Ponesimod and Teriflunomide

| Visit | Change From Baseline to Week 108: Baseline Fatigue Below the Median | N | Ponesimod | N | Teriflunomide | P-Value |
|---|---|---|---|---|---|---|
| WEEK 108 | Improved (<−6.3) | 36 | 19.1% | 34 | 20.9% | 0.736 |
| | Stable (−6.3 < x < +6.3) | 85 | 45.2% | 55 | 33.7% | |
| | Stable or Improved | 121 | 64.4% | 89 | 54.6% | 0.088 |
| | Worsened (≥6.3) | 67 | 35.6% | 74 | 45.4% | |

TABLE 11B

Baseline fatigue (symptoms score of FSIQ at baseline).

| | Ponesmiod | Teriflunomide |
|---|---|---|
| Minimum | 0.0 | 0.0 |
| Q1 | 14.49 | 17.93 |
| Median | 30.41 | 30.71 |
| Q3 | 46.33 | 46.33 |
| Maximum | 95.40 | 88.40 |

Example 1C: Change from Baseline to Week 108—Baseline Fatigue Above the Median

Figure 14:
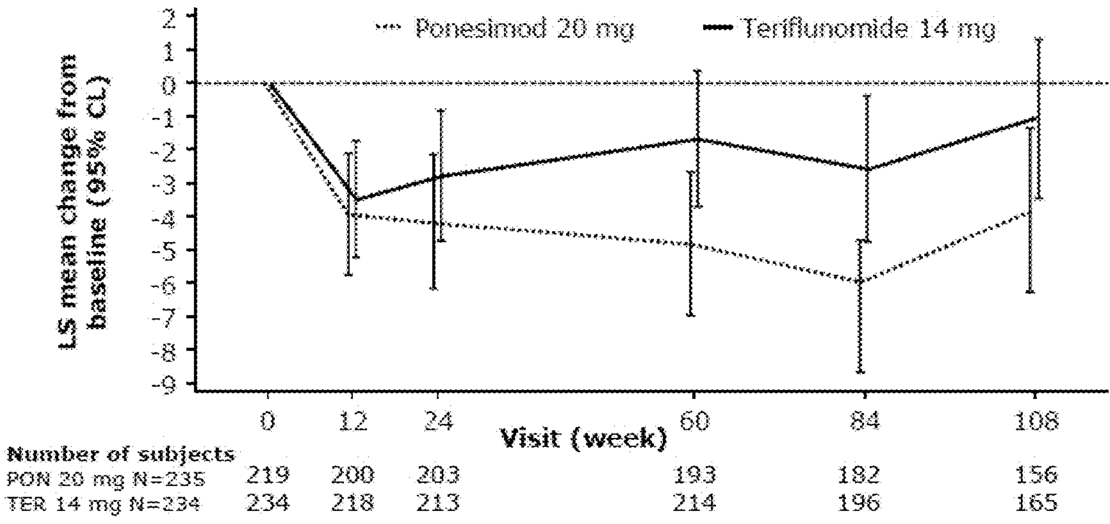
FIG. 14 shows change from baseline to week 108 in FSIQ-RMS weekly symptoms score for patients with baseline fatigue above the median.
Figure 15:
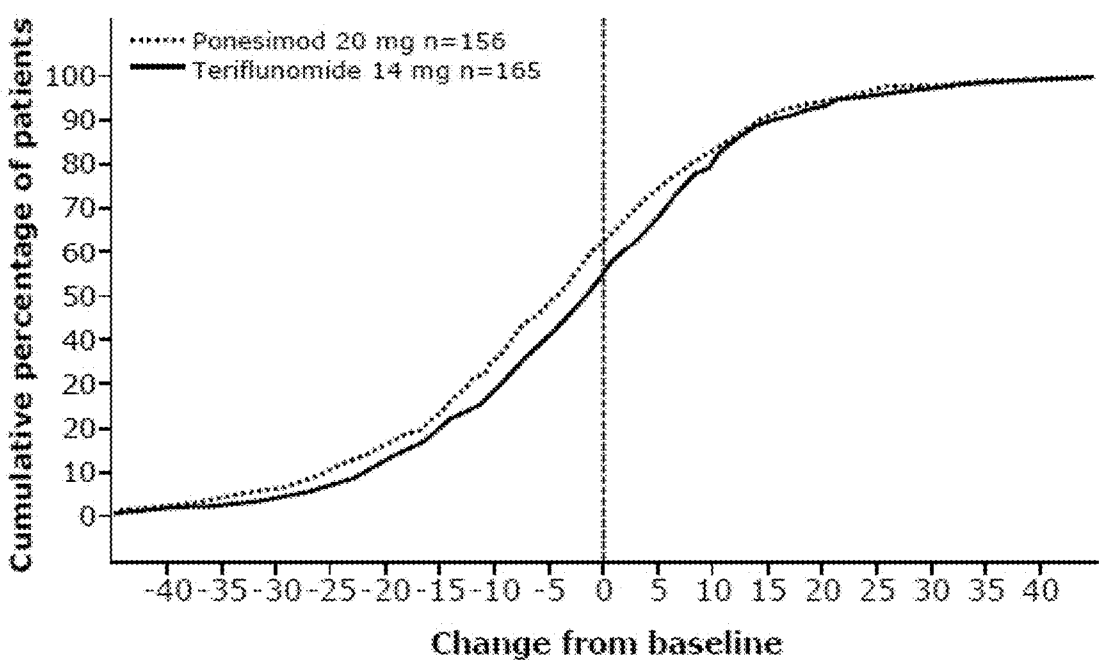
FIG. 15 shows cumulative distribution function of change from baseline at week 108 in FSIQ-RMS weekly symptoms score for patients with baseline fatigue above the median.

Mean change from baseline to Week 108 in FSIQ-RMS weekly symptoms score for patients with baseline fatigue above the median is shown in FIG. 14. Cumulative distribution function of change is shown in FIG. 15.

Figure 16:
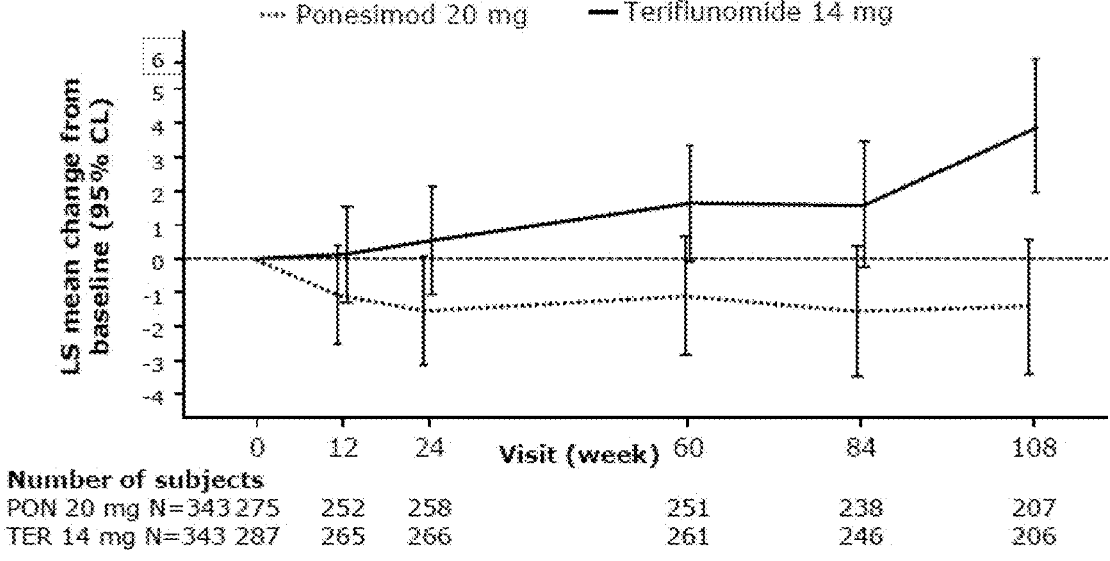
FIG. 16 shows change from baseline to week 108 in FSIQ-RMS weekly symptoms score for patients without DMT treatment two years prior to randomization.
Figure 17:
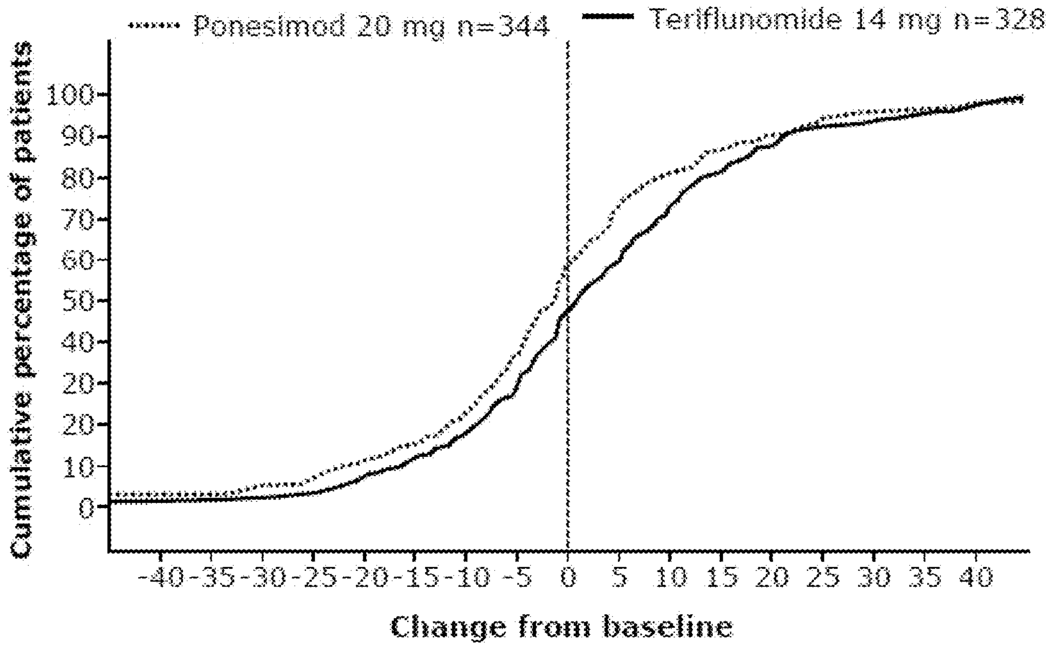
FIG. 17 shows cumulative distribution function of change from baseline at week 108 in FSIQ-RMS weekly symptoms score for patients without DMT treatment two years prior to randomization.

Example 1D: Change from Baseline to Week 108—Patients with No Prior DMT Treatment Mean change from baseline to Week 108 in FSIQ-RMS weekly symptoms score for patients with no prior DMT treatment within about two years prior to initiation of treatment is shown in FIG. 16. Cumulative distribution function of change is shown in FIG. 17. Results are summarized in Table 12 below.

Patient improvement was clinically meaningful in 31.4% of patients on ponesimod (P=0.052), and about 75% of patients on ponesimod remained stable or improved by Week 108 (P=0.003).

TABLE 12

Change From Baseline to Week 108 in Patients with no Prior DMT Treatment for Ponesimod and Teriflunomide

| Visit | Change From Baseline to Week 108: No Prior DMT Treatment | N | Ponesimod | N | Teriflunomide | P-Value |
|---|---|---|---|---|---|---|
| Week 108 | Improved (<−6.3) | 65 | 31.4% | 54 | 26.2% | 0.052 |
| | Stable (−6.3 < x < +6.3) | 91 | 44.0% | 76 | 36.9% | |
| | Stable or Improved | 156 | 75.4% | 130 | 63.1% | 0.003 |
| | Worsened (≥6.3) | 51 | 24.6% | 76 | 36.9% | |

Figure 18:
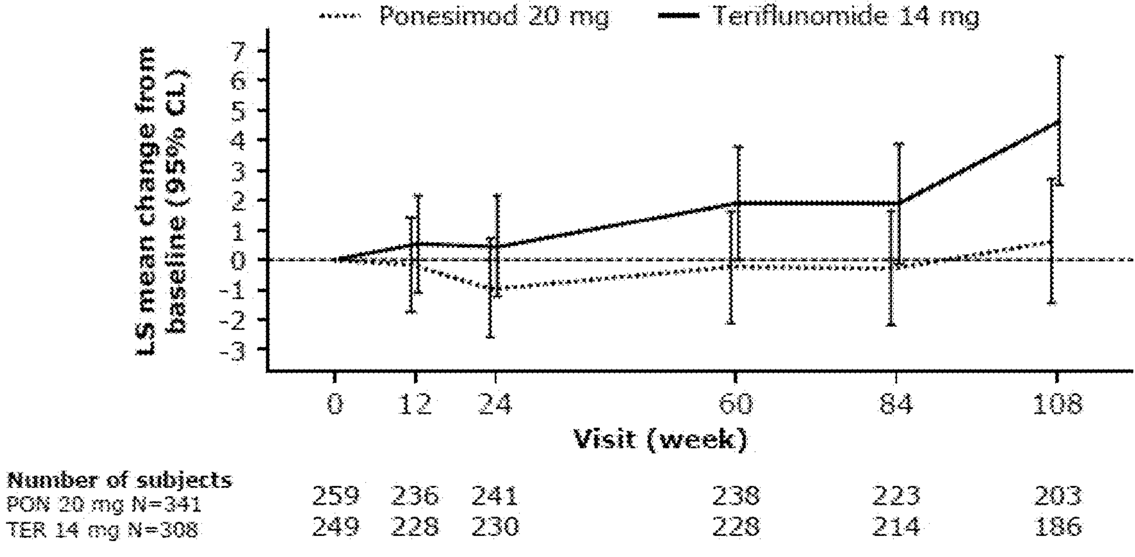
FIG. 18 shows change from baseline to week 108 in FSIQ-RMS weekly symptoms score for patients without Gd+/T1 lesions at baseline.
Figure 19:
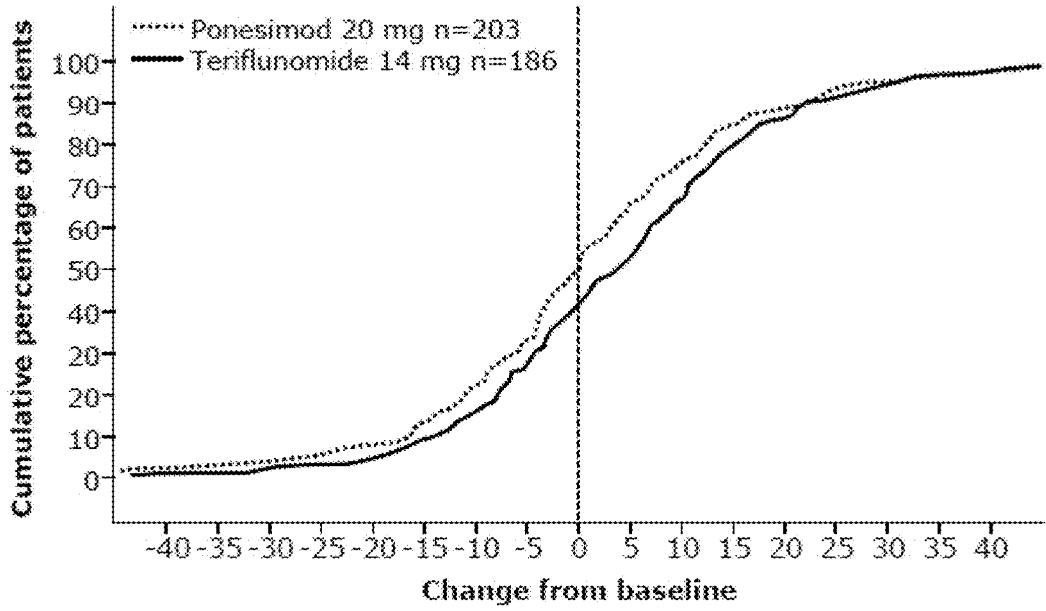
FIG. 19 shows cumulative distribution function of change from baseline at week 108 in FSIQ-RMS weekly symptoms score for patients without Gd+/T1 lesions at baseline.

Example 1E: Change from Baseline to Week 108 in Patients without Gd+T1 Lesions at Baseline Mean change from baseline to Week 108 for change in FSIQ-RMS weekly symptoms score in patients without Gd+T1 lesions at baseline is shown in FIG. 18. Cumulative distribution function of change is shown in FIG. 19. Results are summarized in Table 13 below.

Patients who had stable or improved symptoms of fatigue without baseline Gd+T1 lesions demonstrated a statistically significant difference for ponesimod compared to teriflunomide, about 68% for ponesimod vs. about 57% for teriflunomide (p=0.021).

TABLE 13

| Change From Baseline to Week 108 in Patients without Gd + T1 Lesions at Baseline | | | | | | | |
|---|---|---|---|---|---|---|---|
| Visit | Change From Baseline to Week 108: No Gd + T1 Lesions | N | Ponesi-mod | N | Teri-flunomide | P-Value |
| Week 108 | Improved (<−6.3) | 61 | 30.0% | 48 | 25.8% | 0.257 |
| | Stable (−6.3 < x < +6.3) | 76 | 37.4% | 58 | 31.2% | |
| | Stable or Improved | 137 | 67.5% | 106 | 57.0% | 0.021 |
| | Worsened (≥6.3) | 66 | 32.5% | 80 | 43.0% | |

Figure 20:
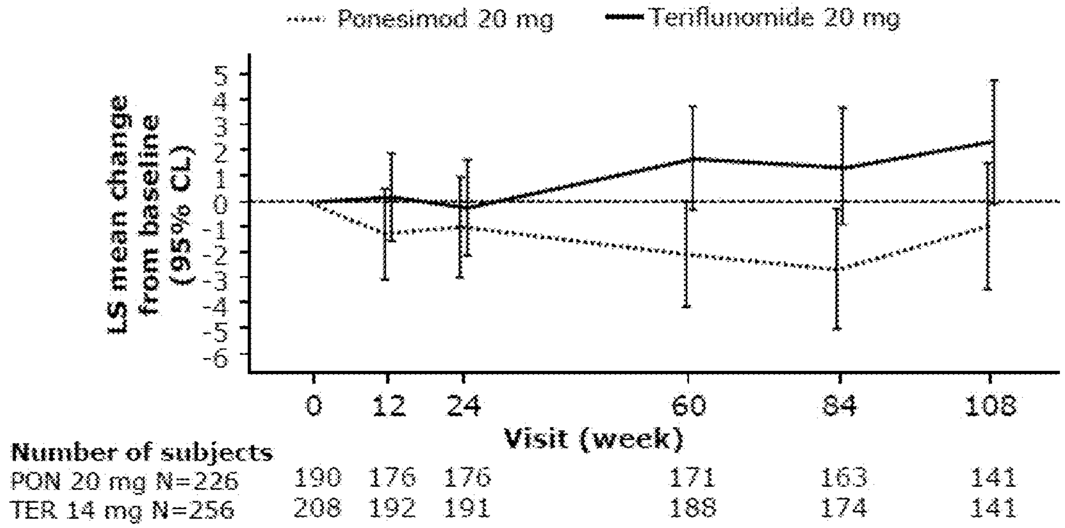
FIG. 20 shows change from baseline to week 108 in FSIQ-RMS weekly symptoms score for patients with Gd+/T1 lesions at baseline.
Figure 21:
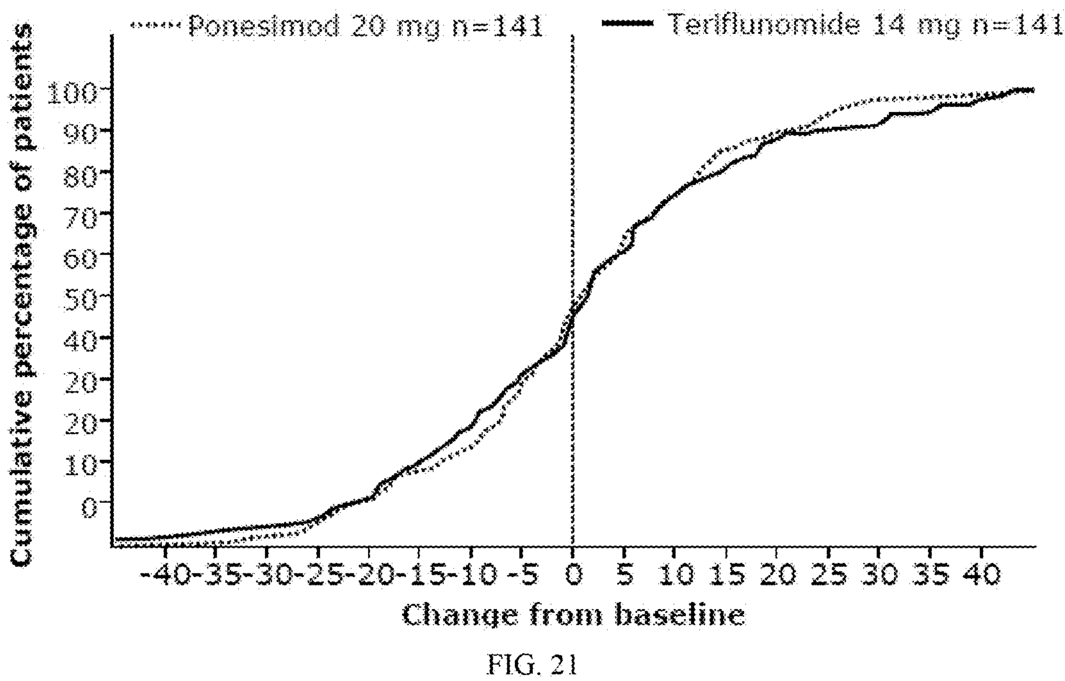
FIG. 21 shows cumulative distribution function of change from baseline at week 108 in FSIQ-RMS weekly symptoms score for patients with Gd4/T1 lesions at baseline.

Example 1F: Change from Baseline to Week 108 in Patients with Gd+T1 Lesions at Baseline Mean change from baseline to Week 108 for change in FSIQ-RMS weekly symptoms score in patients with Gd+T1 lesions at baseline is shown in FIG. 20. Cumulative distribution function of change is shown in FIG. 21.

Example 1G: Change from Baseline to Week 108—Baseline EDSS≤3.5

Figure 22:
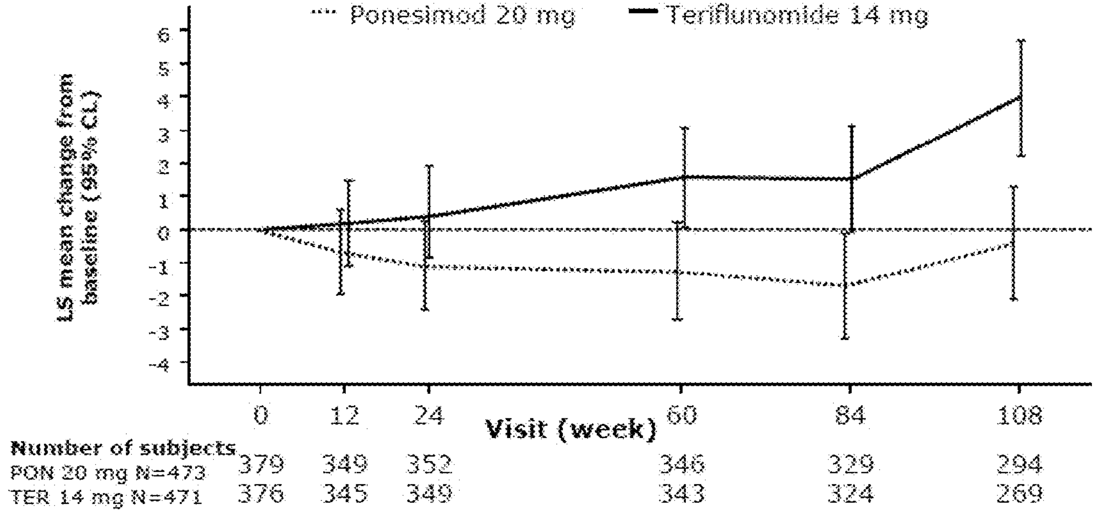
FIG. 22 shows change from baseline to week 108 in FSIQ-RMS weekly symptoms score for patients with baseline EDSS≤3.5.
Figure 23:
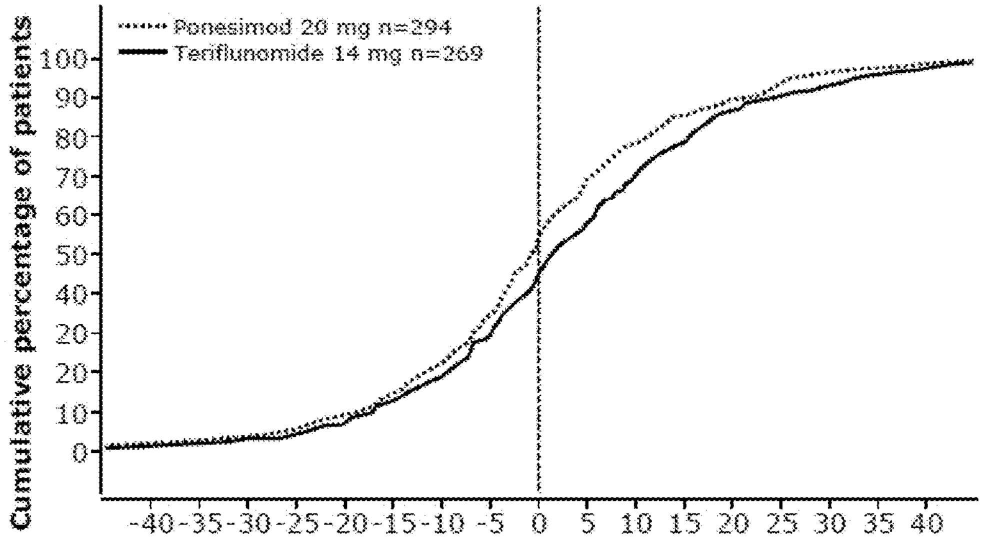
FIG. 23 shows cumulative distribution function of change from baseline at week 108 in FSIQ-RMS weekly symptoms score for patients with baseline EDSS≤3.5.

Mean change from baseline to Week 108 for change in FSIQ-RMS weekly symptoms score for patients with lower baseline EDSS is shown in FIG. 22. Cumulative distribution function of change is shown in FIG. 23. Results are summarized in Table 14 below.

TABLE 14

| Change From Baseline to Week 108 in Patients with Baseline EDSS ≤3.5 | | | | | | |
|---|---|---|---|---|---|---|
| Visit | Change From Baseline to Week 108: Baseline EDSS <3.5 | N | Ponesi-mod | N | Teri-flunomide | P-Value |
| Week 108 | Improved (<−6.3) | 90 | 30.6% | 75 | 27.9% | 0.318 |
| | Stable (−6.3 < x < +6.3) | 120 | 40.8% | 92 | 34.2% | |
| | Stable or Improved | 210 | 71.4% | 167 | 62.1% | 0.010 |
| | Worsened (≥6.3) | 84 | 28.6% | 102 | 37.9% | |

Figure 24:
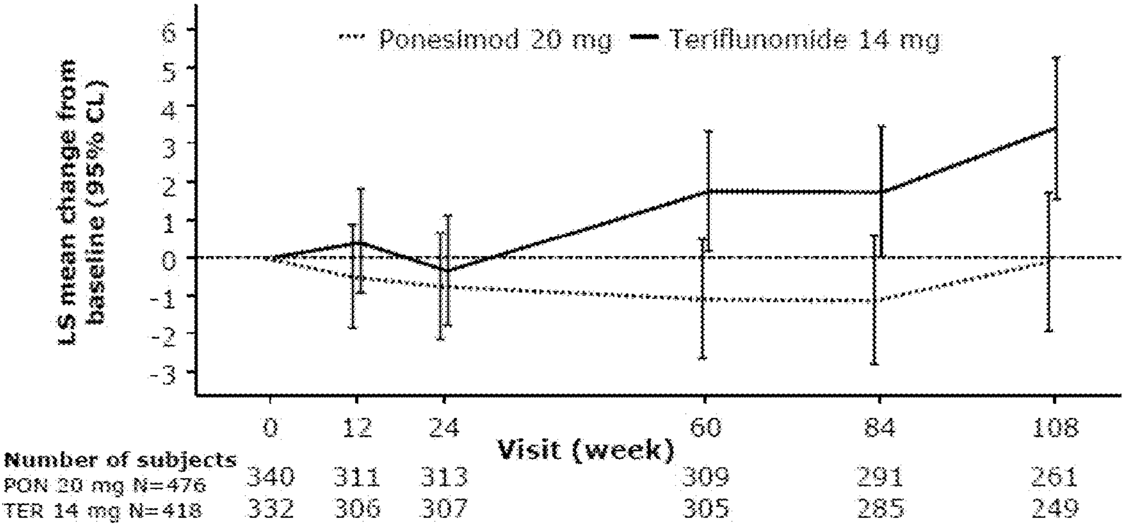
FIG. 24 shows change from baseline to week 108 in FSIQ-RMS weekly symptoms score for patients having one or fewer relapses at baseline.
Figure 25:
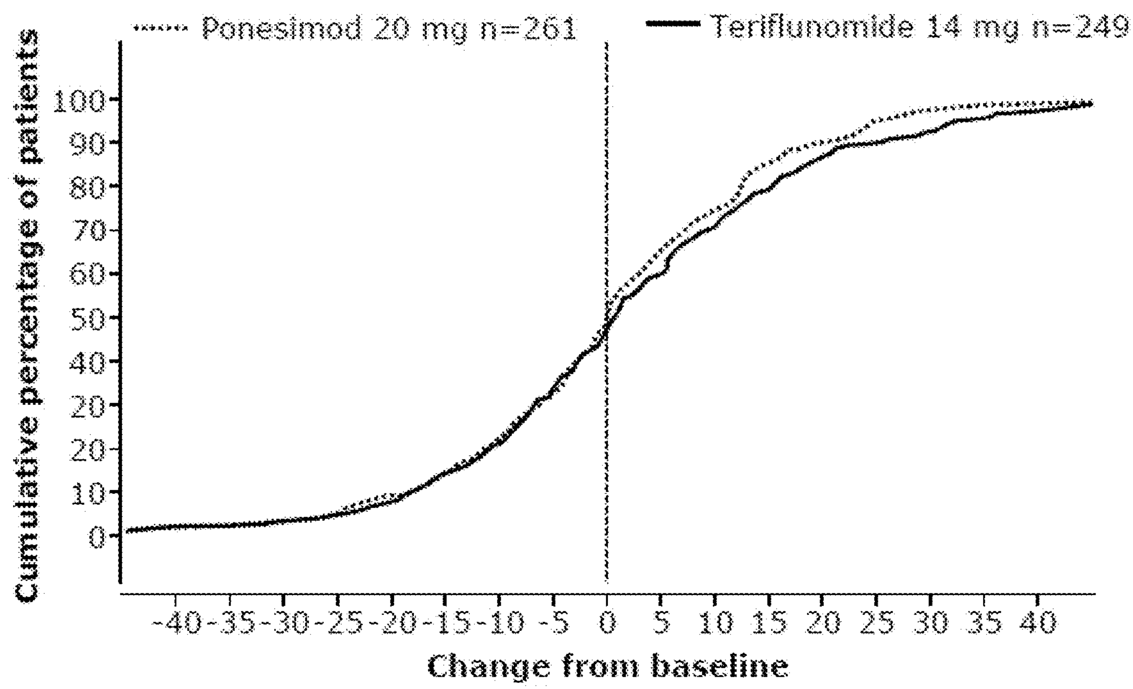
FIG. 25 shows cumulative distribution function of change from baseline at week 108 in FSIQ-RMS weekly symptoms score for patients having one or fewer relapses at baseline.

Example 1H: Change from Baseline to Week 108—Patients with One or Fewer Prior Relapses at Baseline Mean change from baseline to Week 108 for change in FSIQ-RMS weekly symptoms score for patients with one or fewer prior relapses at baseline is shown in FIG. 24. Cumulative distribution function of change is shown in FIG. 25.

Figure 26:
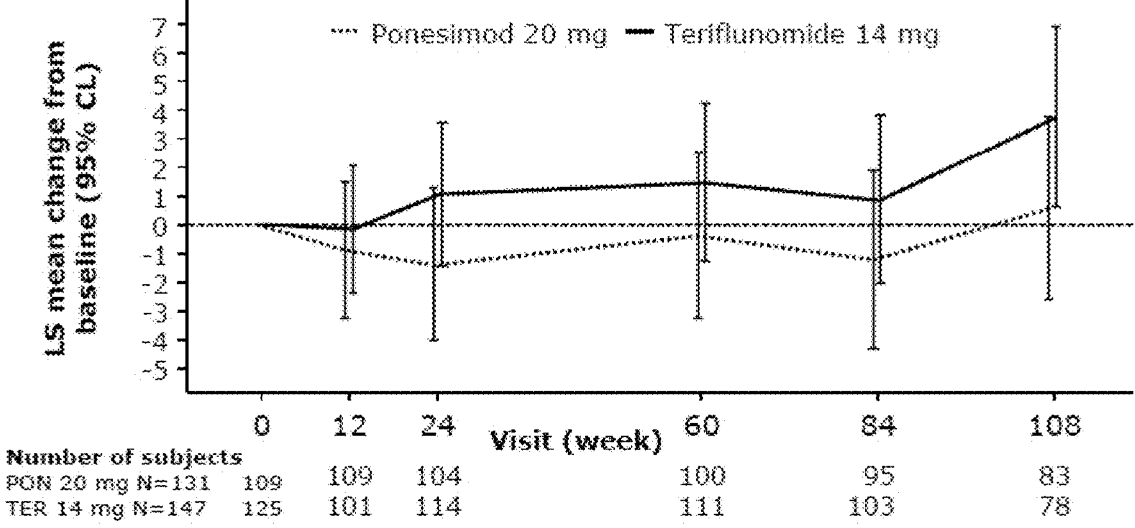
FIG. 26 shows change from baseline to week 108 in FSIQ-RMS weekly symptoms score for patients having two or more relapses at baseline.
Figure 27:
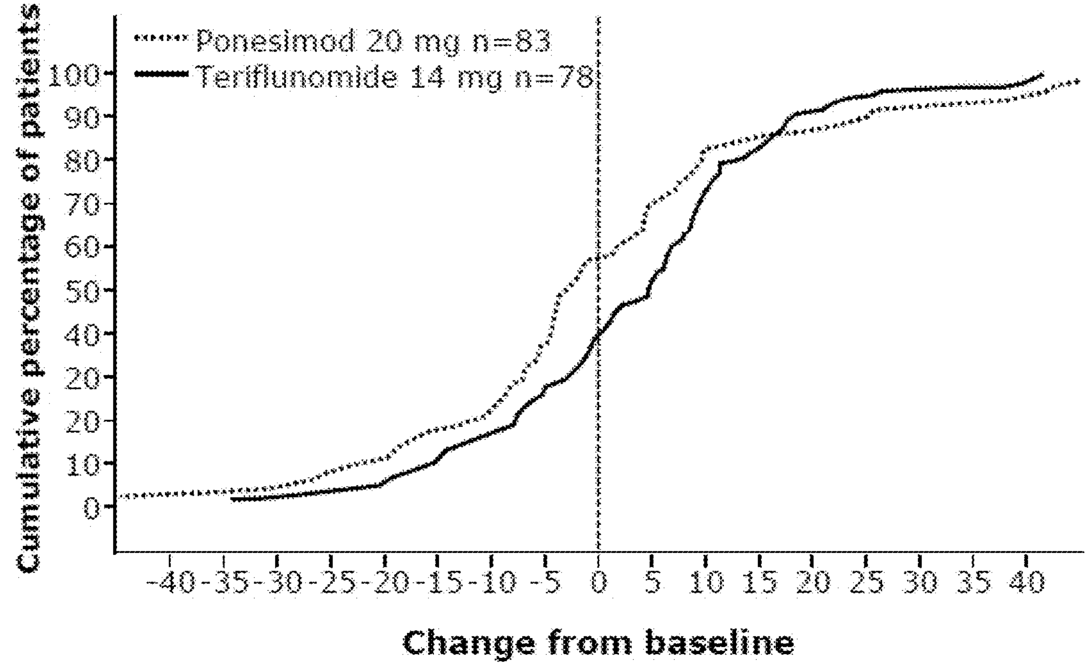
FIG. 27 shows cumulative distribution function of change from baseline at week 108 in FSIQ-RMS weekly symptoms score for patients having two or more relapses at baseline.

Example 1I: Change from Baseline to Week 108—Patients with Two or More Prior Relapses at Baseline Mean change from baseline to Week 108 for change in FSIQ-RMS weekly symptoms score for patients with two or more prior relapses at baseline is shown in FIG. 26. Cumulative distribution function of change is shown in FIG. 27.

Example 2: Pre-Specified MRI Endpoints and No Evidence of Disease Activity (NEDA) Status In this study, prespecified MRI-based endpoints and no evidence of disease activity (NEDA) status is evaluated.

Patients (18-55 years) with RMS (expanded disability status scale scores: 0-5.5) were randomized (1:1) to receive ponesimod (PON) 20 mg or teriflunomide (TER) 14 mg for 108 weeks. MRI assessments were: volume of T2 lesions; mean number of new gadolinium-enhancing (Gd+) T1 lesions and new/enlarging T2 lesions; and absence of active MRI lesions at week 108. NEDA-3 status (absence of confirmed relapse, Gd+T1 lesions and new/enlarging T2 lesions on annual MRIs, and 12-week confirmed disability accumulation) was evaluated from baseline to week 108.

A total of 985/1133 (86.9%) randomized patients completed the study. MRI findings for PON vs TER from baseline to week 108, respectively, were: least square (LS) mean difference (PON-TER) in change from baseline in total volume of T2 lesions: −399.2 $mm^3$ (95% CLs: −651.5; −146.8, p=0.00[2]); mean number of new Gd+T1 lesions per scan: 0.18 vs 0.43 (rate ratio [RR]: 0.42, 95% CLs: 0.31; 0.56, p<0.0001); mean numbers of new/enlarging T2 lesions per year: 1.40 vs 3.16 (RR: 0.44, 95% CLs: 0.36; 0.54, p<0.0001); PON vs TER odds ratio (OR [95% CL]) for absence of new Gd+T1 lesions: 2.18 (1.61; 2.95, p<0.0001) and absence of new/enlarging 12 lesions: 1.71 (1.30; 2.25, p=0.0001). At week 108, 28.2% (159/564) PON vs 18.3% (102/558) TER patients (OR: 1.70, CL: 1.27; 2.28, p=0.0004) achieved NEDA-3. The most frequent reason for not achieving NEDA-3 status at week 108 was presence of new/enlarging T2 lesions.

Patients treated with ponesimod demonstrated a higher proportion of patients achieving NEDA-3 status compared to those treated with teriflunomide.

Conclusions

This study demonstrates the superior efficacy of ponesimod over the active control, including with respect to ARR, CUALs, and MS-fatigue.

This study also demonstrates that the safety profile of ponesimod appears to be consistent with previously observed safety findings with ponesimod, and the known safety profile of other SIP receptor modulators. The gradual up-titration appears to successfully mitigate first-dose effects of ponesimod and supports forgoing first dose monitoring for patients with no risk factors for symptomatic bradycardia.

Example 3—Early Stage Multiple Sclerosis (ESMS) Patient Population

Introduction

OPTIMUM, a phase 11, randomized, double blind study, demonstrated superiority of ponesimod over teriflunomide with respect to:

a) ponesimod reduced annualized relapse rate (ARR) by 30.5% vs. teriflunomide.

b) ponesimod reduced the mean number of combined unique active lesions (CUALs) per year on annual brain MRIs from baseline to week 108 by 56% compared with teriflunomide; and c) the change in Fatigue Symptoms and Impacts Questionnaire—Relapsing Multiple Sclerosis (FSIQ-RMS) weekly symptom score from baseline to week 108 was significantly lower for fatigue symptoms in the ponesimod group than the teriflunomide group; a decrease from baseline represents improvement in fatigue symptoms.

It is well established that early treatment in multiple sclerosis (MS) with higher-potency therapies improve long-term outcomes. Subgroup analyses of the OPTIMUM study was performed to test whether a patient population with ESMS has a differential benefit with ponesimod compared with teriflunomide.

Method

The study design and treatment details of the OPTIMUM study have been published previously (see also Example 1).

In the OPTIMUM study, baseline Expanded Disability Status Scale (EDSS) scores were between 0-5.5.

This subgroup analysis examined patients with EDSS≤3 (up to moderate disability in one function, or mild disability in three or four functions; no impairment to walking), and/or who were treatment naïve.

Treatment differences on ARR, CUALs and MS-fatigue in these subgroups were compared with the overall population.

All statistical analyses were performed on all participants who were randomized.

ARR differences and mean number of CUALs were examined using a negative binomial regression model with adjusting for the log time in the study (in years) as an offset.

Changes in FSIQ-RMS scores were examined using mixed effect model repeated measures models with baseline score as a covariate.

Interaction terms with subgroups were also added to test if the observed treatment differences differed within each subgroup.

Results

Figure 28:
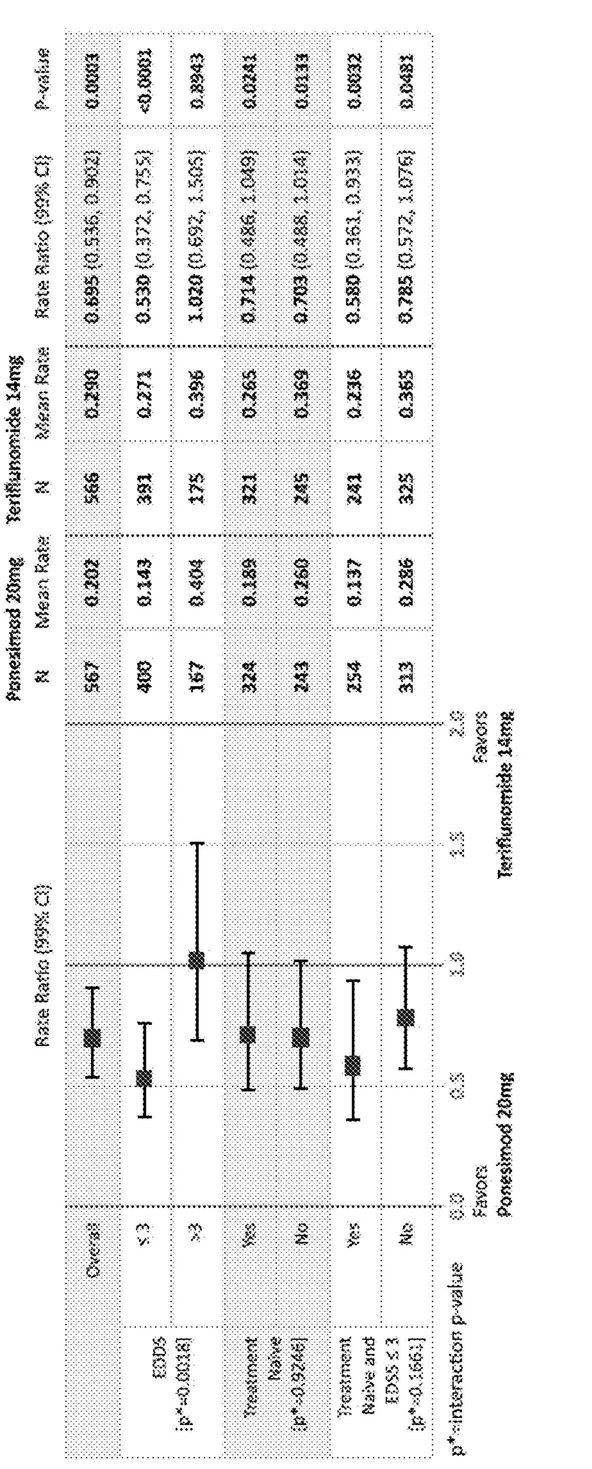
FIG. 28 depicts a table of results for annualized relapse rate (ARR) for various subgroups of patients treated with ponesimod and teriflunomide.

Of 1468 patients screened. 1133 were randomized (ponesimod, n=567; teriflunomide, n=566) and were included in the analysis. The results are summarized in FIG. 28. In the EDSS≤3 subgroup, ponesimod treatment reduced ARR by 47%, RR=0.530 [99% CLs: 0.372, 0.755].

MS-fatigue mean difference improved to −4.31 [95% CLs: −6.99, −1.63]) in favor of ponesimod in the EDSS≤3 subgroup. The results are summarized in FIG. 29. Change from baseline to week 108 in the MS-fatigue was statistically significantly lower in the ponesimod group compared with the teriflunomide group for the EDSS≤3 subgroup (mean difference: −4.31 [95% CLs: −6.99, −1.63]; an increase from baseline indicates worsening in fatigue symptoms.

Figure 30:
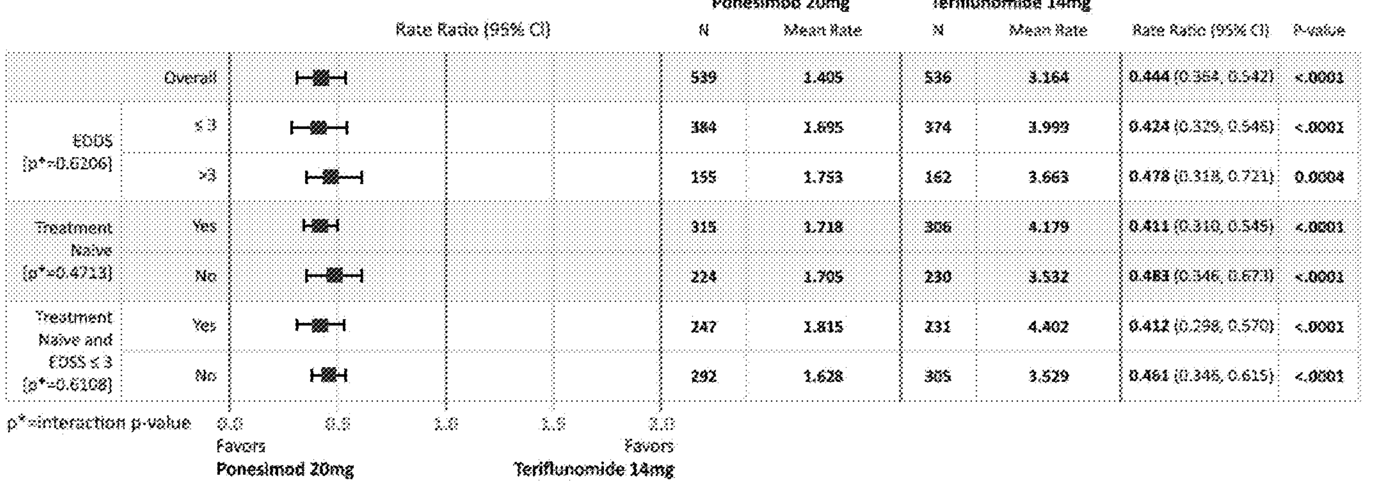
FIG. 30 depicts a table of results for combined unique active lesions (CUALs) for various subgroups of patients treated with ponesimod and teriflunomide.

Regarding CUALs, patients with EDSS≤3 and treatment-naïve patients benefited from ponesimod compared with teriflunomide, and these results were consistent with the overall population, as shown in FIG. 30.

Conclusions

Ponesimod demonstrated increased clinical benefit as compared with teriflunomide in ESMS subgroups and compared with the overall population. This subgroup analysis confirms the advantage of using ponesimod as an early high efficacy treatment.

What is claimed:

1. A method of treating a patient suffering from early-stage multiple sclerosis (ESMS), the method comprising:
- determining an expanded disability status scale (EDSS) score of the patient;
- identifying the patient as having early-stage multiple sclerosis (ESMS) in the case that the patient has an EDSS score that is ≤3.0; and
- administering ponesimod to the patient using a regimen that is effective to treat the ESMS.

2. A method of treating a patient suffering from early-stage multiple sclerosis (ESMS), the method comprising:
- determining an expanded disability status scale (EDSS) score of the patient;
- identifying the patient as having ESMS in the case that the patient has an EDSS score that is ≤3.0; and
- administering ponesimod to the patient using a regimen that is effective to reduce the number of combined unique active lesions (CUALs) in the patient by at least 50%, relative to a patient population at substantially the same level of disease progression receiving a standard of care treatment that does not comprise ponesimod.

3. A method of treating a patient suffering from early-stage multiple sclerosis (ESMS), the method comprising:
- determining an expanded disability status scale (EDSS) score of the patient;
- identifying the patient as having ESMS in the case that the patient has an EDSS score that is ≤3.0; and
- administering ponesimod to the patient using a regimen that is effective to reduce the annualized relapse rate (ARR) in the patient by at least 25%, relative to a patient population at substantially the same level of disease progression receiving a standard of care treatment that does not comprise ponesimod.

4. A method of treating a patient suffering from early-stage multiple sclerosis (ESMS) and fatigue, the method comprising:
- determining an expanded disability status scale (EDSS) score of the patient;
- identifying the patient as having ESMS in the case that the patient has an EDSS score that is ≤3.0; and
- administering ponesimod to the patient using a regimen that is effective to reduce MS-fatigue mean difference to about −4%, relative to a patient population at substantially the same level of disease progression receiving a standard of care treatment that does not comprise ponesimod.

5. The method of claim 1, wherein about 20 mg of ponesimod is administered orally once daily.

6. The method of claim 1, wherein the regimen comprises an up-titration step at initiation of the method or upon re-initiation of the method after a discontinuation, comprising administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; and 9 mg of ponesimod on day 11; 10 mg of ponesimod on days 12, 13, and 14, followed by administering 20 mg of ponesimod once daily thereafter.

7. The method of claim 1, wherein the ESMS is relapsing multiple sclerosis.

8. The method of claim 7, wherein the relapsing multiple sclerosis comprises relapsing-remitting disease, clinically isolated syndrome, or active secondary progressive disease.

9. The method of claim 1, wherein the patient is treatment naive.

10. The method of claim 2, wherein about 20 mg of ponesimod is administered orally once daily.

11. The method of claim 2, wherein the regimen comprises an up-titration step at initiation of the method or upon re-initiation of the method after a discontinuation, comprising administering orally once daily 2 mg of ponesimod on days 1 and 2; 3 mg of ponesimod on days 3 and 4; 4 mg of ponesimod on days 5 and 6; 5 mg of ponesimod on day 7;

6 mg of ponesimod on day 8; 7 mg of ponesimod on day 9; 8 mg of ponesimod on day 10; and 9 mg of ponesimod on day 11; 10 mg of ponesimod on days 12, 13, and 14, followed by administering 20 mg of ponesimod once daily thereafter.

12. The method of claim 2, wherein the ESMS is relapsing multiple sclerosis.

13. The method of claim 12, wherein the relapsing multiple sclerosis comprises relapsing-remitting disease, clinically isolated syndrome, or active secondary progressive disease.

14. The method of claim 2, wherein the standard of care treatment comprises teriflunomide.

15. The method of claim 14, wherein the standard of care treatment comprises administration of about 14 mg of teriflunomide orally once daily.

16. The method of claim 2, wherein the patient is treatment naive.

17. The method of claim 3, wherein about 20 mg of ponesimod is administered orally once daily.

18. The method of claim 3, wherein the regimen comprises an up-titration step at initiation of the method or upon re-initiation of the method after a discontinuation, comprising administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; and 9 mg of ponesimod on day 11; 10 mg of ponesimod on days 12, 13, and 14, followed by administering 20 mg of ponesimod once daily thereafter.

19. The method of claim 3, wherein the ESMS is relapsing multiple sclerosis.

20. The method of claim 19, wherein the relapsing multiple sclerosis comprises relapsing-remitting disease, clinically isolated syndrome, or active secondary progressive disease.

21. The method of claim 3, wherein the standard of care treatment comprises teriflunomide.

22. The method of claim 21, wherein the standard of care treatment comprises administration of about 14 mg of teriflunomide orally once daily.

23. The method of claim 3, wherein the patient is treatment naive.

24. The method of claim 4, wherein about 20 mg of ponesimod is administered orally once daily.

25. The method of claim 4, wherein the regimen comprises an up-titration step at initiation of the method or upon re-initiation of the method after a discontinuation, comprising administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; and 9 mg of ponesimod on day 11; 10 mg of ponesimod on days 12, 13, and 14, followed by administering 20 mg of ponesimod once daily thereafter.

26. The method of claim 4, wherein the ESMS is relapsing multiple sclerosis.

27. The method of claim 26, wherein the relapsing multiple sclerosis comprises relapsing-remitting disease, clinically isolated syndrome, or active secondary progressive disease.

28. The method of claim 4, wherein the standard of care treatment comprises teriflunomide.

29. The method of claim 28, wherein the standard of care treatment comprises administration of about 14 mg of teriflunomide orally once daily.

30. The method of claim 4, wherein the patient is treatment naive.

* * * * *